United States Patent [19]

Dahmen et al.

[11] Patent Number: 4,675,392

[45] Date of Patent: Jun. 23, 1987

[54] GLYCOSIDES

[75] Inventors: Jan Dahmen, Akarp; Torbjörn Frejd, Södra Sandby; Göran Magnusson; Ghazi Noori, both of Lund, all of Sweden

[73] Assignee: Svenska Sockerfabriks AB, Malmö, Sweden

[21] Appl. No.: 673,796

[22] Filed: Nov. 21, 1984

Related U.S. Application Data

[63] Continuation-in-part of Ser. No. 504,154, Jun. 14, 1983, abandoned.

[30] Foreign Application Priority Data

Jun. 23, 1982 [SE] Sweden .................................. 8203925

[51] Int. Cl.$^4$ ....................................... C07H 15/04
[52] U.S. Cl. ............................. 536/17.6; 536/17.2; 536/17.5; 536/17.9
[58] Field of Search ................. 536/17.2, 17.3, 17.4, 536/17.5, 17.6, 17.7, 17.8, 17.9, 18.2

[56] References Cited

U.S. PATENT DOCUMENTS 3,547,828 12/1970 Mansfield et al. ................. 536/4.1
4,215,213 7/1980 Inoue et al. ...................... 536/18.2

OTHER PUBLICATIONS

Pigman *The Carbohydrates*, 1957, pp. 200–201.

*Primary Examiner*—Johnnie R. Brown
*Assistant Examiner*—Elli Peseler
*Attorney, Agent, or Firm*—Burns, Doane, Swecker & Mathis

[57] ABSTRACT

An O-glycoside having the general formula:

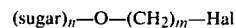

$$(sugar)_n-O-(CH_2)_m-Hal$$

wherein Hal is chlorine, bromine or iodine, m is an integer of 2–20 inclusive and n is an integer of 1 to 10, inclusive, with the proviso that when $n=1$ and $m=2$, the aldose is different from glucose;

An O-glycoside having the general formula:

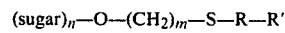

$$(sugar)_n-O-(CH_2)_m-S-R-R'$$

wherein n is an integer of from 1–10, inclusive, m is an integer of from 2–20, inclusive, R is selected from the group consisting of alkyl having at most 25 carbon atoms and aryl and R' is selected from the group consisting of H, CHO, CH(OR')$_2$, NO$_2$, NH$_2$, OH, SH, COOH, COOCH$_3$, COOCH$_2$CH$_3$, CONHNH$_2$ and CON$_3$, wherein R'' is C$_{1-4}$-alkyl;

A glycoconjugate having the general formula:

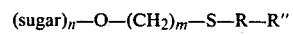

$$(sugar)_n-O-(CH_2)_m-S-R-R''$$

wherein n is an integer of from 1–10, inclusive, m is an integer of from 2–20, inclusive, R is selected from the group consisting of alkyl having at most 25 carbon atoms and aryl and R'' constitutes a carrier;

A bi-dentate O-glycoside having the general formula:

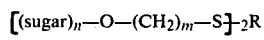

$$[(sugar)_n-O-(CH_2)_m-S]_2R$$

wherein m, n and R have the above meaning; and processes for their preparation.

1 Claim, 9 Drawing Figures

Principal applications of 2-bromoethyl glycosides

HS-▨-X ≡ functionalised thiol
Ⓟ ≡ protein or particle
HS-▨▨▨-SH ≡ di-thiol
R ≡ carbohydrate and or protecting group(s)

Principal applications of 2-bromoethyl glycosides

Examples of 2-bromoethyl glycoside syntheses $^1$H-NMR spectrum of 2-bromoethyl 2,3,4-tri-O-acetyl-α-L-fucopyranoside (7; 2-bromoethyl part). Top: Experimental spectrum; middle: simulated spectrum with line-width 1.2 Hz; bottom: simulated spectrum with line-width 0.1 Hz.

Model reactions for the coupling of spacer-arm glycosides to proteins

Preparation of agglutination inhibitor glycosides from 2-bromoethyl glycosides.

The 2-bromoethyl group in synthetic carbohydrate chemistry, exemplified by a total synthesis of the blood-group H specific glycoside.

49

57 R-Br, R'-R"-Bn, R'''-Ac
58 R-Br, R'-R"-H, R'''-Ac
59 R-Br, R'-R"-R'''-Ac
60 R-Br, R'-Bz, R"-Bn, R'''-Ac
61 R-Br, R'-Bz, R"-H, R'''-Ac
63 R-S~COOMe, R'-R"-R'''-Ac
64 R-S~COOMe, R'-R"-R'''-H
65 R-S~WWWW, R'-R"-R'''-Ac
66 R-S~WWWW, R'-R"-R'''-H
67 R-H, R'-R"-R'''-Ac
68 R-H, R'-R"-R'''-H
69 R-S~CONH-BSA, R'-R"-R'''-H
70 R-S  CONH-KLH, R'-R"-R'''-H

50 R-R'-R"-Ac
51 R-H, R'R"-CHPh
52 R-Bn, R'R"-CHPh
54 R-R"-Bn, R'H
55 R-Bz, R'R"-CHPh
56 R-Bz, R'-H, R"-Bn

71

72 R-Bn, R'Ac
73 R-H, R'-Ac
74 R-R'-Ac

53

62

49

75

| 76 | R=Br, R'=Bn, R''=Ac |
| 77 | R=Br, R'=H, R''=Ac |
| 78 | R=Br, R'=R''=Ac |
| 79 | R=S~COOMe, R'=R''=Ac |
| 80 | R=S\/\/\/\/\/, R'=R''=Ac |

| 81 | R=S~COOMe, R'=R''=Ac |
| 82 | R=S~COOMe, R'=R''=H |
| 83 | R=S\/\/\/\/\/, R'=R''=Ac |
| 84 | R=S\/\/\/\/\/, R'=R''=H |
| 85 | R=H, R'=Bn, R''=Ac |
| 86 | R=R'=H, R''=Ac |
| 87 | R=H, R'=R''=Ac |
| 88 | R=R'=R''=H |
| 89 | R=S~CONH-BSA, R'=R''=H |
| 90 | R=S~CONH-KLH, R'=R''=H |

91  R = H
92  R = Ac

Pullulan → 91 → 92 →

93  R = Ac, R' = Br
94  R = Ac, R' = S∼COOMe
95  R = Ac, R' = S∼∼∼∼COOMe
96  R = Ac, R' = S∼∼∼∼∼
97  R = H,  R' = H
98  R = H,  R' = S∼COOMe
99  R = H,  R' = S∼∼∼∼COOMe
100 R = H,  R' = S∼∼∼∼∼
101 R = H,  R' = S∼CONH − BSA
102 R = H,  R' = S∼CONH − KLH

GLYCOSIDES

The present application is a continuation-in-part of Ser. No. 504,154, filed June 14, 1983, now abandoned.

The present invention relates to new and novel O-glycosides and glycoconjugates, as well as to processes for their preparation.

A growing appreciation of the role of glycoconjugates in biological receptor interactions has recently directed much interest into the chemistry and molecular biology of these compounds. A vast array of biological observations have been described in the recent literature and several excellent reviews have appeared[1]. Blood-group antigens are the classical examples of carbohydrate receptors[2]. During the last few years it has been shown that these receptors are ubiquitous and modern studies now include such diverse fields as lectines[3] and antibodies[4]; cell-surface receptors on bacteria[5], viruses[6], mycoplasma[1a], and protozoans[1a]; bacterial toxins[7]; hormone receptors[8]; cell-growth regulation and oncogenesis[9]; sperm-egg interaction and fertilization[10]; recognition phenomena in plants[11], and targeting of drugs[12].

Chemical synthesis and modification of glycoconjugates has led to for example artificial immunogens for the preparation of carbohydrate specific antibodies[2], artificial glycolipids for the incorporation into liposomes[13] and functionalized glycosides have been used for the preparation of solid phases for affinity chromatography[14]. In all these cases there is a need for stereospecific methods that permit the preparation of pure α- or β-glycosides having spacer-arm aglycons that at a later stage can be covalently coupled to a carrier molecule or particle, preferably under physiological conditions. In addition, simple-aglycon (e.g. methyl and ethyl) glycosides are needed for specificity studies of agglutination systems like erythrocyte-antibody[4] and -bacteria[5] interactions.

Spacer-arm glycosides of oligosaccharides can be prepared by two principally different routes. Total synthesis, using protected monosaccharides as starting materials, usually leads to anomerically pure compounds but the total yield of the reaction sequence is low. In the second approach, the spacer-arm is connected (by glycoside synthesis) to the reducing end of the complete oligosaccharide (obtained from biological material or by synthesis). The latter method is preferred when the oligosaccharide can be obtained in large quantity from an inexpensive starting material (e.g. by partial hydrolysis of polysaccharides). However, it can be difficult to separate α- and β-glycosides especially when long spacer-arms and/or higher oligosaccharides are used.

The general problem of glycoside synthesis has been reviewed in a most recommendable way by Bochkov and Zaikov[15], whereas the methods for preparation of spacer-arm glycosides are scattered in the chemical literature[16].

Certain general criteria can be defined for the preparation of spacer-arm glycosides and their coupling to carrier molecules (or particles):

(i) It should be possible to connect the spacer-arm and the carbohydrate moiety (by glycosides synthesis) in a stereospecific way, so that pure α- and β-glycosides can be obtained.

(ii) The spacer-arm should be compatible with standard reagents and reaction conditions used in synthesis and modification of carbohydrates.

(iii) It should be possible to vary the length, hydrophobicity and end-group functionality of the spacer-arm.

(iv) It should be possible to activate the spacer-arm terminal group at physiological conditions for the following coupling to proteins and other sensitive materials.

(v) The spacer-arm should couple covalently and selectively to the carrier.

(vi) The surface charge and conformation of the carrier (for example protein) should not be changed drastically by the coupled carbohydrate moiety.

In the plethora of methods described in the literature[16], there can be found some individual cases where most of the above-mentioned criteria are met. However, there still exists a need for general methods that allow for a flexible choice of spacer-arm without the necessity of carrying out a new glycoside synthesis for every variation.

There have been a few reports in the literature on the stepwise construction of spacer-arm glycosides[17] where for example the standard allyl protecting group has been used as the initial aglycon. ω-Haloalkyl glycosides have not been used for this purpose (although a synthesis of 2-bromoethyl β-D-glucopyranoside (3) and its further coupling to certain aromatic amines has been reported[18]).

Based on the present invention there is now introduced a new and improved sequential synthesis of spacer-arm glycosides based on the initial preparation of an anomerically pure ω-haloalkyl glycoside (in the following text, reference is usually made to 2-bromoethyl glycosides) of the biologically active oligosaccharide in question followed by the substitution of bromine by a suitably functionalized thiol that allows for the final coupling to the carrier. Furthermore, the bromine atom can be easily replaced by hydrogen (or tritium), using standard hydrogenation conditions, resulting in alkyl glycosides that can be used as inhibitors for the evaluation of agglutination reactions. The 2-bromoethyl group seems to be compatible with most of the standard reactions that are used in synthetic carbohydrate chemistry thus allowing for involved multistep preparations of oligosaccharide 2-bromoethyl glycosides (vide infra).

Although in the present disclosure reference is mostly had to the 2-bromoethyl group as a part of the glycosides prepared it should be noted that the corresponding chloro and iodo derivatives are equally useful. The chloro and iodo varieties thus function in much the same manner as the corresponding bromo derivatives and the invention covers all three halides. Furthermore, the invention covers as starting materials, glycosides, wherein the ω-haloalkyl moiety contains up to about 20 carbon atoms, albeit that smaller alkyl entities are preferred, such as up to about 12 carbon atoms. Particularly preferred are glycosides wherein the ω-haloalkyl moiety contains 2 or 3 carbon atoms.

Such starting materials are prepared by reacting an activated sugar selected from:
a 1-acyl derivative of a sugar,
a 1,2-orthoacyl ester derivative of a sugar,
a 1-bromo derivative of a sugar,
a 1,2 oxazoline derivative of a sugar,
a 1-acyl-2-deoxy-2-phtalimido derivative of a sugar and
a 1-bromo-2-deoxy-2-phtalimido derivative of a sugar;
with an alcohol having the formula: Hal—$(CH_2)_m$—OH wherein Hal equals chlorine, bromine or iodine and m is an integer of from 2-20, inclusive, to form the O-glycoside, and recovering the glycoside formed.

A preferred embodiment of the said process involves glycosidating a 1,2-sugar acetate, orthoester, oxazoline or 1-acyl-2-phtalimido derivative in the presence of a Lewis acid. Another embodiment of the process of the invention involves glycosidation of a glycosyl bromide with the aid of a heavy-metal salt, optionally protecting the 2-hydroxyl group. The reaction may be performed in an organic solvent, for example methylene chloride.

For the purpose of attaching the glycoside prepared to a spacer-arm, the process of the invention comprises nucleophilic addition of a bi-functional spacer-arm compound, the nucleophilic functionality of which comprises sulfur. The compound hereby obtained may via its other functionality be then covalently linked to a carrier. Such carrier may comprise a protein or a modified polysaccharide, in which case the linking reaction is preferably performed in aqueous solution. The said other functionality of the spacer-arm compound may be selected from CHO, COOH, CON$_3$ and NH$_2$, H, CH(OR")$_2$, NO$_2$, OH, SH, COOCH$_3$, COOCH$_2$CH$_3$, CONHNH$_2$, wherein R" is C$_{1-4}$-alkyl.

The said process finds particular utility when a mixture of α- and β-2-bromoethyl glycosides is formed, in that the isomers may be easily separated, the desired isomer being recovered.

Some applications of the inventive concept are diagrammatically shown in FIG. 1 as appended.

The invention provides for new and novel O-glycosides having the general formula:

$$(sugar)_n-O-(CH_2)_m-S-R-R'$$

wherein n is an integer of from 1-10, inclusive, m is an integer of from 2-20, inclusive, R is selected from the group consisting of alkyl having at most 25 carbon atoms and aryl and R' is selected from the group consisting of H, CHO, CH(OR")$_2$, NO$_2$, NH$_2$, OH, SH, COOH, COOCH$_3$, COOCH$_2$CH$_3$, CONHNH$_2$ and CON$_3$, wherein R" is C$_{1-4}$-alkyl. In the said formula the sugar moiety is preferably selected from the group of aldoses defined below in this disclosure. Moreover, in the above formula R' is suitably a carboxylic acid derivative, preferably an ester. R' may also preferably be a sulfhydryl group, hydrogen, an amino group or a nitro group. In the two last instances it is also preferred that R is aryl.

In the O-glycoside of the invention the sugar is preferably an aldose selected from a D-glucose, D-galactose, D-mannose, D-xylose, L-fucose, 2-acetamido-2-deoxy-D-glucose, 2-deoxy-2-phtalimido-D-glucose, 2-acetamido-2-deoxy-D-galactose, 2-azido-2-deoxy-D-glucose, 2-azido-2-deoxy-D-galactose, D-glucuronic acid, D-galacturonic acid, 2-deoxy-2-phtalimido-D-glucose and 2-deoxy-2-phtalimido-D-galactose. In particular, the aldose is galactose and n is preferably an integer from 1-4, inclusive. In another preferred embodiment the sugar moiety of the O-glycoside of the invention contains both D-galactose and 2-acetamido-2-deoxy-D-glucose or 2-acetamido-2-deoxy-D-galactose, in which case n is preferably an integer from 2-5, inclusive.

Examples of neo-glycolipids for use as hydrophobic coating materials are:
D-Galβ1→4-D-GlcNAcβOCH$_2$CH$_2$S—(CH$_2$)$_2$CH$_3$,
L-Fucα1→2-D-GalβOCH$_2$CH$_2$S—(CH$_2$)$_2$CH$_3$,
D-Galα1→4-D-Galβ1-4-D-Glc OCH$_2$CH$_2$S—(CH$_2$)$_2$CH$_3$,
D-Galα1→4-D-Galβ1-4-D-GlcNAc OCH$_2$CH$_2$S—(CH$_2$)$_2$CH$_3$,
D-Glcα1→6-D-Glcα1-4-D-Glc 1-4-D-Glc OCH$_2$CH$_2$S—(CH$_2$)$_2$CH$_3$,
and
D-Galβ1→4-D-GlcNAcβOCH$_2$CH$_2$S—(CH$_2$)$_2$CH$_3$,
wherein 1 is <24, e.g. 7 or 17.

According to another aspect of the invention there is provided a process for preparing an O-glycoside of the general formula:

$$(sugar)_n-O-(CH_2)_m-S-R-R'$$

wherein the different symbols are as previously defined, comprising reacting an O-glycoside having the general formula:

$$(sugar)_n-O-(CH_2)_m-Hal$$

wherein Hal is chlorine, bromine or iodine, m is an integer of 2-20, inclusive, and n is an integer of 1-10, inclusive, with a thiol of the general formula:

$$HS-R-R'$$

wherein R and R' have the above meaning.

The invention also provides for glycoconjugates having the general formula:

$$(sugar)_n-O-(CH_2)_m-S-R-R''$$

wherein n is an integer of from 1-10, inclusive, m is an integer of from 2-20, inclusive, R is selected from the group consisting of alkyl having at most 25 carbon atoms and aryl and R" constitutes a carrier. Such glycoconjugates may have the formula:

D-Galα1→4-D-GalβOCH$_2$CH$_2$—S—CH$_2$CH$_2$-CONH—R''' wherein R''' is selected from the group consisting of residues of proteins, polysaccharides, plastic materials and inorganic materials. Among suitable materials forming R''' there may be mentioned bovine serum albumin (BSA), key-hole limpet haemocyanine (KLH), aminated sepharoses, silica gels, etc.

Particularly preferred glycoconjugates are:
L-Fucα1→2-D-GalβOCH$_2$CH$_2$—S—CH$_2$CH$_2$CONH—R''',
D-Galα1→4-D-Galβ1→4-D-GlcβOCH$_2$CH$_2$—S—CH$_2$CH$_2$CONH—R'''.
D-Galα1→4-D-Galβ1→4-D-GlcNAcβOCH$_2$CH$_2$—S—CH$_2$CH$_2$CONH—R''',
D-Glcα1→6-D-Glcα1→4-D-Glcα1→4-D-GlcβOCH$_2$CH$_2$—S—CH$_2$CH$_2$—CONH—R'''
and
D-Galβ1→4-D-GlbNAcβOCH$_2$CH$_2$—S—CH$_2$CH$_2$-CONH—R''',
wherein R''' is selected from the group consisting of residues of proteins, polysaccharides, plastic materials and inorganic materials.

The above-identified glycoconjugates are suitably prepared by reacting a glycoside of the general formula:

$$(sugar)_n-O-(CH_2)_m-S-R-R'$$

with an appropriate carrier chosen from those mentioned above.

Within its scope the invention provides for a bi-dentate O-glycoside having the general formula:

[(sugar)$_n$—O—(CH$_2$)$_m$—S—]$_2$R wherein m, n and R have the above meaning. Such bi-dentate O-glycosides may be prepared by reacting a glycoside of the general formula:

(sugar)$_n$—O—(CH$_2$)$_m$—Hal with a dithiol of the general formula:

HS—(CH$_2$)$_m$—SH wherein m is an integer of 2–20, inclusive.

The present invention also provides for a process for preparing alkyl O-glycosides, an O-glycoside having the general formula:

(sugar)$_n$—O—(CH$_2$)$_m$—Hal being dehalogenated using gaseous hydrogen and recovering the alkyl O-glycoside formed.

Preferred ethyl glycosides are:
D-Galα1→4-D-GalβOCH$_2$CH$_3$,
L-Fucα1→2-D-GalβOCH$_2$CH$_3$,
D-Galα1→4-D-Galβ1→4-D-GlcβOCH$_2$CH$_3$,
D-Galα1→4-D-Galβ1→4-D-GlcNAcβOCH$_2$CH$_3$,
D-Glcα1→6-D-Glcα1→4-D-Glcα1→4-D-GlcβOCH$_2$CH$_3$,
and
D-Galβ1→4GlcNAcβOCH$_2$CH$_3$.
These are particularly useful as agglutination inhibitors.

Furthermore, in accordance with the invention the number of sugar entities in the O-glycosides described can be increased by transformation to higher glycosides. This is provided for by reacting an activated sugar with a glycoside of the formula:

(sugar)$_{n-x}$—O—(CH$_2$)$_m$—Hal where x is an integer of from 1 to n−1, inclusive, the resulting higher glycoside being recovered. This process may preferably be used to prepare 2-bromoethyl glycosides of the formula:
L-Fucα1→2-D-GalβOCH$_2$CH$_2$Br,
D-Galα1→4-D-Galβ1→4-D-GlcβOCH$_2$CH$_2$Br,
and
D-Galα1→4-D-Galβ1→4-D-GlcNPhthβO—CH$_2$CH$_2$Br.

In the processes described herein it is sometimes desirable to protect certain groups of the sugar reactants to prevent undesired side reactions to take place. This is conventional in the art and for details regarding such protection of reactive groups vide references 59 and 60.

In regard to the glycosides and glycoconjugates prepared according to this invention it is to be noted that the invention covers α- and β-configurations as well as mixtures thereof.

In the following, the invention will be further illustrated by examples in connection with the appended drawings, wherein.

Figure 7:
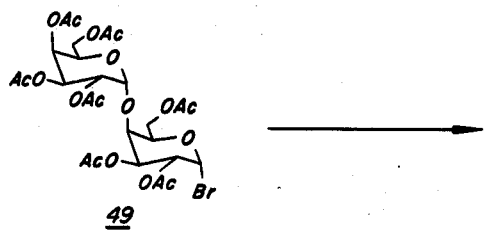
FIG. 7 shows a total synthesis of the P$^k$-antigen.
Figure 7:
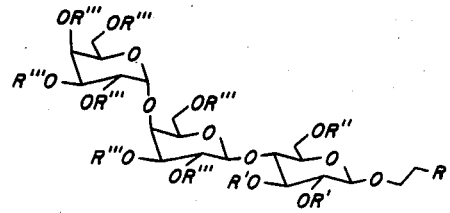
Figure 7:
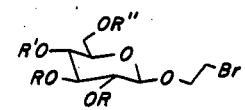
Figure 7:
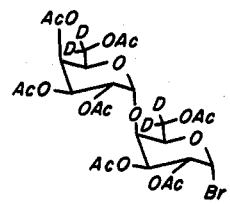
Figure 7:
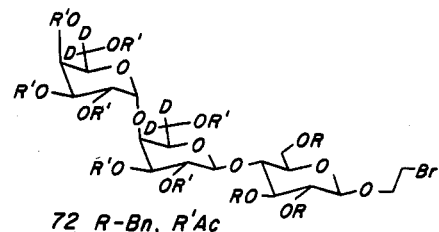
Figure 7:
Figure 7:
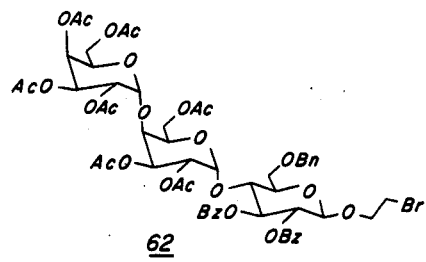

As mentioned above, well defined oligosaccharides an their derivatives are useful in medicinal and biochemical research. Accordingly, we have prepared, using the inventive concept, a series of these compounds (see Table 1, 4, and 5 and FIGS. 1–9) for use in different agglutination tests and for the preparation of carbohydrate-specific antibodies. The examples given cover derivatives of mono-, di-, tri-, and tetra-saccharides of biological significance. This is exemplified below for two trisaccharides of the P blood-group system and for a tetrasaccharide that is excreted in human urine in connection with certain physical conditions:

The P$^k$-antigen (see FIG. 7)

Carbohydrates of the P blood-group system[19] have been suggested to be specific receptors for uropathogenic E. coli bacteria[20]. Synthetic studies on these and related compounds have lead to the preparation of glycosides of the oligosaccharides α-D-Gal-(1→4)-β-D-Gal[21], α-D-Gal-(1→4)-β-D-Gal-(1→4)-β-D-Glc[22], α-D-Gal-(1→4)-β-D-Gal-(1→4)-β-D-GlcNAc[23] and β-D-GalNAc-(1→3)-α-D-Gal-(1→4)-β-D-Gal-(1→4)-β-D-Glc[24].

We now describe (see FIG. 7) an alternative route, starting from the acetobromo sugar 49 and the 2-bromoethyl glucoside 54, leading to a common 2-bromoethyl glycoside precursor (59) that was used for the preparation of spacer-arm, lipid and ethyl glycosides of the p$^k$-antigen.

Specifically deuterated derivatives of carbohydrates can be used to simplify interpretations of mass- and $^1$H-NMR spectra, and as labeled compounds for investigations of dynamic properties by $^2$H-NMR techniques of for example neo-glycolipids in cell membranes. We have prepared a tetra-deuterated analog to 59 (74) from 71 and 54, following the same route as for the preparation of 59 (vide infra).

Figure 8:
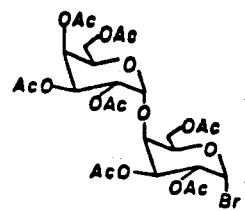
FIG. 8 shows a total synthesis of the P$_1$-antigen.
Figure 8:
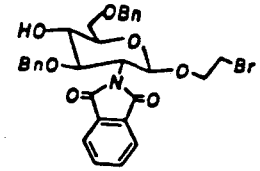
Figure 8:
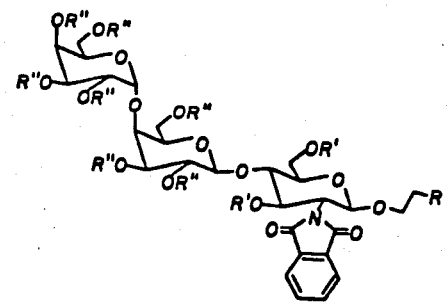
Figure 8:
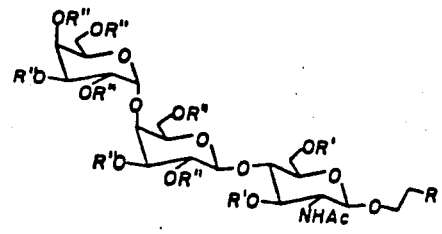

The P$_1$-antigen (see FIG. 8)

We also describe a synthesis of the terminal trisaccharide portion of the P$_1$-antigen in the form of its 2-bromoethyl glycoside (78) followed by transformations into spacer-arm, lipid and ethyl glycosides as well as into neo-glycoproteins. The synthesis is based on the acetobromo sugar 49 which is readily available from pectin via enzymatic hydrolysis-borohydride reduction sequence[21g].

Figure 9:
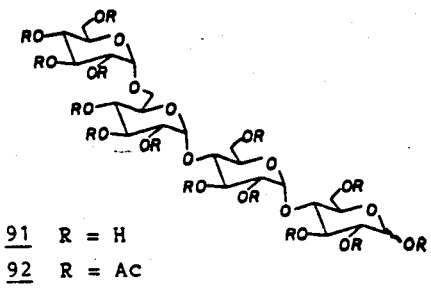
FIG. 9 shows a total synthesis of a glucose tetrasaccharide found in human urine.
Figure 9:
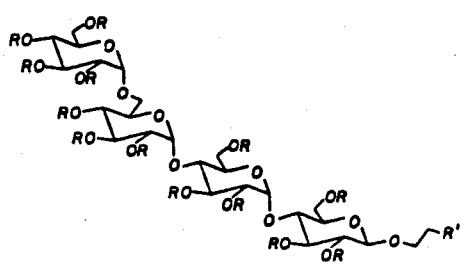

The urinary glucose tetrasaccharide (see FIG. 9)

The tetrasaccharide α-D-Glcp-(1→6)-α-D-Glcp-(1→4)-α-D-Glcp-(1→4) -D-Glc (91) is normally excreted in human urine[25]. Increased excretion is observed in patients with type II and type III glycogenosis[26], in Duchenne muscular dystrophy[27] and during normal pregnancy[28]. Rapid detection of 91 can be done by radioimmunoassay[29] using antibodies raised against a neo-glycoprotein that was obtained by reductive amination of 91 (isolated from urine[25]) with p-aminophenylethylamine followed by coupling to key-hole limpet haemocyanine (KLH) and bovine serum albumin (BSA).

Since reductive amination transforms the reducing end of 91 into a glucitol derivative, it became of interest to prepare a spacer-arm glycoside with all four glucose units intact. We describe the preparation of 91 and its transformation, via the corresponding 2-bromoethyl glycoside 93, into different derivatives (94–102) of value for the preparation and evaluation of antibodies.

Preparation and characterization of 2-bromoethyl glycosides

The compounds can be prepared by standard methods for glycoside synthesis (cf ref. 15) starting from acetylated of benzylated 1-bromo sugars. For simple sugars (monosaccharides and a few disaccharides) it turns out that a direct glycosidation of the per-O-acetylated sugar with 2-bromoethanol, using boron-trifluoride etherate in methylene chloride, is a very expedient process that normally permits the isolation of the pure 1,2-trans glycoside in crystalline form, directly from the crude reaction mixture (see Examples and Table 1). We recently reported this use of $BF_3$-etherate for the synthesis of 2,2,2-trichloroethyl glycosides[30]. The same Lewis acid has been used for anomerization purposes[31] and for the preparation of a variety of thioglycosides[32].

Figure 1:
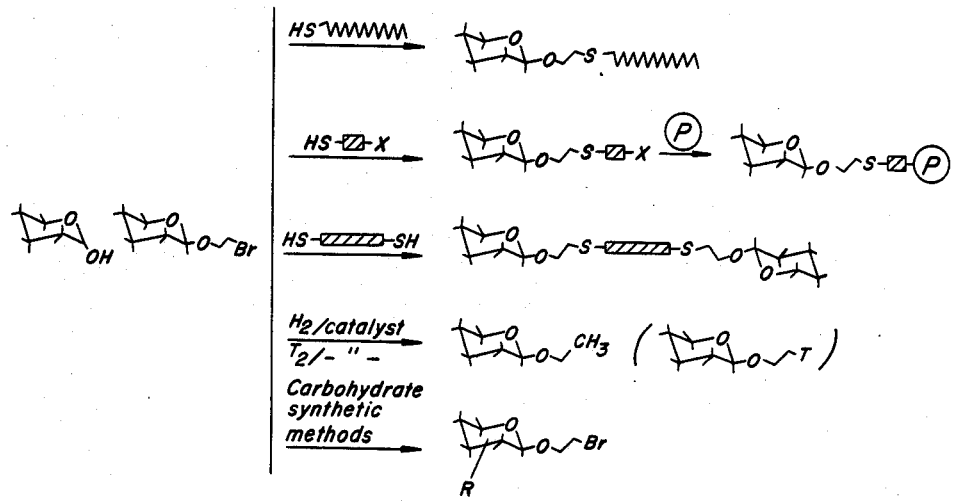
FIG. 1 shows an over-view of principal applications of 2-bromoethyl glycosides.
Figure 2:
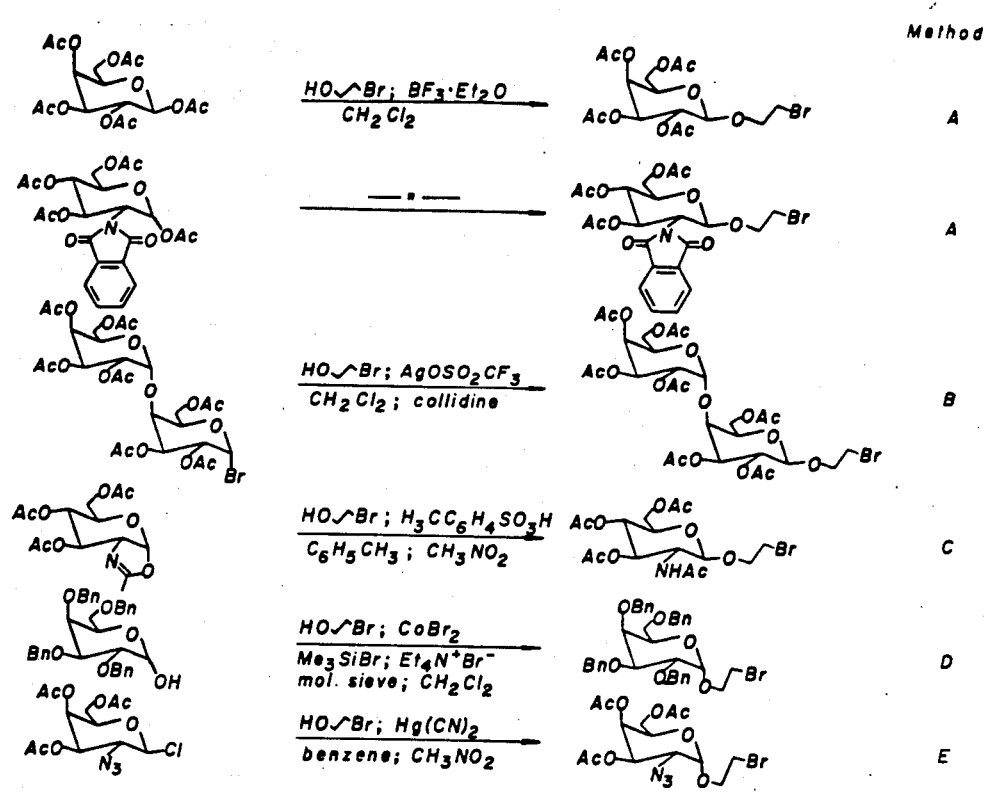
FIG. 2 shows examples of 2-bromoethyl glycoside syntheses.

Because of the difficulty of separating anomeric pairs of higher oligosaccharides, it is in this case normally advisable to use more stereoselective methods of glycoside synthesis[15] than the $BF_3$-etherate method mentioned above. We have for example been able to synthesize 1,2-trans 2-bromoethyl glycosides using the silver trifluoromethanesulfonate method[33] and 1,2-cis glycosides by a variation[34] of the quaternary ammonium bromide method devised by Lemieux[35], all in good yield and stereoselectivity (cf Table 1). In addition, 2-bromoethyl 3,4,6-tri-O-acetyl-2-acetamido-2-deoxy-$\beta$-D-glucopyranoside (8) was obtained by the oxazoline method[36] (Table 1). FIG. 2 as appended shows a summary of the different methods.

Furthermore, four different 2-bromoethyl glycosides (blood-group H disaccharide, blood-group $P^k$ and $P_1$ trisaccharides, urinary glucose tetrasaccharide) will be described below under the heading "The 2-bromoethyl group in standard carbohydrate synthetic chemistry".

The physical and chemical properties of 2-bromoethyl glycosides, as well as their simple preparation, make these compounds attractive intermediates for the preparation of neo-glycoconjugates. The monosaccharide glycosides crystallize very well, which makes the preparation of anomerically pure compounds simple; the chemical reactivity of these glycosides will be dealt with below.

Figure 3:
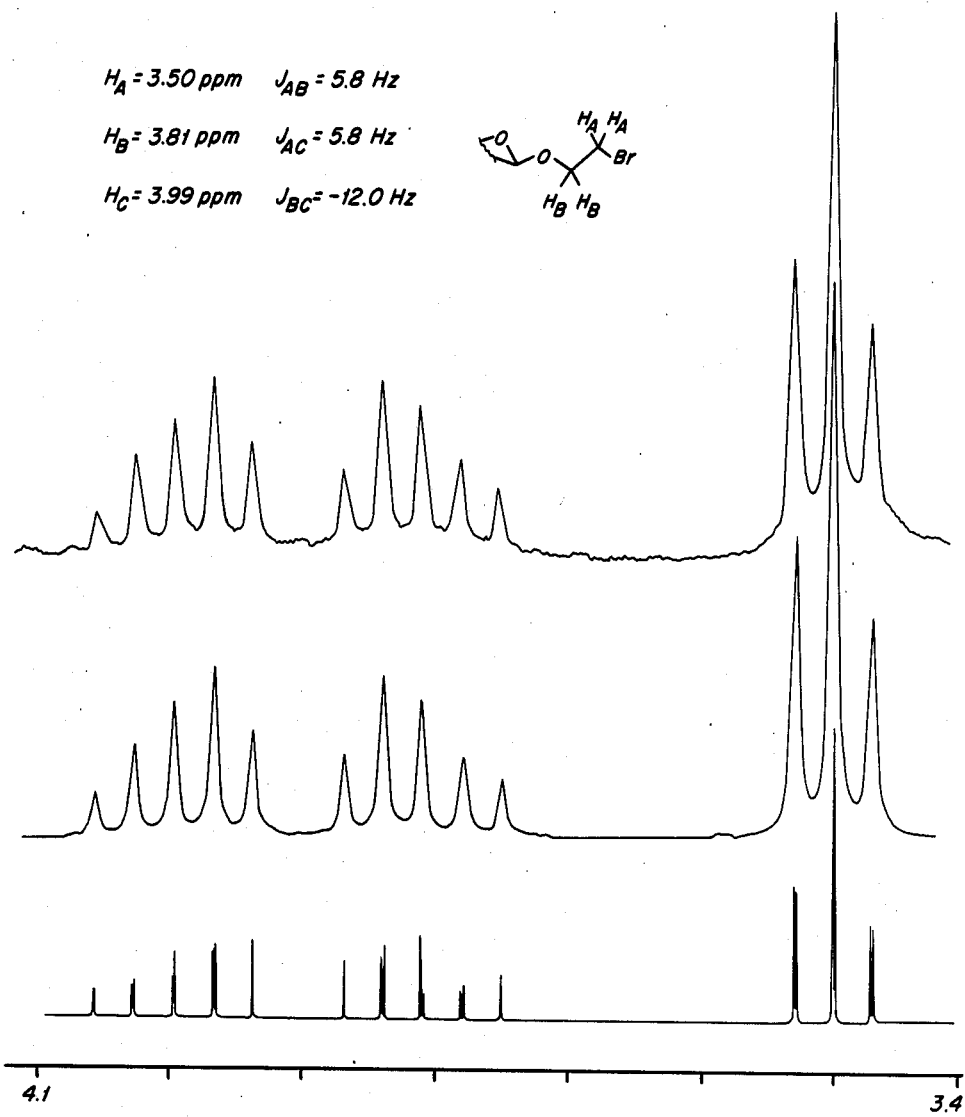
FIG. 3 shows typical examples of H-NMR spectra of 2-bromoethyl glycosides.

The $^{13}$C-NMR spectra of the different 2-bromoethyl glycosides show just a slight variation in the chemical shift of the bromoethyl group carbon signals (cf Table 2). The $^1$H-NMR spectra (Table 3) are on the other hand sometimes difficult to analyze because the complex spin-pattern of the bromoethyl group can obscure some of the sugar ring proton signals. FIG. 3 as appended depicts a typical spectrum (bromoethyl group part) together with a computer simulation. In this special case there was no interference from the sugar ring protons.

As a further illustration, three other $\omega$-bromoalkyl glycosides were prepared and characterized: compounds 16, 17, and 18 (vide infra). These compounds were all prepared according to Method A as defined in Table 1 and in the Examples, using the appropriate $\omega$-bromoalkyl alcohol. Product data and yields for compounds 16–18 are given in Table 4.

Preparation of complete spacer-arm glycosides

The 2-bromoethyl glycosides can conceivably be elaborated into a vast array of compounds that are suited for coupling to proteins and other macromolecular entities. It is however evident from the literature[16], that two different functional groups can master virtually all cases of covalent attachment of the glycoside to the carrier molecule. Accordingly, we decided to use terminal amino-(in the form of a para-substituted aniline) and carboxyl group derivatives for coupling (by amide bond formation) to carrier carboxyl and amino groups, respectively. In addition, non-covalent bonding (so called hydrophobic bonding) is known to occur between for example long aliphatic chains and lipid cellular membranes. Spacer-arms of this type thus makes coating of biological membranes by well-defined oligosaccharides possible.

Table 5 shows the model spacer-arm glycosides (see Examples for preparation). The thiols are all commercially available compounds. Aliphatic thiol esters with other chain-lengths can be prepared by standard synthetic methods[38] using u-hydroxy esters (easily available from alicyclic ketones by the Baeyer-Villiger reaction followed by alcoholysis[39]), thus allowing great variability in the length of the spacer-arm. Variation of the fatty alkyl chain-length and branching can lead to synthetic glycolipids that bind into cellular membranes or form liposomes and other aggregates in many different ways.

Primary alkyl bromides are well-known alkylating agents and thiols (especially thiolates) are nucleophiles of high repute. It is possible to perform the reaction with protected sugars, such as per-O-acetates, since this adds flexibility in the choice of chromatographic methods for final purification. In the "anhydrous" method (G in Table 5) deacetylation before work-up and purification of the reaction gives good yields of the desired products.

The "aqueous" method (F in Table 5) is selective and gives the desired sulfides in high yield without any deacetylation or other unwanted side reactions. Table 5 shows some spacer-arm glycosides that are ready for deprotection and/or chemical activation that finally makes them suited for coupling to carrier molecules.

Furthermore, four different spacer-arm glycosides will be described below under the heading "The 2-bromoethyl group in standard carbohydrate synthetic chemistry".

Preparation of complete neo-glycoconjugates

The present invention makes it possible to produce neo-glycoconjugates where the carbohydrate part is well characterized both regio- and stereospecifically. Furthermore, by employing the same intermediate 2-bromoethyl glycosides, it is possible to prepare oligosaccharide glycosides that are well suited for the study of inhibition of agglutination reactions between for example erythrocytes and antibodies raised against the neo-glycoconjugates mentioned above. Preparation of these inhibitors is described below.

Much ingenuity has been spent on the problem of attaching spacer-arm glycosides to macromolecules under semi-physiological conditions[16,40]. We have applied well-established reaction conditions for the attachment of two model compounds to proteins (see FIG. 4). The simple spacer-arm galactoside 28 was coupled to bovine serum albumin (BSA) by the method developed by Inman[41] and Lemieux[40] and coworkers in order to investigate the degree of binding (number of hapten molecules per molecule of BSA). This was done by the wellknown phenol/sulfuric acid method[42] but also with a more unconventional method. The spacer-arm used in this work contains a sulfur atom which makes it possible to determine the amount of covalently bound glycoside by a differential elemental (combustion) analysis of the amount of sulfur added to the protein. Both methods reveal that 35 galactose units were bound to each protein molecule. The highest possible degree of binding is 57 (the number of terminal amino groups in lysin residues of BSA).

The "aniline" spacer-arm was used to couple the di-galactoside 27 by the thio-phosgene method[43] to the protein BSA and key-hole limpet haemocyanine (KLH). The degree of coupling was determined by the anthrone method[44] which indicated a binding of 37 and 435 hapten molecules per protein molecule. The neo-glycoproteins thus produced were used as antigens in order to raise monoclonal antibodies against the di-galactose structure.

In addition to the preparation of neo-glycoproteins, the present spacer-arm glycosides are well suited for coupling to particles (e.g. glass, latex, silica gel and cross-linked polysaccharides) which could be used for affinity chromatographic purification of lectin-like materials and other molecules with carbohydrate specificity. Furthermore, small, non-sedimenting particles with covalently bound oligosaccharides should find applications as stable and well-defined substitutes for erythrocytes in agglutination studies with antibodies and bacteria.

Additional neo-glycoproteins will be described below under the heading "The 2-bromoethyl group in standard carbohydrate synthetic chemistry".

Preparation of simple glycosides, suitable as agglutination inhibitors

Evaluation of carbohydrate specific agglutination reactions is performed by the use of well-defined inhibitors that in a more or less specific way can prevent the formation of the agglutination precipitate or even dissolve it after its formation. The inhibitors normally used are either free mono- or oligosaccharides or simple (e.g. methyl and ethyl) glycosides. The latter have the added advantage of a well-defined anomeric configuration.

The 2-bromoethyl glycosides of this invention make it possible to prepare ethyl glycosides (by a simple hydrogenolysis reaction) from the same intermediates as were used for the preparation of the complete spacer-arm glycosides. In this way one avoids otherwise necessary doubling of the total synthetic effort. Radioactively labeled glycosides can be prepared by simply exchanging the hydrogen gas by tritium.

Figure 5:
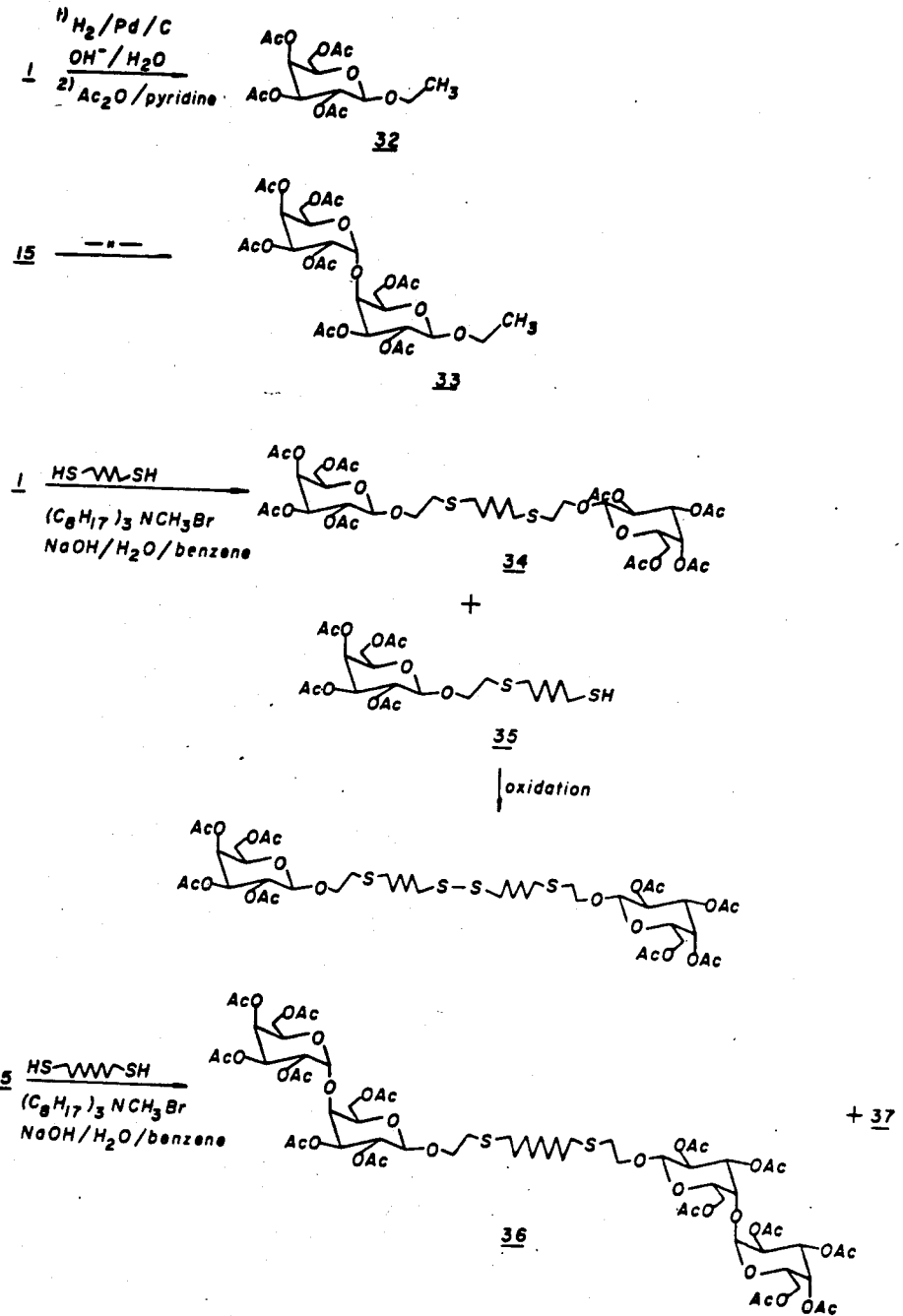
FIG. 5 shows some examples of the preparation of agglutination inhibitor glycosides.
Figure 6:
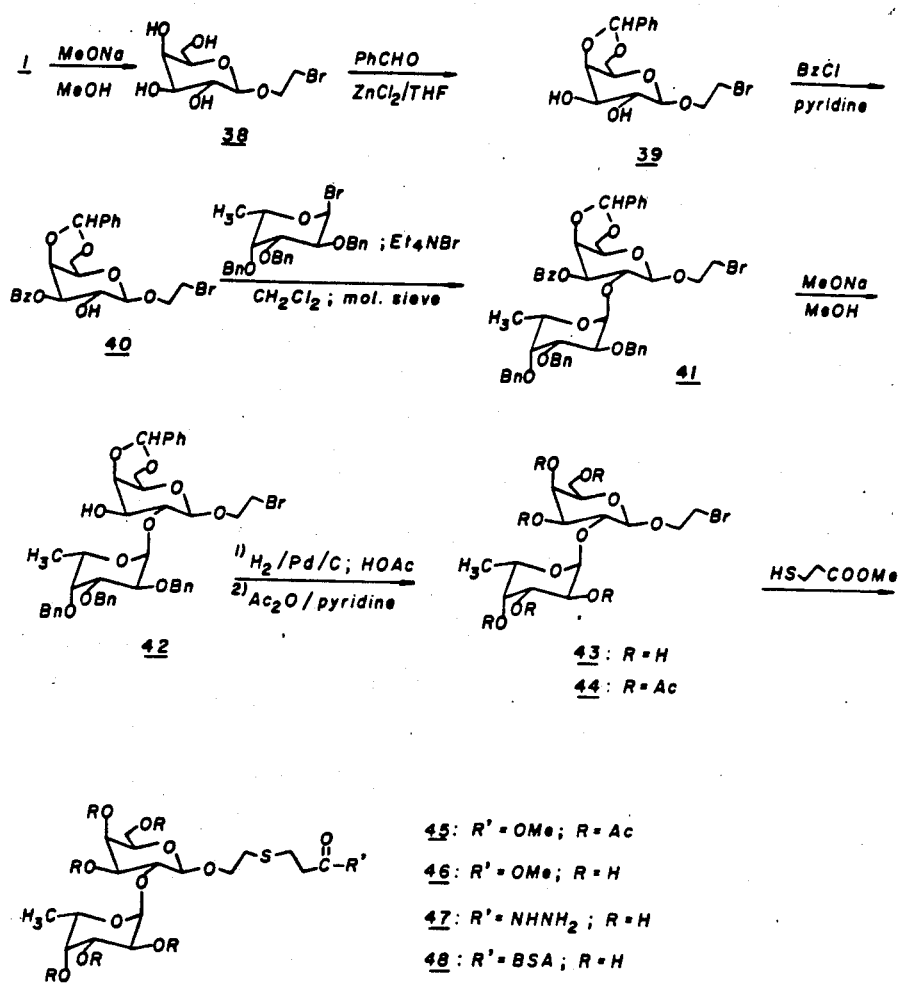
FIG. 6 shows a total synthesis of the blood-group H of specific glycosides.

Replacement of the functionalized thiols that were used for spacer-arm synthesis by di-thiols makes it possible to prepare bi-dentate inhibitor glycosides, and tri-, tetra-etc. thiols should give tri-, tetra- etc. dentate inhibitors by analogous procedures. Variation of the di-thiol chain-length makes it possible to prepare a series of inhibitors where the distance between the sugar residue can be varied almost at will. For the preparation of inhibitors with very long interconnecting chains, it is possible to change the ratio between the 2-bromoethyl glycoside and the di-thiol so that mainly the intermediate, thiol-terminated spacer-arm glycoside is formed in the reaction (see Examples). Standard oxidative di-sulfide formation[45] can then be used for the formation of the bi-dentate inhibitor compound. The different types of inhibitor glycosides, that have been prepared from 2-bromoethyl glycosides, are shown in FIG. 5.

Additional ethyl glycosides will be described below under the heading "The 2-bromoethyl group in standard carbohydrate synthetic chemistry".

The 2-bromoethyl group in standard carbohydrate synthetic chemistry

As shown above, the 2-bromoethyl glycosides are very versatile compounds that can be used for the preparation of many kinds of biologically interesting carbohydrate derivatives. The 2-bromoethyl group is also compatible with most of the synthetic reaction that are used in carbohydrate chemistry. As an illustration, we include here a total synthesis (FIG. 6) of the H blood-group specific disaccharide in the 2-bromoethyl $\beta$glycoside form (43) and its further coupling to BSA (48). All these reactions can be performed without any unwanted interference from the bromoethyl aglycon. However, the hydrogenolytic cleavage of the benzyl and benzylidene groups deserves some additional comments: In the preparation of the ethyl glycosides (FIG. 5), the bromine atom was cleaved off by hydrogen under basic conditions whereas the hydrogenolysis reaction shown in FIG. 6, was performed in acetic acid; acidic hydrolysis conditions leave the 2-bromoethyl group intact.

The 2-bromoethyl glycoside 44 was reacted with methyl 3-mercaptopropionate (cf. Table 5 and Examples) to give the spacer-arm glycoside 45. This compound was finally coupled (via the hydrazide 47) to bovine serum albumin to give the complete semi-synthetic antigen 48. The degree of binding was 47.

In addition, three other products ($P^k$ and $P_1$ antigens and a glucose-containing tetrasaccharide found in human urine) have been prepared by utilization of the different reaction sequences described above.

Synthesis of spacer-arm, lipid and ethyl glycosides of the trisaccharide portion of the blood-group $P^k$ antigen.

Preparation of neo-glycoproteins (see FIG. 7)

2-Bromoethyl 2,3,4,6-tetra-O-acetyl-$\beta$-D-glucopyranoside (50) was treated with methanolic sodium methoxide and the deacetylated product in N,N-dimethylformamide was immediately added to a mixture of zinc-II-chloride and benzaldehyde[46] to give 73% of 51. Treatment with benzyl bromide under phase-transfer catalysis conditions gave crystalline 52 and 53 in 80% and 20% yield, respectively. Treatment[47] of 52 with sodium cyanoborohydride gave 2-bromoethyl 2,3,6-tri-O-benzyl-$\beta$-D-glucopyranoside (54) in 59% yield. Treatment of 51 with benzoyl chloride in pyridine gave 55 in 86% yield. Reduction of the benzylidene group as above[47] gave 2-bromoethyl 2,3-di-O-benzoyl-6-O-benzyl-$\beta$-D-glucopyranoside (56) in 65% yield.

The partly protected 2-bromoethyl glycosides 54 and 56 were used as aglycons in silver triflate-promoted glycosylations with 2,3,6-tri-O-acetyl-4-O-(2,3,4,6-tetra-O-acetyl-α-D-galactopyranosyl)-α-D-galactopyranosyl bromide (49). With 54, the β-glycoside 57 (and a small amount of α-glycoside; vide infra) was formed in 55% yield, whereas with 56 a ~3:1 αβ-mixture (62 and 60) was formed. Catalytic hydrogenation of 60 gave 61 in 100% yield which on treatment with methanolic sodium methoxide and finally reacetylation gave 59.

Catalytic hydrogenation of recrystallized 57 in acetic acid gave a quantitative yield of 58 (basic reaction conditions leave benzyl groups intact whereas the use of acidic conditions permits the removal of such protecting groups without affecting the 2-bromoethyl aglycon). Acetylation gave 69% yield of the 2-bromoethyl glycoside 59, which is central for the preparation of the remaining compounds (63–70). The tetradeuterated compound 74 was prepared by the same method from 71 and 54 via 72 and 73.

Nucleophilic displacement of bromide ion from 59, using methyl 3-mercaptopropionate[48] or octadecylthiol in N,N-dimethylformamide containing cesium carbonate, gave the spacer-arm glycoside 63 and the neo-glycolipid 65 both in 87% yield. Deacetylation of 63 and 65 gave 64 and 66 in 97% and 88% yield. The glycoside 64 was coupled to bovine serum albumin and key-kole limpet haemocyanin, using a modification of the Inman-Lemieux procedure[40,41] with dimethylsulfoxide as solvent instead of N,N-dimethylformamide, thus furnishing the neo-glycoproteins 69 and 70, respectively. The degree of binding was 14 and 480, respectively. Catalytic hydrogenation of 59 under basic conditions, followed by acetylation of the product, gave 67 in 62% yield. Deacetylation of 67 gave a quantitative yield of 68. The use of crude 59 in the latter reaction sequence gave a small amount (<5%) of α-glycoside (TLC and $^1$H-NMR) that had been formed in the reaction of 54 with 49. The structure of 68 was confirmed by sugar[49] and methylation[50] analysis.

Synthesis of spacer-arm, lipid and ethyl glycosides of the terminal trisaccharide portion of the blood-group P₁-antigen.

Preparation of neo-glycoproteins (see FIG. 8)

The partly protected 2-bromoethyl glycoside[75] was glycosylated with acetobromo sugar 49[21g], using silver triflate and tetramethyl urea in dichloromethane, to give the trisaccharide glycoside 76 (41%). The benzyl protecting groups of 76 were removed by hydrogenolysis in acetic acid, to give 77 (92%). Acetylation of 77 gave the key intermediate 78 (72%), which was used for the preparation of 79, 80 and 87. Treatment of 78 with methyl 3-mercaptopropionate or octadecanethiol in N,N-dimethylformamide, using cesium carbonate as promoter, gave spacer-arm glycoside 79 (94%) and neoglycolipid 80 (91%), respectively. Hydrogenation of 78 under basic reaction conditions, followed by N-deprotection and reacetylation gave the ethyl glycoside 87 (28%). N-Deprotection and reacetylation of 79 and 80 gave 81 (50%) and 83 (52%), respectively. O-Deacetylation of 81, 83, and 87 gave spacer-arm glycoside 82 (90%), neo-glycolipid 84 (87%) and ethyl glycoside 88 (60%), respectively. The latter was also prepared from 76 via 85 and 86.

The spacer-arm glycoside 82 was coupled to the proteins bovine serum albumin (BSA) and key-hole limpet haemocyanin (KLH), which gave the neo-glycoproteins 89 and 90. The degree of binding was 17 and 420, respectively.

Synthesis from pullulan of spacer-arm, lipid and ethyl glycosides of a tetrasaccharide found in human urine Preparation of neo-glycoproteins (see FIG. 9)

Enzymic hydrolysis[51] (β-amylase and pullulanase) of pullulan[52], followed by acetylation of the crude product and silica gel chromatography gave 92 in 12% over-all yield (αβ-ratio, ca 1:1). The structure of 91 was confirmed by methylation analysis[26] and comparison of the MS-data with those of the authentic material[26]. Further structural support was obtained by NMR analysis of 92–100 (see Examples). This also confirmed the anomeric configurations in 91 as proposed by Hallgren et al[25].

The 2-bromoethyl glycoside 93 was prepared by boron-trifluoride etherate induced glycosidation[30] of the αβ-mixture 92 with 2-bromoethanol in dichloromethane. This gave the β-glycoside; the α-anomer could not be detected in the reaction mixture. Treatment of 93 with methyl 3-mercaptopropionate, methyl 11-mercaptoundecanoate (105), octadecylthiol, and hydrogen-Pd/C gave spacer-arm glycosides 94 and 95, neo-glycolipid 96 and ethyl glycoside 97 respectively. Deacetylation of 94, 95, and 96 gave 98, 99, and 100.

The neo-glycoproteins 101 and 102 were prepared by coupling of 98 to BSA and KLH. A modification of the Inman[41]-Lemieux[40]-technique was used (see Examples), where N,N-dimethylformamide was substituted by dimethylsulfoxide, due to the low solubility of 98 in the former solvent. The degree of binding (number of hapten molecules per molecule of protein) of 98 to BSA and KLH was 20 and 245, respectively.

The invention will be further illustrated by specific examples of a non-limiting character. In these examples melting points were recorded on a calibrated Kofler hot stage or on a Reichert melting point microscope. Optical rotations were recorded on a Perkin Elmer 241 Polarimeter. NMR spectra were recorded on a Varian XL-200 spectrometer. Solvent removal was done on a rotary evaporator followed by oil-pump evaporation below 0.1 Torr.

EXAMPLES 1–15

Preparation of 2-bromoethyl glycosides (cf. FIG. 2 and Table 1)

Reactions were monitored by thin layer chromatography (TLC) using the technique for selective visualization[30] of sugar per-O-acetates and glycosides. Yields, melting points and optical rotations for the 2-bromoethyl glycosides (1–15) are shown in Table 1 and $^{13}$C- and $^1$H-NMR spectra are shown in Table 2 and 3, respectively.

Method A (cf. ref. 30)

The sugar per-O-acetate (5 mmol) and 2-bromoethanol (6 mmol) were dissolved in dry methylene chloride (10 ml) and cooled (ice bath). Borontrifluoride etherate (25 mmol) was added dropwise (ca 15 min). The ice bath was removed after 1 h and the reaction was continued at room temperature until the starting material had been consumed (TLC; 2–20 h).

Glycosides with the 1,2-trans configuration are formed first. At the end of the reaction period, a small amount of the 1,2-cis glycoside is usually formed, probably by an anomerization reaction[31]. In addition, a long reaction time normally gives minor amounts of deacetylated compounds. The formation of these side products can be minimized by a careful monitoring of the reaction.

The reaction mixture was poured into ice water (10 ml) and the phases were separated. The water phase was extracted with methylene chloride (5 ml) and the combined methylene chloride solutions were washed (water, sodium hydrogen carbonate, water) and dried (sodium sulfate). Filtration and evaporation gave syrup that was dissolved in warm ether or ethyl acetate. Addition of petroleum ether or isooctane gave the crystalline (where applicable; see Table 1) per-O-acetylated 2-bromoethyl glycoside. Yield: see Table 1. Preparative chromatography of the mother liquor, raised the yield considerably.

Method B

2-Bromoethyl 2,3,6-tri-O-acetyl-4-O-(2,3,4,6-tetra-O-acetyl-α-D-galactopyranosyl)-β-D-galactopyranoside (15)

A solution of hydrogen bromide in acetic acid (45%, 30 ml) was added dropwise (ca 25 min) to a solution of 1,2,3,6-tetra-O-acetyl-4-O-(2,3,4,6-tetra-O-acetyl-α-D-galactopyranosyl)-α-D- galactopyranose[21g] (20.0 g; 29.5 mmol) in acetic acid/acetic anhydride (2/1; 20 ml) at 0° C. The reaction mixture was kept at 0° C. for 4 h and then at room temperature for 1.5 h and finally it was diluted with methylene chloride (400 ml) and poured into an ice cold, saturated sodium hydrogen carbonate solution (400 ml). The aqueous phase was extracted with methylene chloride (50 ml) and the combined extracts were washed with another portion of bicarbonate solution (300 ml) and dried (sodium sulfate). Filtration and evaporation gave 1-bromo-2,3,6-tri-O-acetyl-4-O-(2,3,4,6-tetra-O-acetyl-D-galactopyranosyl)-α-D-galactopyranose (49, 20.8 g; pure by TLC) as a crystalline mass. Recrystallization from ethyl acetate-ether gave an analytical sample; Mp 97°–99°; $[\alpha]_D^{21}+219°$ (c 0.8; CHCl$_3$); $^1$H-NMR (CDCl$_3$; TMS) δ 6.73 (d, 1H, $J_{1,2}$=4 Hz, H1), 5.55 (dd, 1H, J=1.5 Hz, J=3 Hz, H4′), 5.36 (dd, 1H, $J_{2',3'}$=11 Hz, $J_{3',4'}$=3 Hz, H3′), 5.29 (dd, 1H, $J_{2,3}$=11 Hz, $J_{3,4}$=2.5 Hz, H3), 5.25 (dd, 1H, $J_{1',2'}$=3.5 Hz, $J_{2',3'}$=11 Hz, H2′) 5.10 (dd, 1H, $J_{1,2}$=4 Hz, $J_{2,3}$=11 Hz, H2), 5.01 (d, 1H, $J_{1',2'}$=3.5 Hz, H1′), 4.49 (dt, 1H, $J_{4',5'}$=1.5 Hz, $J_{5',6'}$=7 Hz, H5′), 4.40–4.05 (6H), 2.15 2.13, 2.12 2.12 2.09, 2.03, 2,00 (s, 3H each, CH$_3$CO) ppm. $^{13}$C-NMR (CDCl$_3$; TMS) δ 170.4, 170.3, 170.2, 170.1, 169.9, 169,7 (CO), 99.1 (Cl′), 88.7 (Cl), 76.3, 72.7, 69.9, 68.0, 67.7, 67.6, 67.3, 67.2 (CHOAc), 61.5, 60.7 (C6, C6′), 20.9, 20.7, 20.6 (CH$_3$-CO) ppm.

A solution of the crude acetobromo sugar 49 (20.5 g; 29.3 mmol) in dry methylene chloride (100 ml) was added dropwise (ca 20 min) to a cold (−78°) solution of silver trifluoromethanesulfonate (nonpurified, commercial material; 10.3 g; 40 mmol), 2,4,6-tri-methylpyridine (3.6 g; 30 mmol) and 2-bromoethanol (17.5 g; 140 mmol) in methylene chloride (250 ml) under nitrogen. The reaction mixture was stirred in the dark for 23 h during which time it had reached room temperature. The yellowish-white precipitate, that had formed, was removed and the resulting colorless solution was washed consecutively with 1M hydrochloric acid, water, saturated sodium hydrogen carbonate solution and water. Drying (sodium sulfate), filtration and evaporation gave a residue which crystallized spontaneously. Recrystallization from ethyl acetate, followed by evaporation of the mother liquor and recrystallization from methanol, gave a total of 16.6 g (77%) of the title compound 15. Melting point and optical rotation are shown in Table 1 and the $^{13}$C- and $^1$H-NMR data are shown in Table 2 and 3 , respectively.

Method C

2-Bromoethyl 3,4,6-tri-O-acetyl-2-acetamido-2-deoxy-β-D-glucopyranoside (8)

Per-O-acetylated glucose oxazoline[53] (see FIG. 2; 4.62 g; 14.0 mmol), 2-bromoethanol (8.49 g; 67.9 mmol) and p-toluenesulfonic acid (81 mg) were dissolved in toluene and nitromethane (1/1; 80 ml). The solution was heated (110°) for ca 10 minutes and cooled. A TLC-analysis (SiO$_2$, toluene/ether/methanol 7/7/1) showed that all of the starting oxazoline had been consumed. Pyridine (20 drops) was added and the reaction mixture was evaporated to dryness. Preparative chromatography of the residue gave the title compound (8). Yield, melting point and optical rotation are shown in Table 1 and $^{13}$C- and $^1$H-NMR data are shown in Table 2 and 3, respectively.

Method D

2-Bromoethyl 2,3,4,6-tetra-O-benzyl-α-D-galactopyranoside (2)

Trimethylsilyl bromide (7.96 g, 6.78 ml. 52 mmol) was added with a syringe to a mixture of 2,3,4,6-tetra-O-benzyl-D-galactopyranose (28 g, 52 mmol), 2-bromoethanol (4.46 ml, 40.0 mmol), cobalt(II)bromide (11.4 g, 52.0 mmol), tetraethylammonium bromide (10.9 g, 52.0 mmol) and molecular sieves (4 Å, 41 g) in 138 ml of methylene chloride under nitrogen with protection from light. (The cobalt(II)chloride had been dried at 180°, 5×10$^{-3}$ mm Hg over night. ) The reaction mixture was stirred at room temperature over night and filtered. The residue was washed with 100 ml of methylene chloride. The filtrate was evaporated at reduced pressure to give 25.8 g of the crude product, which was chromatographed (SiO$_2$, isooctane:ethyl acetate 3:2) Fraction 1 was the pure title compound (6.0 g) and fraction 2 was a mixture of the anomers (α/β, 10.0 g) Total yield of glycosides 16 g (48%) (This procedure is a slight modification of that of Koto et al.[34]) $[\alpha]_D^{23}$= +30.5° (c 1.4, CHCl$_3$). $^1$H-NMR (CDCl$_3$, TMS) δ 7.30 (m, 20H, Ph), 4.97–4.42 (m, 9H), 4.0–3.8 (m, 6H), 3.52 (t, 4H, inter alia CH$_2$Br). $^{13}$C-NMR (CDCl, TMS) δ 103.3 (d, Cl, $J_{C-H}$=168 Hz), 84.2, 81.6, 80.2, 75.0 (C2–C5), 80.0, 78.7, 78.6, 78.5, 74.2, 73.5 (C6, benzylic CH$_2$ and aglycon O—CH$_2$), 35.5 (CH$_2$Br)

Method E

2-Bromoethyl 3,4,6-tri-O-acetyl-2-azido-2-deoxy-α-D-galactopyranoside (12)

From a mixture of benzene (30 ml) and nitromethane (30 ml), 30 ml of the solvent mixture was distilled off. The temperature of the remaining solvent mixture was adjusted to 60° C., whereafter 2-bromoethanol (0.355 ml, 5.00 mmol) was added followed by mercuric cyanide (1.26 g, 5.00 mmol) and 1-chloro 3,4,6-tri-O-acetyl-2-azido-2-deoxy-β-D-galactopyranose[54] (1.74 g, 4.98 mmol) dissolved in a few ml of benzene. The reaction mixture was stirred at 60° C. for 3 days, 100 ml of methylene chloride was then added and the organic solution was washed with water (3×25 ml). After drying (Na$_2$-

SO$_4$) and removal of the solvent in vacuo the residue, 1.90 g, was chromatographed (SiO$_2$, isooctane:ethyl acetate 2:1) to give 1-chloro-3,4,6-tri-O-acetyl-2-azido-2-deoxy-α-D-galactopyranose (350 mg) and a second fraction (340 mg) containing both anomers of 12. This fraction was chromatographed (SiO$_2$, 1,1,2-trichlorotrifluoroethane:ether 55:15) to give the pure title compound 12 (165 mg, 8%) as a syrup. Optical rotation is shown in Table 1 and the $^1$H- and $^{13}$C-NMR data are shown in Table 3 and 2, respectively.

EXAMPLES 16–18

Compounds 16–18 were prepared form D-galactosepentaacetate, D-glucosepentaacetate and 2-deoxy-2-phtalimido-D-glucosetetraacetate, respectively, by glycosidation according to method A above and using 3-bromopropanol and 11-bromoundecanol as glycosylating agents. Yields and physical data are given in Table 4.

EXAMPLES 19–27

Preparation of complete spacer-arm glycosides (cf. Table 5)

Compounds 19–23 were prepared by method F and compounds 24–27 by method G; vide infra.

Method F

2-(2-Methoxycarbonylethylthio)ethyl 2,3,4,6-tetra-O-acetyl-β-D-galactopyranoside (19)

2-Bromoethyl 2,3,4,6-tetra-O-acetyl-β-D-galactopyranoside (1) (1.76 g; 3.90 nmol), methyl 3-mercaptopropionate[55] (1.0 ml; 9.2 mmol), methyltrioctylammonium chloride (ca 10 mg) and sodium hydroxide (0.36 g; 9.0 mmol) were dissolved in benzene (5 ml) and water (5 ml). The reaction mixture was stirred vigorously at room temperature. The reaction was half-way after ca 40 minutes (TLC: SiO$_2$, ethyl acetate:isooctane 2:1) but after this time it slowed down considerably. The reaction was continued over night which gave an almost complete consumption of the starting material. It should be noted that no deacetylation occurred under these reaction conditions. The aqueous phase was extracted with benzene and the combined benzene solutions were washed once with water. Drying, evaporation and chromatography (SiO$_2$, ethyl acetate:isooctane 1:1) gave the title compound (19) as a syrup that crystallized slowly. Yield 1.41 g (73%) Recrystallization from abs. ethanol gave an analytical sample: mp 81°–82°; $[α]_D^{24}$ −10.5° (c 1.0; CDCl$_3$): $^1$H-NMR (CDCl$_3$, TMS) δ 5.42 (d, 1H, J$_{3,4}$=3.5 Hz, H4), 5.24 (dd, 1H, J$_{1,2}$=7.8 Hz, J$_{2,3}$=10.5 Hz, H2), 5.05 (dd, 1H, H3), 4.54 (d, 1H, H1), 3.65–4.26 (m, 5H, H5, H6, O—CH$_2$—CH$_2$), 3.72 (s, 3H, CH$_3$), 2.59–2.88 (m, 6H, S—CH$_2$, CH$_2$—CO), 2.17, 2.09, 2.06, 2.00 (s, 3H each, CH$_3$CO) ppm. $^{13}$C-NMR (CDCl$_3$, TMS) δ 172.2, 170.4, 170.2, 170.1, 169.5 (CO), 101.3 (C1), 70.9, 70.8, 69.6, 68,7, 67.0 (C2–C5, O—CH$_2$), 61.3 (C6), 51.8 (OCH$_3$), 34.7, 31.5, 27.4 (CH$_2$—S, CH$_2$CO), 20.8, 20.7, 20.6 (CH$_3$CO) ppm.

2-(2-Methoxycarbonylethylthio)ethyl 2,3,6-tri-O-acetyl-4-O-(2,3,4,6-tetra-O-acetyl-α-D-galactopyranosyl)-β-D-galactopyranoside (22)

2-Bromoethyl 2,3,6-tri-O-acetyl-4-O-(2,3,4,6-tetra-O-acetyl-α-D-galactopyranosyl)-β-D-galactopyranoside (15) (251 mg; 0.338 mmol), methyl 3-mercaptopropionate (38 μl; 0.35 mmol) methyltrioctylammonium chloride (ca 10 mg) and cesium carbonate (114 mg; 0.35 mmol) were dissolved in benzene (0.5 ml) and water (0.5 ml). The reaction mixture was stirred (magnet) over night and analyzed by TLC (SiO$_2$, ethyl acetate:isooctane 4:1; reaction ⅔ completed). Methyl 3-mercaptopropionate (ca 20 μl) was added and the reaction mixture was stirred for 24 h (TLC showed complete reaction). The phases were separated, the water phase was extracted twice with methylene chloride and the combined organic phases were dried (sodium sulfate) which gave a yellow to green solution. Evaporation gave a syrup which was chromatographed (SiO$_2$, ethyl acetate:isooctane 2:1) to give the title compound (22) as a syrup. Yield: 211 mg (80%). $[α]_D^{23}$+70.0° (c 0.6; CHCl$_3$); $^1$H-NMR (CDCl$_3$, TMS) δ 5.57 (d, 1H, J$_{3',4'}$=3.0 Hz, H4'), 5.39 (dd, 1H, J$_{2',3'}$=11.0 Hz. H2'), 5.19 (dd, 1H, H3'), 5.17 (dd, 1H, J$_{2,3}$=11 Hz, H2), 5.00 (d, 1H, J$_{1',2'}$=4.0 Hz, H1'), 4.80 (dd, 1H, J$_{3,4}$=3.0 Hz, H3), 4.51 (d, 1H, J$_{1,2}$=8.0 Hz, H1), 3.70 (s, 3H, CH$_3$—O), 2.82, 2.75, 2.63 (t, 2H each, J=7 Hz, CH$_2$—S, CH$_2$—CO), 2.13, 2.11, 2.08, 2.08, 2.06, 2.04, 1.98 (s, 3H each, CH$_3$CO) ppm. $^{13}$C-NMR (CDCl$_3$, TMS) δ 172.3 (COOCH$_3$), 170.7, 170.6, 170.5, 170.4, 170.1, 169.8, 169.2 (CH$_3$CO), 101.1 (C1), 99.4 (C1'), 77.1, 72.7, 72.0, 68.6, 68.5, 67.9, 67.4, 67.1 (C2–C5, C2'–C5'), 69.5 (OCH$_2$), 62.0, 60.5 (C6, C6'), 51.8 (COOCH$_3$), 34.7, 31.4, 27.4 (CH$_2$S, CH$_2$—CO), 21.0, 20.7 (CH$_3$CO) ppm.

2-(p-Aminophenylthio)ethyl 2,3,4,6-tetra-O-acetyl-β-D-galactopyranoside (20)

$^{(i)}$2-Bromoethyl 2,3,4,6-tetra-O-acetyl-β-D-galactopyranoside (1) (2.05 g; 4.50 mmol), p-aminothiophenol (1.2 g; 9.6 mmol), methyltrioctylammonium chloride (20 mg) and sodium hydroxide (0.3 g; 7.5 mmol) were dissolved in benzene (5 ml) and water (5 ml) The reaction mixture was stirred vigorously for 9 h (TLC: SiO$_2$, ethyl acetate:isooctane 3:1) and worked up as above Chromatography (SiO$_2$, ethyl acetate:isooctane 2:1) gave the title compound (20) as an amorphous solid. Yield: 1.6 g (71%). $[α]_D^{21}$+7.7° (c 1.0; CHCl$_3$); $^1$H-NMR (CDCl$_3$, TMS) δ 7.25, 6.63 (ABq, 4H, J$_{AB}$=8.6 Hz, aromatic H), 5.39 (d, 1H, J$_{3,4}$=3.5 Hz, H4), 5.22 (dd, 1H, J$_{1,2}$=7.9 Hz, J$_{2,3}$=10.4 Hz, H2), 5.01 (dd, 1H, H3), 4.45 (d, 1H, H1), 2.92 (t, 1H, J=6.8 Hz, S—CH$_2$), 2.15, 2.08, 2.05, 2.00 (s, 3H each, CH$_3$CO) ppm. $^{13}$C-NMR (CDCl$_3$, TMS) δ 170.4, 170.3, 170.2, 169.5 (CO), 146.4, 134.5, 122.0, 115.6 (aromatic C), 101.5 (C1), 70.9, 70.6, 68.8, 68.7, 67.0 (C2–C5, O—CH$_2$), 61.2 (C6), 35.7 (S—CH$_2$), 20.9, 20.7, 20.6 (CH$_3$—CO) ppm.

$^{(ii)}$2-(p-Nitrophenylthio)ethyl 2,3,4,6-tetra-O-acetyl-β-D-galactopyranoside (25) (90 mg; 0.18 mmol) was hydrogenated over night (4 atm H$_2$ Pd/C 10%, 90 mg) in 75 ml of methanol which gave the title compound (20) in 58% yield after chromatography as above. 2-(Octylthio)ethyl 2,3,4,6-tetra-O-acetyl-β-D-galactopyranoside (21). 2-Bromoethyl 2,3,4,6-tetra-O-acetyl-β-D-galactopyranoside (1) (2.0 g; 4.4 mmol), octanethiol (0.7 g; 4.8 mmol), methyltrioctylammonium chloride (20 mg) and sodium hydroxide (0.3 g; 7.5 mmol) were dissolved in benzene (9 ml) and water (8 ml). The reaction mixture was stirred vigorously for 3 h (TLC: SiO$_2$, ethyl acetate:isooctane 3:1) and worked up as for compound 19 above. Chromatography (SiO$_2$, ethyl acetate:isooctane 2:1) gave the title compound (21) as a colorless oil. Yield: 1.6 g (70%). $[α]_D^{21}$−8.6° (c 1.2; CHCl$_3$); $^1$H-NMR (CDCl$_3$, TMS) δ 5.40 (dd, 1H, J$_{4,5}$=1.0 Hz, H4), 5.23 (dd, 1H, J$_{2,3}$=10.5 Hz, H2), 5.03 (dd, 1H, J$_{3,4}$=3.5 Hz, H3), 4.52 (d, 1H, J$_{1,2}$=8.0 Hz, H1), 2.71, 2.53 (t, 2H each, J=7.0 Hz, S—CH$_2$), 2.16, 2.08, 2.06, 1.99 (s, 3H each, CH$_3$CO), 0.88 (t, 3H, J=7.0 Hz, CH$_3$—CH$_2$) ppm. $^{13}$C-NMR (CDCl$_3$, TMS) δ 170.4, 170.2, 170.1, 169.4 (CO), 101.4 (Cl), 70.9, 70.7, 68.7, 67.0 (C2–C5), 69.8 (CH$_2$—O), 61.3 (C6), 32.6, 31.8, 31.4, 29.8, 29.2, 28.8, 22.7 (CH$_2$), 20.8, 20.7, 20.6 (CH$_3$CO), 14.1 (CH$_3$—CH$_2$) ppm.

2-(Octylthio)ethyl 2,3,6-tri-O-acetyl-4-O-(2,3,4,6-tetra-O-acetyl-α-D-galactopyranosyl)-β-D-galactopyranoside (23)

Compound 15 (484 mg; 0.65 mmol), octanethiol (110 mg; 0.75 mmol; 130 μl), methyltrioctylammonium chloride (ca 10 mg) and cesium carbonate (245 mg; 0.75 mmol) were dissolved in benzene (1 ml) and water (1 ml). The reaction mixture was treated as for compound 21. Chromatography gave the title compound (23) (250 mg) and starting compound 15 (160 mg). Yield (based on consumed 15): 71%; [α]$_D^{21}$+65.3° (c 1.4; CHCl$_3$); $^1$H-NMR (CDCl$_3$, TMS) δ 5.57 (dd, 1H, J$_{4',5'}$=1 Hz, H4'), 5.39 (dd, 1H, J2', 3'=11 Hz, J$_{3',4'}$=3.5 Hz, H3'), 5.20 (dd, H1, J$_{1',2'}$=3.5 Hz, H2'), 5.19 (dd, 1H, J$_{2,3}$=11 Hz, J$_{1,2}$=7.5 Hz, H2), 5.01 (d, 1H, J$_{1',2'}$=3.5 Hz, H1'), 4.81 (dd, 1H, J$_{3,4}$=3 Hz, H3), 4.51 (d, 1H, J$_{1,2}$=7.5 Hz, H1), 2.73, 2.53 (t, 2H each, J=7 Hz, CH$_2$—S), 2.13, 2.11, 2.08, 2.08, 2.07, 2.04, 1.99 (s, 3H each, CH$_3$—CO) ppm. $^{13}$C-NMR (CDCl$_3$, TMS) 170.7, 170.6, 170.5, 170.4, 170.1, 169.8, 169.1 (CO), 101.2 (Cl), 99.4 (Cl'), 77.1, 72.7, 71.9, 68.6, 68.6, 67.8, 67.4, 67.1 (C2–C5, C2'–C5'), 69.6 (O—CH$_2$—CH$_2$—S), 62.0, 60.5 (C6, C6'), 32.6, 31.8, 31.3, 29.8, 29.2, 28.8, 22.7 (aglycon-CH$_2$), 21.0, 20.8, 20.7 (CH$_3$—CO), 14.1 (CH$_3$—CH$_2$) ppm.

Method G
2-(Octadecylthio)ethyl 2,3,6-tri-O-acetyl-4-O-(2,3,4,6-tetra-O-acetyl-α-D-galactopyranosyl)-β-D-galactopyranoside (24)

Compound 15 (743 mg; 1 mmol), octadecylthiol (315 mg; 1.1 mmol) and cesium carbonate (391 mg; 1.2 mmol) were added to dry dimethylformamide (8 ml) at room temperature under nitrogen. The reaction was followed by TLC. After 24 h, the reaction mixture was distributed between water and ether. The ether phase was dried (Na$_2$SO$_4$) and evaporated. The residue was chromatographed (ethyl acetate:isooctane 1:1) to give the title compound (24) (300 mg) and the starting compound (15) (400 mg). Yield (based on consumed 15): 69% [α]$_D^{23}$+54.7° (c 0.5, CHCl$_3$); $^1$H-NMR (CDCl$_3$, TMS): the main part of the spectrum (1.9–5.6 ppm) was practically identical with that of compound 23. $^{13}$C-NMR (CDCl$_3$, TMS) δ 170.6, 170.5, 170.4, 170.4, 170.1, 169.7, 169.1 (CO), 101.2 (Cl'), 99.4 (Cl,), 77.1, 72.6, 71.9, 68.5, 68.5, 7.8, 67.3, 67.0 (C2–C5, C2'–C5'), 69.5 (O—CH$_2$—CH$_2$—S), 62.0, 60.4 (C6, C6'), 32.6, 31.9, 31.3, 29.8, 29.6, 29.5, 29.3, 29.2, 28.8, 22.6 (aglycon-CH$_2$), 20.9, 20.7, 20.7, 20.6, 20.6, (CH$_2$—CO), 14.1 (CH$_3$—CH$_2$) ppm.

2-(p-Nitrophenylthio)ethyl 2,3,4,6-tetra-O-acetyl-β-D-galactopyranoside (25)

p-Nitrothiophenol (50 mg; 0.32 mmol) was added to a suspension of sodium hydride (oil-free; 11 mg; 0.46 mmol) in dimethylformamide (3 ml) at room temperature and with stirring. 2-Bromoethyl 2,3,4,6-tetra-O-acetyl-β-D-galactopyranoside (1) (110 mg; 0.24 mmol) in dimethylformamide (3 ml) was added during 10 min to the thiophenol solution and the reaction mixture was stirred for another 75 min (TLC: SiO$_2$, ethyl acetate:isooctane 1:1). The reaction mixture was poured into ice-cold water (20 ml) and ether (40 ml). The aqueous phase was extracted further with ether (40 ml) and the combined organic phases were washed with cold water (20 ml) and dried (sodium sulfate). Evaporation and chromatography (SiO$_2$, ethyl acetate:isooctane 1:1) gave the title compound (25) as a light yellow oil. Yield: 80 mg (62%). [α]$_D^{23}$−15.2° (c 1.1; CDCl$_3$); $^1$H-NMR (CDCl$_3$, TMS) δ 8.14, 7.36 (ABq, 4H, J$_{AB}$=9.2 Hz, aromatic H), 5.40 (dd, 1H, J$_{4,5}$=1.0 Hz, H4), 5.22 (dd, 1H, J$_{2,3}$=10.5 Hz, H2), 5.01 (dd, 1H, J$_{3,4}$=3.4 Hz, H3), 4.52 (d, 1H, J$_{1,2}$=7.8 Hz, H1), 3.25 (t, 2H, J=6.5 Hz, S—CH$_2$), 2.17, 2.05, 2.04, 1.99 (s, 3H each, CH$_3$CO) ppm. $^{13}$C-NMR (CDCl$_3$, TMS) δ 170.4, 170.2, 170.1, 169.4 (CO), 146.6, 145.3, 126.5, 124.1 (aromatic C), 101.4 (Cl), 70.9, 70.8, 68.5, 66.9 (C2–C5), 67.9 (CH$_2$—O) 61.2 (C6), 31.8 (S—CH$_2$), 20.8, 20.7, 20.6 (CH$_3$CO) ppm.

2-(p-Aminophenylthio)ethyl 4-O-(β-D-galactopyranosyl)-β-D-galactopyranoside (26)

p-Aminothiophenol (205 mg; 1.64 mmol) was dissolved in dimethylformamide (4 ml). Sodium hydride (70 mg; 2.9 mmol) was added and the mixture was stirred under nitrogen for 20 min at room temperature. 2-Bromoethyl 2,3,6-tri-O-acetyl-4-O-(2,3,4,6-tetra-O-acetyl-β-D-galactopyranosyl)-β-D-galactopyranoside 14 (640 mg; 0.86 mmol) in dimethylformamide (7 ml) was added and the reaction mixture was stirred under nitrogen for 2 h (TLC:SiO$_2$, ethyl acetate:isooctane 3:1) and poured into cold water (40 ml). The water solution was extracted with ether (4×20 ml) and the combined ether solutions were washed with water (10 ml) and dried (sodium sulfate). Evaporation gave a residue that contained a series of partly de-acetylated compounds. Evaporation of the water solution gave an additional amount of partly de-acetylated material. The combined residues were de-acetylated (sodium methoxide/methanol) and the product (after evaporation) was filtered through a column (SiO$_2$, ethyl acetate/methanol 2:3) which gave crystalline (needles) 26. Yield: 425 mg (99%). Recrystallization from methanol gave an analytical sample: mp 104°–106°, [α]$_D^{23}$−0.8° (c 1.1; H$_2$O); $^1$H-NMR (DMSO-D6 plus D$_2$O, 50° C., TMS) δ 7.13, 6.58 (d, 2H each, J=8.5 Hz, aromatic H), 4.28 (d, 1H, J=7.0 Hz, H1'), 4.28 (d, 1H, J=7.5 Hz, H1), 2.90 (t, 2H, J=7.0 Hz, CH$_2$—S) ppm. $^{13}$C-NMR (DMSO-D6 plus D$_2$O) δ 149.2, 136.6, 124.7, 119.7 (aromatic C), 107.0, 105.5 (Cl, Cl'), 79.7, 77.8, 76.9, 75.9, 75.5, 74.2, 73.9, 71.4, 70.7, (C2–C5, C2'–C5', CH$_2$O), 63.8, 63.1 (C6, C6'), 37.6 (CH$_2$—S) ppm.

2-(p-Aminophenylthio)ethyl 4-O-(α-D-galactopyranosyl)-β-D-galactopyranoside (27)

2-Bromoethyl 2,3,6-tri-O-acetyl-4-O-(2,3,4,6-tetra-O-acetyl-αD-galactopyranosyl)-β-D-galactopyranoside (15) (170 mg; 0.23 mmol) was treated as above (compound 26). The crude product, that was obtained after the deacetylation reaction, was filtered through a column (SiO$_2$, ethyl acetate/methanol 2:3) which gave the title compound (27) as an amorphous solid. Yield: 110 mg (97%). Chromatography (SiO$_2$, chloroform/methanol/water 65:35:10; lower phase) gave an analytical sample: [α]$_D^{23}$+70.6° (c 0.58; H$_2$O); $^1$H-NMR (DMSO-D6 plus D$_2$O, 50°) δ 7.13, 6.56 (d, 2H each, J=8.4 Hz, aromatic H), 4.83 (d, 1H, J=3.3 Hz, H1'), 4.14 (d, 1H, J=7.6 Hz, H1), 2.89 (t, 2H, J=7.5 Hz, $CH_2$—S) ppm. $^{13}$C-NMR (DMSO-D6 plus $D_2O$) δ 149.1, 136.5, 124.8, 119.7 (aromatic C), 105.7, (C1), 102.9 (C1'), 79.8, 77.7, 75.1, 73.6, 73.5, 71.9, 71.7, 71.4, 70.8 (C2–C5, C2'–C5', $CH_2O$), 63.3, 62.8 (C6, C6'), 37.6 ($CH_2Br$) ppm.

EXAMPLES 28–31

Figure 4:
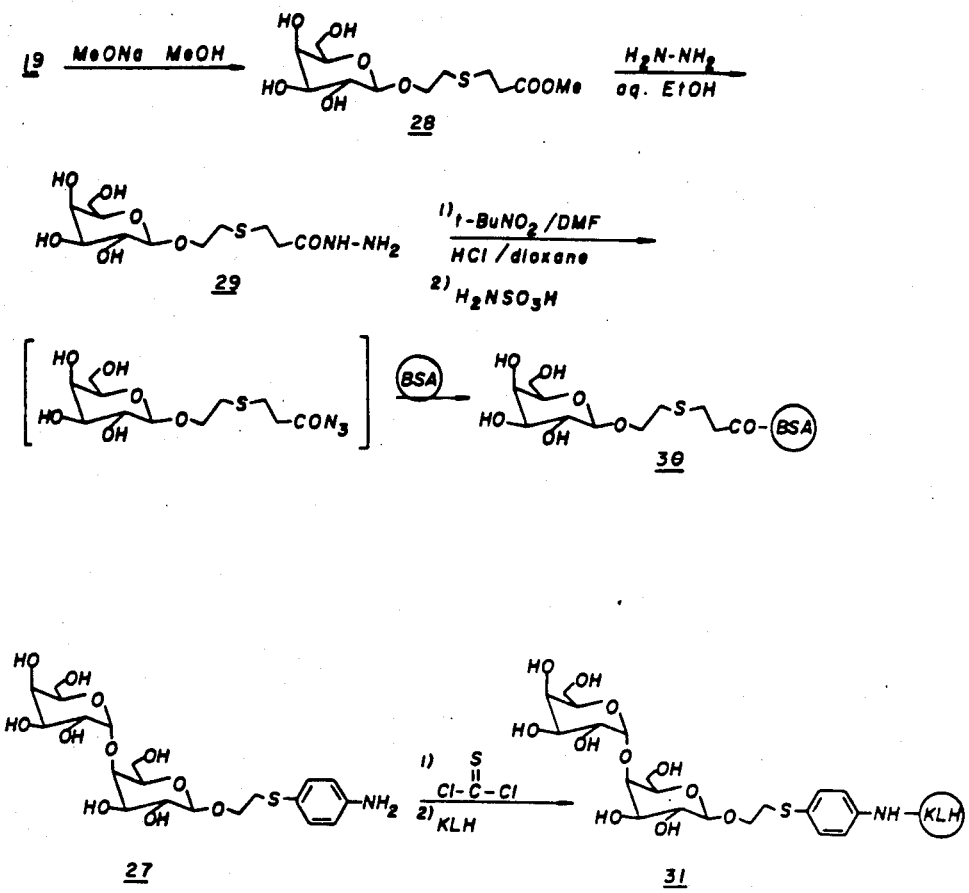
FIG. 4 shows model reactions for the coupling of spacer-arm glycosides to proteins.

Preparation of complete neo-glycoconjugates (cf. FIG. 4)

The two spacer-arm glycosides 28 and 27, having terminal ester and amino groups, respectively, were coupled to protein by well established procedures[40,41,43].

2-(2-Methoxycarbonylethylthio)ethyl β-D-galactopyranoside (28)

2-(2-Methoxycarbonylethylthio)ethyl 2,3,4,6-tetra-O-acetyl-β-D-galactopyranoside (19) (1.00 g; 2.32 mmol) was dissolved in 25 ml of dry methanol and added to a solution of sodium methoxide in methanol, prepared from sodium (~0.05 g) and 10 ml of methanol. Stirring was continued for 4 h after which the reaction mixture was neutralized with Duolite-H$^+$ (methanol washed and dried). Filtration and evaporation of the solvent gave a quantitative yield of the title compound (28; 590 mg) which was pure according to TLC ($SiO_2$, chloroform/methanol/water 65:35:10) and NMR ($D_2O$, TMS as an external standard): δ 4.44 (d, 1H, $J_{1,2}$=7.62 Hz, H1), 4.08 (m, 1H, $OCH_2$—$CH_2$), 3.72 (s, 3H, $OCH_3$), 3.52 (dd, 1H, H2), 2.92-2.70 (m, 6H, $CH_2S$, $CH_2CO$). $^{13}$C-NMR ($D_2O$, TMS as an external standard) δ 178.2 (CO), 105.8 (C-1), 78.1, 75.6, 73.6, 71.5 (C2–C5), 71.7 (C-6), 63.8 (O—$CH_2$ of aglycon) 55.2 ($OCH_3$), 37.1, 33.7, 29.3 (—$CH_2$ of aglycon).

2-(2-Hydrazinocarbonylethylthio)ethyl β-D-galactopyranoside (29)

2-(2-Methoxycarbonylethylthio)ethyl β-D-galactopyranoside (28) (500 mg) was dissolved in ethanol (99.5%; 2.5 ml) and hydrazine hydrate (85%; 1 ml) was added. The reaction mixture was left at room temperature over night (TLC; $SiO_2$, chloroform/methanol/water 65:35:10, lower phase). Evaporation gave the title compound (29) as a syrup (pure by TLC and $^1$H-NMR) in quantitative yield. Recrystallization from ethanol gave the pure compound: mp 178°–179°; $[α]_D^{23}$ −2.2° (c 0.5; $H_2O$); $^1$H-NMR ($D_2O$, TMS as an external standard) δ 4.43 (d, 1H, $J_{1,2}$=7.7 Hz, H1), 4.07 (m, 1H, O—$CH_2$—$CH_2$), 3.92-3.60 (m, 7H), 3.50 (dd, 1H, $J_{2,3}$=11.6 Hz, H2), 2.90, 2.86 (t, 2H each, J=7 Hz, —$CH_2S$), 2.54 (t, 2H, $CH_2CO$) $^{13}$C—NMR ($D_2O$, TMS as an external standard) δ 176.1 (CO), 105.6 (C-1), 77.9, 75.4, 73.4, 71.6, 71.3 (C2-C6), 63.7 (O—$CH_2$—$CH_2$), 36.5, 33.5, 29.9 ($CH_2S$, $CH_2CO$).

Bovine serum albumin conjugate 30

Compound 29 was coupled to BSA using the acyl azide method as described for the preparation of the blood-group H-disaccharide-BSA conjugate (48). The incorporation of the hapten was 35 mol per mol of BSA as determined by both differential sulfur elemental analysis and by the phenolsulfuric acid method[42].

KLH conjugate 31

Compound 27 was coupled to KLH using the procedure described in Ref. 43b (the thiophosgene method). The incorporation of the hapten was 490 mol per mol of KLH as determined by the phenol-sulfuric acid method[42].

EXAMPLES 32–37

Preparation of agglutination inhibitors (cf. FIG. 5)

Ethyl glycosides were prepared from the corresponding 2-bromoethyl glycoside by a hydrogenolytic cleavage of the carbon-bromine bond. The bidentate glycoside inhibitors were prepared by alkylation of di-thiols by a method analogous to the one used for the preparation of the complete spacer-arm glycosides (Method F, vide supra).

Ethyl 2,3,4,6-tetra-O-acetyl-β-D-galactopyranoside (32)

2-Bromoethyl 2,3,4,6-tetra-O-acetyl-β-D-galactopyranoside (1) (98 mg; 0.22 mmol) was dissolved in methanol (5 ml) and aqueous potassium hydroxide (0.3M, 5 ml) and hydrogenated (Pd/C 10%; 47 mg) at atmospheric pressure for 3 h. The reaction mixture (pH 6) was filtered and evaporated to give a residue that was pure by TLC ($SiO_2$, chloroform/methanol/water 65:35:10, lower phase). The residue was acetylated (acetic anhydride/pyridine 1:1; 60°; 1.5 h) and the reaction mixture was cooled, filtered and evaporated with toluene and ethanol several times and finally dried (0.1 torr). Crystallization from ether/isooctane gave the title compound (32). Yield: 55 mg (68%). Mp 92°–93°; $[α]_D^{22}$ −31.0° (c 1.2; benzene); $[α]_D^{24}$ −14.4° (c 1.2; $CDCl_3$) (Lit.[56] mp 88°; $[α]_D^{20}$ −29.8° (c 10; benzene)]; $^1$H-NMR ($CDCl_3$, TMS) δ 5.40 (dd, 1H, $J_{4,5}$=1.0 Hz, $J_{4,3}$=3.5 Hz, H4), 5.22 (dd, 1H, $J_{2,3}$=10.5 Hz, $J_{1,2}$=8.0 Hz, H2), 5.02 (dd, 1H, H3), 4.48 (d, 1H, H1), 4.16 (m, 2H, H6), 3.93 (oct, 1H, $J_{gem}$=10.0 Hz, $J_{vic}$=7.0 Hz, $OCH_2CH_3$), 3.89 (dd, 1H, $J_{5,6}$~4 Hz, H5) 3.60 (oct, 1H, $OCH_2CH_3$), 2.17, 2.07, 2.06, 1.99 (s, 3H each, $CH_3CO$), 1.22 (t, 3H, $OCH_2CH_3$). $^{13}$C-NMR ($CDCl_3$, TMS) δ 170.4, 170.3, 170.2, 169.4 (CO), 101.1 (C1), 71.0, 70.6, 68.9, 67.1 (C2–C5), 65.7 ($CH_2CH_3$), 61.3 (C6), 20.8, 20.7, 20.7, 20.6 ($CH_3CO$), 15.1 ($CH_2CH_3$).

Ethyl 2,3,6-tri-O-acetyl-4-O-(2,3,4,6-tetra-O-acetyl-α-D-galactopyranosyl)-β-D-galactopyranoside (33)

2-Bromoethyl 2,3,6-tri-O-acetyl-4-O-(2,3,4,6-tetra-O-acetyl-α-D-galactopyranosyl)-β-D-galactopyranoside (15) (740 mg; 1 mmol) was dissolved in methanol (14 ml) by heating. Sodium methoxide in methanol (0.1M; 2 ml) was added and the reaction mixture was stirred at room temperature for 2 h. Sodium hydroxide (87 mg; 2.2 mmol) in water (2 ml) was added together with the catalyst (10% Pd/C; 120 mg) and the reaction mixture was hydrogenated (15 h) at atmospheric pressure. Filtration (Celite) and evaporation (<0.1 torr) gave a colorless, amorphous residue that was suspended in a mixture of acetic anhydride and pyridine (1:1; 10 ml). The reaction mixture was stirred (75°; 3 h), cooled and poured into ether (50 ml). The ether solution was washed (water, sat. sodium hydrogen carbonate solution, water), dried (sodium sulfate) and evaporated (<0.1 torr) which gave 33 as a crystalline residue that was pure by TLC ($SiO_2$, ethyl acetate:isooctane 3:1). Yield: 650 mg (98%). Recrystallization from methanol-water gave an analytical sample (needles): mp 133°–135°; $[α]_D^{22}$ +81.4° (c 0.9; $CHCl_3$); $^1$H-NMR ($CDCl_3$, TMS) δ 5.57 (d, 1H, H4'), 5.39 (dd, 1H, $J_{3',4'}$=3.2 Hz, H3'), 5.20 (dd, 1H, $J_{2',3'}$=11.0 Hz, H2'), 5.18 (dd, 1H, $J_{2,3}=10.8$ Hz, H2), 5.01 (d, 1H, $J_{1',2'}=3.5$ Hz, H1'). 4.82 (dd, 1H, $J_{3,4}=2.6$ Hz, H3), 4.48 (d, 1H, $J_{1,2}=7.9$ Hz, H1), 4.06 (d, 1H, H4), 3.92, 3.59 (dq, 1H each, $J=9.7$ and 7.1 Hz, CH$_3$—CH$_2$—O), 2.13, 2.11, 2.08, 2.075, 2.06, 2.04, 1.99 (s, 3H each, CH$_3$—CO), 1.22 (t, 3H, $J=7.1$ Hz, CH$_3$—CH$_2$—O) ppm. $^{13}$C-NMR (CDCl$_3$, TMS) $\delta$ 170.7, 170.6, 170.5, 170.4, 170.1, 169.7, 169.1 (CH$_3$—CO), 100.9 (Cl), 99.4 (Cl'), 77.2, 72.8, 71.9, 68.8, 68.6, 67.9, 67.4, 67.1 (C2-C5, C2'-C5'), 65.4 (CH$_2$—CH$_3$), 62.1, 60.5 (C6, C6'), 21.0, 20.8, 20.7, 20.6 (CH$_3$—CO), 15.1 (CH$_2$—CH$_3$) ppm.

1,12-Bis(2,3,4,6-tetra-O-acetyl-$\beta$-D-galactopyranosyloxy)-3,10-dithiadodecane (34) and 2-(6-mercaptohexylthio)ethyl 2,3,4,6-tetra-O-acetyl-$\beta$-D-galactopyranoside (35)

2-Bromoethyl 2,3,4,6-tetra-O-acetyl-$\beta$-D-galactopyranoside (1) (915 mg; 2.0 mmol) and hexane-1,6-dithiol (150 mg; 1.0 mmol; 153 $\mu$l) were dissolved in benzene (3 ml) and aqueous potassium hydroxide (112 mg; 2 mmol; 3 ml) was added together with methyltrioctylammonium chloride (ca 10 mg). The reaction mixture was stirred under nitrogen for 24 h and the phases were separated. The aqueous phase was extracted with methylene chloride and the combined organic phases were washed with water. Drying and evaporation gave a residue that was chromatographed (SiO$_2$, ethyl acetate:isooctane 1:1) to give the title compounds 34 and 35.

Compound 34: Yield: 190 mg (21%); viscous syrup; $[\alpha]_D^{23}-10.3°$ (c 1.4; CDCl$_3$); $^1$H-NMR (CDCl$_3$, TMS) $\delta$ 5.40 (d, 2H, H4), 5.22 (dd, 2H, $J_{2,3}=10.5$ Hz, H2), 5.03 (dd, 2H, $J_{3,4}=3.5$ Hz, H3), 4.51 (d, 2H, $J_{1,2}=8.0$ Hz, H1), 2.70, 2.53 (t, 4H each, $J=7.0$ Hz, S—CH$_2$), 2.16, 2.09, 2.06, 1.99 (s, 6H each, CH$_3$CO) ppm. $^{13}$C-NMR (CDCl$_3$, TMS) $\delta$ 170.8, 170.7, 170.6, 169.9 (CO), 101.8 (Cl), 71.3, 71.1, 69.1, 67.4 (C2-C5), 70.2 (CH$_2$—O), 61.7 (C6), 32.9, 31.8, 30.0, 28.8 (CH$_2$), 21.3, 21.1, 21.0 (CH$_3$CO) ppm.

Compound 35: Yield: 280 mg (27%); viscous oil; $[\alpha]_D^{23}-8.9°$ (c 1.3; CDCl$_3$); $^1$H-NMR (CDCl$_3$, TMS) $\delta$ 5.41 (d, 1H, H4), 5.24 (dd, 1H, $J_{2,3}=10.5$ Hz, H2), 5.04 (dd, 1H, $J_{3,4}=3.5$ Hz, H3), 4.53 (d, 1H, $J_{1,2}=8.0$ Hz, H1), 2.72 (t, 2H, $J=7.0$ Hz, S—CH$_2$), 2.50-2.60 (m, 4H, S—CH$_2$), 2.16, 2.08, 2.06, 1.99 (s, 3H each, CH$_3$CO) ppm. $^{13}$C-NMR (CDCl$_3$, TMS) $\delta$ 170.8, 170.7, 170.6, 169.9 (CO), 101.9 (Cl), 71.4, 71.2, 69.2, 67.5 (C2-C5), 70.3 (CH$_2$—O), 61.7 (C6), 34.3, 33.0, 31.9, 30.1, 28.7, 28.4, 25.0 (CH$_2$), 21.3, 21.2, 21.1 (CH$_3$CO) ppm.

1,15-Bis[2,3,6-tri-O-acetyl-4-O-(2,3,4,6-tetra-O-acetyl-$\alpha$-D-galactopyranosyl)-$\beta$-D-galactopyranosyloxy]-3,13-dithiapentadecane (36) and 2-(9-mercaptononylthio)ethyl 2,3,6-tri-O-acetyl-4-O-(2,3,4,6-tetra-O-acetyl-$\alpha$-D-galactopyranosyl)-$\beta$-D-galactopyranoside (37)

2-Bromoethyl 2,3,6-tri-O-acetyl-4-O-(2,3,4,6-tetra-O-acetyl-$\alpha$-D-galactopyranosyl)-$\beta$-D-galactopyranoside (15) (1486 mg; 2.0 mmol) was treated as above: (compounds 34 and 35). Chromatography (SiO$_2$, ethyl acetate:isooctane 4.1) gave the title compounds 36 and 37 together with the starting compound 15 (457 mg; 31%).

Compound 36: Yield 312 mg (21%); viscous syrup; $[\alpha]_D^{23}+62.2°$ (c 0.9; CHCl$_3$); $^1$H-NMR (CDCL$_3$, TMS) $\delta$ 5.56 (d, 2H, $J_{3',4'}=3.0$ Hz, H4'), 5.39 (dd, 2H, $J_{2',3'}=11.0$ Hz, H2'), 5.20 (dd, 2H, $J_{2,3}=11.0$ Hz, H2), 5.18 (dd, 2H, H3'), 5.00 (d, 2H, $J_{1',2'}=4.0$ Hz, H1'), 4.81 (dd, 2H, $J_{3,4}=10.5$ Hz, H3), 4.50 (d, 2H, $J_{1,2}=8.0$ Hz, H1), 2.53, 2.72 (t, 4H each, $J=7.0$ Hz, S—CH$_2$), 2.13, 2.10, 2.07, 2.06, 2.04, 1.98 (s, CH$_3$—CO) ppm. $^{13}$C-NMR (CDCl$_3$, TMS) $\delta$ 170.7, 170.6, 170.5, 170.4, 170.1, 169,8, 169.1 (CH$_3$CO), 101.2 (Cl), 99.4 (Cl'), 77.1, 72.7, 72.0, 68.6, 68.6, 67.9, 67.4, 67.1 (C2-C5, C2'-C5'), 69.5 (O—CH$_2$), 62.0, 60.5 (C6, C6'), 32.6, 31.4, 29.8, 29.2, 28.8 (CH$_2$), 29.4 (C5 of nonane-dithiol-portion), 21.0, 20.8, 20.7, 20.6 (CH$_3$CO) ppm.

Compound 37: Yield: 335 mg (20%); viscous syrup; $[\alpha]_D^{23}+60.3°$ (c 1.9; CHCl$_3$); $^1$H-NMR (CDCl$_3$, TMS) $\delta$ 5.58 (d, 1H, $J_{3',4'}=3.0$ Hz, H4'), 5.40 (dd, 1H, $J_{2',3'}=11.0$ Hz, H2'), 5.21 (dd, 1H, H3'), 5.19 (dd, 1H, $J_{2,3}=11.0$ Hz, H2), 5.01 (d, 1H, $J_{1',2'}=4.0$ Hz, H1'), 4.82 (dd, 1H, $J_{3,4}=3.0$ Hz, H3), 4.52 (d, 1H, $J_{1,2}=8.0$ Hz, H1), 2.74, 2.55, 2.52 (t, 2H each, $J=7$ Hz, CH$_2$—S), 2.14, 2.11, 2.08, 2.07, 2.04, 1.99 (s, CH$_3$CO) ppm. $^{13}$C-NMR (CDCl$_3$, TMS) $\delta$ 170.7, 170.5, 170.4, 170.3, 170.1, 169.8, 169.1 (CH$_3$—CO), 101.2 (Cl), 99.4 (Cl'), 77.1, 72.7, 71.9, 68.6, 68.6, 67.8, 67.4, 67.1 (C2-C5, C2'-C5'), 69.5 (O—CH$_2$), 62.0, 60.5 (C6, C6'), 34.0, 32.6, 31.3, 29.8, 29.4, 29.2, 29.0, 28.8, 28.3, 24.6 (CH$_2$), 20.9, 20.8, 20.7, 20.6 (CH$_3$—CO) ppm.

EXAMPLES 38-48

The 2-bromoethyl group in standard carbohydrate synthetic chemistry

The blood-group H, P$^k$, and P$_1$ oligosaccharides, as well as a tetrasaccharide found in human urine, have been synthesized in the form of 2-bromoethyl glycosides as illustrations of the compatibility of the 2-bromoethyl group with synthetic chemical reactions. These glycosides have then been used for the preparation of spacer-arm glycosides, ethyl glycosides, neo-glycolipids, and neo-glycoproteins. For an over-view, see FIGS. 6–9, as appended.

2-Bromoethyl 4,6-O-benzylidene-$\beta$-D-galactopyranoside (39)

2-Bromoethyl 2,3,4,6-tetra-O-acetyl-$\beta$-D-galactopyranoside (1) (30.0 mg; 76 mmol) was dissolved in methanol (100 ml) and added to a solution of sodium (0.2 g) in methanol (500 ml) at room temperature. The de-acetylation was completed within a few minutes (TLC: SiO$_2$, ethyl acetate:acetic acid:water 2:1:1). The reaction mixture was neutralized with ion-exchange resin (Duolite H$^+$, methanol-washed), the resin was filtered off and the filtrate was evaporated (<40°) to give the glycoside 38 (18 g; unstable syrup). This was used immediately in the following step.

Dry zinc (II) chloride[57] (14.4 g; 106 mmol) was dissolved in tetrahydrofuran (80 ml) and benzaldehyde (11.2 ml; 106 mmol; freshly distilled and kept under nitrogen in the dark) was added. The solution was stirred for 15 min. at room temperature and 2-bromoethyl $\beta$-D-galactopyranoside 38 (18 g; crude product; vide supra), dissolved in tetrahydrofuran (90 ml), was added. The reaction mixture was stirred over night at room temperature while protected from light. Evaporation gave a residue that was dissolved in methylene chloride (200 ml) and washed with water (2×100 ml). Drying (sodium sulfate) and evaporation gave a crude product that was dissolved in methanol (55 ml) by heating. The hot solution was diluted with ether (200 ml) and cooled which gave the title compound (39) by crystallization (12.5 g). The mother liquor was evaporated and chromatographed (SiO$_2$, ethyl acetate:methanol 85:15) which gave a further crop of 39 (1.8 g). Yield: 13.85 g (49%). Mp 138°-139°; $[\alpha]_D^{24}-29.9°$ (c 1.2; CDCl$_3$) H-NMR (CDCl$_3$, TMS) δ 7.4 (m), 7.5 (m) (5H, aromatic), 5.56 (s, 1H, benzylidene), 4.35 (d, 1H, $J_{1,2}=7.1$ Hz, H-1), 4.32 (dd, $J_{6A,6B}=12.7$ Hz, $J_{5,6B}=1.5$ Hz, H-6B), 4.27 (t, O—CH$_2$CH$_2$), 4.21 (m, 2H, H-3, H-4), 4.08 (dd, 1H, $J_{5,6A}=1.8$ Hz, H-6A), 3.88 (m, OCH$_2$CH$_2$), 3.79 (m, H-2), 3.51-3.58 (m, 2H, CH$_2$Br), 3.47 (m, 1H, H-5). $^{13}$C-NMR (CDCl$_3$, TMS) δ 129.3, 128.3, 126.5 (aromatic), 103.1 101.5 (C-1, benzylidene), 75.3, 72.6, 71.6, 66.9 (C2–C5), 69.5, 69.2 (C-6, O—CH$_2$CH$_2$), 30.4 (CH$_2$Br).

2Bromoethyl 3-O-benzoyl-4,6-O-benzylidene-β-D-galactopyranoside (40)

2-Bromoethyl 4,6-O-benzylidene-β-D-galactopyranoside (39) (10.0 g; 26 7 mmol) was dissolved in methylene chloride (50 ml) and pyridine (20 ml) and cooled to −30°. A solution of benzoyl chloride (5.2 g; 37 mmol) in methylene chloride (60 ml) was added dropwise and the temperature of the reaction mixture was allowed to rise to 0° during 1 h (TLC: SiO$_2$, ethyl acetate:isooctane 2:1). The reaction mixture was washed with cold water and the water phase was extracted several times with methylene chloride. The combined organic phases were dried (Na$_2$SO$_4$) and evaporated twice with toluene. The residue was chromatographed (SiO$_2$, ethyl acetate:isooctane 2:1) and crystallized from isopropanol The mother liquor was re-chromatographed and crystallized. The total yield of crystalline material (40) was 7.6 g (59%) Mp 141°. $[\alpha]_D^{23}+100°$ (c 0.78, CDCl$_3$). $^1$H-NMR (CDCl$_3$, TMS) δ 8.13, 8.10, 7.43-7.35 (m, 10H, aromatic), 5.53 (s, 1H, benzylidene), 5.17 (dd, 1H, $J_{2,3}=10.2$ Hz, H-3), 4.51 (d, $J_{1,2}=7.7$ Hz, H-1), 4.50 (bd, H-4), 4.36 (dd, H-6B), 4.29 (m, OCH$_2$CH$_2$), 4.24 (dd, $J_{2,3}=10.2$ Hz, H-2), 4.10 (dd, 1H, $J_{6A,6B}=12.7$ Hz, $J_{5,6}=1.8$ Hz, H-6A), 3.88 (m, 1H, OCH$_2$CH$_2$), 3.47 (m, H-5), 3.55 (m, CH$_2$Br).

2-Bromoethyl 3-O-benzoyl-4,6-O-benzylidene-2-O-(2,3,4-tri-O-benzyl-α-L-fucopyranosyl)-β-D-galactopyranoside (41)

A methylene chloride solution of 1-bromo-2,3,4-tri-O-benzyl-α-L-fucopyranose, prepared from 1-O-(p-nitrobenzoyl)-2,3,4-tri-O-benzyl-β-L-fucopyranose (4.00 g; 6.86 mmol) with hydrogen bromide in methylene chloride (total volume 30 ml) was added to a mixture of 2-bromoethyl 3-O-benzoyl-4,6-O-benzylidene-β-D-galactopyranoside (40) (4.00 g; 8.35 mmol), tetraethyl ammonium bromide (1.8 g; 8.5 mmol) and 5 g of 4 Å molecular sieves in 20 ml methylene chloride at room temperature in a dry nitrogen atmosphere. The proceeding of the reaction was followed by TLC (toluene:ethyl acetate 5:1). Two additional batches of the fucosyl bromide (from 2.00 g; 3.46 mmol) of the precursor) were added after 2 and 5 days, respectively. Totally 8.00 g (13.7 mmol) of 1-O-(p-nitrobenzoyl)-2,3,4-tri-O-benzyl β-L-fucopyranose was used. After 8 days, 40 was almost completely comsumed. The reaction mixture was filtered through Celite, which was washed with 2×25 ml of methylene chloride. The filtrate was washed with 2×50 ml of aqueous sodium bicarbonate and 50 ml of water. After drying (Na$_2$SO$_4$) and evaporation of the solvent, the residue was chromatographed (SiO$_2$, toluene:ethyl acetate 5:1) to give 3.0 g (40%) of the pure title compound (41) as a foam, which was recrystallized from isooctane-ethyl acetate; mp 172° C.

$[\alpha]_D^{24}+26°$ (c 0.72, CHCl$_3$). $^1$H-NMR (CDCl$_3$, TMS) δ 8.06-6.98 (m, 25H, aromatic), 5.50 (s, benzylidene), 5.46 (d, $J_{1',2'}=3.0$ Hz, H-1'), 5.40 (dd, $J_{2,3}=9.7$ Hz, $J_{3,4}=3.8$ Hz, H-3), 4.95 (d, 1H, benzyl), 4.77 (d, 1H, benzyl), 4.68 (d, $J_{1,2}=7.7$ Hz, H-1), 4.56 (H-4), 4.56 (H-5'), 4.47 (H-2), 4.34 (m, OCH$_2$CH$_2$), 4.32 (s, benzyl), 4.10 (bd, 1H, $J_{6A,6B}=13.6$ Hz, H-6A), 4.02 (dd, 1H, H-3'), 3.94 (dd, 1H, H-2'), 3.73 (m, OCH$_2$CH$_2$), 3.68 (bs, 1H, H-4'), 3.59 (bs, 1H, H-5), 3.49 (m, 2H, CH$_2$Br), 1.14 (d, 3H, $J_{5,6'}=6.6$ Hz, H-6').

2-Bromoethyl 4,6-O-benzylidene-2-O-(2,3,4-tri-O-benzyl-α-L-fucopyranosyl)-β-D-galactopyranoside (42)

Methanolic sodium methoxide was prepared from 250 ml of methanol and sodium (0.1 g; 4 mmol). Compound 41 (4.00 g; 4.46 mmol) in 25 ml of methanol was added and the reaction mixture was stirred for 4 days at room temperature. TLC (toluene:ethyl acetate 5:1) showed complete conversion of 41. The reaction mixture was neutralized with methanol-washed Duolite H+ resin and filtered. The solvent was removed to give 3.45 g of crude 42, which was chromatographed (SiO$_2$, toluene:ethyl acetate 5:1). Thus 2.40 g (68%) of 42 was obtained as a foam. $[\alpha]_D^{23}-49°$ (c 0.78, CHCl$_3$). $^1$H-NMR (CDCl$_3$, TMS) δ 7.54-7.22 (m, 20H, aromatic), 5.55 (s, 1H, bensylidene), 5.30 (d, 1H, $J_{1',2'}=3.2$ Hz), 4.97 (d, 1H, H-1', benzylic), 4.64 (d, benzylic), 4.45 (d, J~8 Hz, H-1), 4.32 (H-5'), 4.03 (H-2') 1.13 (d, 3H, $J_{5',6'}=6.4$ Hz, H-6'). $^{13}$C-NMR (CDCl$_3$, TMS) δ 101.8, 101.4 (C-1 and benzylidene -C), 99.1 (C-1'), 30.1 (CH$_2$Br), 16.7(C-6').

2-Bromoethyl 3,4,6-tri-O-acetyl-2-O-(2,3,4-tri-O-acetyl-α-L-fucopyranosyl)-β-D-galactopyranoside (44)

A solution of 42 (0.50 g; 0.63 mmol) in 20 ml of acetic acid was hydrogenated with 0.50 g 10% palladium on charcoal at atmospheric pressure over night. The reaction mixture was filtered and the solvent was removed by repeated evaporations with toluene to give 0.27 g (100%) of 2-bromoethyl 2-O-(α-L-fucopyranosyl)-β-D-galactopyranoside (43), which was pure by TLC (SiO$_2$; chloroform:methanol:water 65:35:10). This product was acetylated with 5 ml of pyridine and 2.5 ml of acetic anhydride at room temperature over night. Evaporation of the solvents several times with toluene followed by drying at 10$^{-2}$ mm Hg gave 230 mg (53%) of pure 2-bromoethyl 3,4,6-tri-O-acetyl-2-O-(2,3,4-tri-O-acetyl-β-L-fucopyranosyl)-β-D-galactopyranoside (44) (TLC, SiO$_2$; isooctane:ethyl acetate 1:2) $[\alpha]_D^{23}-77°$ (c 0.95, CHCl$_3$). $^1$H-NMR (CDCl$_3$, TMS) δ 5.43 (d, 1H, $J_{1',2'}=3.7$ Hz, H1'), 5.34 (dd, H3'), 5.3 (bs, H4, H4') 5.04 (dd, 1H, $J_{3,4}=3.4$ Hz, H3), 4.99 (dd, 1H, $J_{2',3'}=10.9$ Hz, H2'), 4.74 (q, 1H, $J_{5',6'}=6.7$ Hz, H5'), 4.55 (d, 1H, $J_{1,2}=7.9$ Hz, H1), 4.30 (dt, O—CH$_2$CH$_2$), 4.1 (H6), 4.00 (dd, $J_{2,3}=10$ Hz, H2), 3.90 (m, OCH$_2$CH$_2$ and H5), 3.52 (m, 2H, CH$_2$Br), 1.15 (d, 3H, H6'), 2.15, 2.14, 2.05, 2.00, 1.99, 1.98 (18H, OAc).

2-(2-Methoxycarbonylethylthio)ethyl 2-O-(α-L-fucopyranosyl)-β-D-galactopyranoside (46)

Without further purification, 44 (230 mg; 0.335 mmol) was dissolved in 0.7 ml of benzene. To this solution, methyl 3-mercaptopropionate (94 mg; 0.787 mmol), water (0.5 ml), cesium carbonate (257 mg; 0.787 mmol) and methyl trioctyl ammonium chloride (ca 5 mg) were added and the resulting mixture stirred at room temperature for 24 h. TLC (SiO$_2$; isooctane:ethyl acetate 1:2) showed a new more polar spot as the major product but a considerable amount of the starting material was still left. Another 2 equivalents of cesium carbonate and the thiol ester were added and stirring was continued for 7 days. At this point there was still starting material left but since deacetylation products started to appear, the reaction mixture was diluted with 50 ml of benzene, the organic phase was separated, washed with water and dried (Na$_2$SO$_4$). After removal of the solvent the crude product was chromatographed (SiO$_2$; isooctane:ethyl acetate 1:1) to give 150 mg (62%) of 45 as a syrup. Sodium methoxide in methanol was prepared from 50 ml of dry methanol and 10 mg of sodium. To this solution, 45 (150 mg; 0.207 mmol) was added and the mixture stirred for 4 h at room temperature. TLC (chloroform:methanol:water 65:35:10) showed at this point a single spot. Duolite H$^+$ (methanol washed and carefully dried) was added to neutrality. Filtration and evaporation of the solvent gave 76 mg (78%) of the title compound (46) as a syrup, which was used without further purification for the next step. $[\alpha]_D^{20} = -75°$ (c 0.70, H$_2$O). $^1$H-NMR (D$_2$O, TMS as external standard) δ 5.29 (d, 1H, $J_{1',2'} = 3.6$ Hz, H1'), 4.54 (d, 1H, $J_{1,2} = 7.7$ Hz, H1), 4.43 (q, 1H, H5'), 4.1 (m, 1H, O—CH$_2$CH$_2$), 3.75 (s, OCH$_3$), 3.63 (dd, H2), 2.88-2.75 (m, 6H, CH$_2$S, CH$_2$—CO), 1.23 (d, 3H, $J_{5',6'} = 6.4$ Hz, H6'). $^{13}$C-NMR (D$_2$O, TMS as external standard) δ 178.1 (CO), 104.3, 102.0 (Cl, Cl'), 78.9, 77.9, 76.6, 74.8, 72.3, 71.8, 71.5, 71.1, 69.7, 63.8, 55.2, 37.1, 33.9, 29.3 (ring- and spacer carbons), 18.2 (C6').

The blood-group H disaccharide conjugate with BSA (48)

Compound 46 (61 mg; 0.13 mmol) was dissolved in 0.25 ml of absolute ethanol and 0.10 ml of 85% hydrazine hydrate was added. After 2 days the solvent and the excess of hydrazine hydrate were evaporated to give a quantitative yield of hydrazide 47 (TLC, chloroform:methanol:water 65:35:10). The hydrazide 47 (20 mg; 0.043 mmol) was dissolved in DMF (1 ml) and the solution cooled to $-25°$ C. A 4.2N solution of hydrogen chloride in dioxane (60 μl) was added, followed by t-butylnitrite (29 mg; 0.08 mmol) in 80 μl of DMF. After 30 min, sulfamic acid (80 μl; 0.040 mmol) was added and stirring continued for 15 min. The acylazide solution was added directly to a 0° C. solution of bovine serum albumin (BSA; 58 mg) dissolved in an aqueous solution, 0.08M in Na$_2$B$_4$O$_7$ and 0.35M in KHCO$_3$ (2 ml). The pH of the solution was adjusted to 9.05-9.30 with 1N aqeous NaOH and 1N HCl during the addition of the acylazide solution. After 20 h at $+4°$ the reaction mixture was dialyzed against water and lyophilized to provide the antigen (48; 33 mg) as a white powder. The degree of incorporation was found to be 8 mol of hapten per mol of BSA as determined by the phenol-sulfuric acid method[42].

EXAMPLES 49-74 (see FIG. 7)

2-Bromoethyl 4,6-O-benzylidene-β-D-glucopyranoside (51)

A solution of 2-bromoethyl 2,3,4,6-tetra-O-acetyl-β-D-glucopyranoside (50, 30 g, 66 mmol) in warm methanol (300 ml) was rapidly cooled and treated with methanolic sodium methoxide (0.1M, 30 ml) at room temperature for 3 h. The reaction was monitored by TLC (SiO$_2$, chloroform:methanol:water 65:35:10, lower phase). The reaction mixture was filtered through a column (5×4 cm) of Duolite C 26 (H$^+$) resin and the solvent was removed. The residue (18.6 g) in N,N-dimethylformamide (20 ml) was added dropwise (10 min) with stirring to mixture of zinc chloride (44 g, 103 mmol) and benzaldehyde (48 g, 471 mmol). After 21 h, ether (500 ml) and ice-water (300 ml) was added and the aqueous phase was extracted with ether (2×100 ml). The ether extracts were washed with aqueous sodium hydrogen carbonate (2×100 ml) and water (50 ml). Dichloromethane was added to prevent crystallization. The solution was dried (Na$_2$SO$_4$) and the solvent was removed, which gave crystalline 51 (18.1 g, 73%). Recrystallization from ethanol gave material with mp 157°-159°, $[\alpha]_d^{21} -43°$ (c 2, chloroform). $^1$H-NMR (CDCl$_3$ + D$_2$O, Me$_4$Si) δ 7.56-7.34 (5H), 5.52 (s, 1H, O$_2$CH—Ph), 4.43 (d, 1H, J=8 Hz, H1), 4.32 (dd, 1H, J=11 and 5 Hz), 4.14 (td, 1H, J=6 and 11 Hz), 3.97-3.34 (8H). $^{13}$C-NMR (CDCl$_3$, Me$_4$Si) δ 136.9, 129.3, 128.3 (2C), 126.3 (2C), 103.3, 101.9 (Cl), 80.4 74.4, 73.0, 69.9 (CH$_2$), 68.5 (CH$_2$), 66.4, 30.1 (CH$_2$—Br).

Anal. Calc. for C$_{15}$H$_{19}$O$_6$Br: C, 48.01; H, 5.10 Found C, 48.18; H, 5.04.

2-Bromoethyl 2,3-di-O-benzyl-4,6-O-benzylidene -β-D-glucopyranoside (52) and 3-O-benzyl-4,6-O-benzylidene-1,2-O-ethylidene-β-D-glucopyranose (53)

A mixture of 51 (4.4 g, 11.7 mmol), benzyl bromide (20 ml, 77 mmol) tetra-butylammoniumhydrogen sulfate (0.5 g) and aqueous sodium hydroxide (10%, 44 ml) was stirred at room temperature for 17 h, diluted with toluene, washed with water, dried (Na$_2$SO$_4$) and concentrated. Column (5×18 cm) chromatography (SiO$_2$, toluene then toluene:ethyl acetate 19:1 and finally ethyl acetate) gave 52 (5.2 g, 80%) and 53 (0.9 g, 20%). Compound 52 had mp 97°-98° (from ethanol), $[\alpha]_D^{21} 31 30°$ (c 2, chloroform). $^1$H-NMR (CDCl$_3$, Me$_4$Si) δ 7.55-6.88 (15H), 5.58 (s, 1H, O$_2$CH—Ph), 4.98, 4.77 (ABq, 2H, $J_{AB} = 11$ Hz, CH$_2$Ph), 4.92, 4.81 (ABq, 2H, $J_{AB} = 11.5$ Hz, CH$_2$Ph), 4.56 (d, 1H, J=7.5 Hz, H1), 4.35 (dd, 1H, J=10.5 and 5 Hz), 4.22 (dt, 1H, J=11 and 5.5 Hz, CH$_2$—CH$_2$—Br), 4.01-3.63 (4H), 3.59-3.35 (4H), 3.52 (bt, J=6 Hz, CH$_2$Br). $^{13}$-NMR (CDCl$_3$, Me$_4$Si) δ 138.4, 138.2, 137.2, 129.0, 128.32 (2C), 128.28 (2C), 128.23 (4C), 128.01 (2C), 127.7, 127.6, 126.0 (2C), 104.1, 101.1 (Cl), 81.9, 81.3, 80.7, 75.4 (CH$_2$), 75.1 (CH$_2$), 70.0 (CH$_2$), 68.7 (CH$_2$), 66.1, 30.0 (CH$_2$Br).

Anal. Calc. for C$_{29}$H$_{31}$O$_6$Br: C, 62.70; H, 5.63. Found: C, 62.94; H, 5.62.

Compound 53 had mp 160.5°-162.5° (from ethanol-ethyl acetate), $[\alpha]_D^{21} -21°$ (c 1.5, chloroform). $^1$H-NMR (CDCl$_3$, Me$_4$Si) δ 7.52-7.18 (10H), 5.57 (s, 1H, O$_2$CH—Ph), 4.86 (s, 2H, CH$_2$—Ph), 4.42 (d, 1H, J=8 Hz, H1), 4.38 (dd, 1H, J=10 and 4.5 Hz), 4.02-3.51 (8H), 3.31 (bt, 1H, J=7.5 Hz). $^{13}$C-NMR (CDCl$_3$, Me$_4$Si) δ 138.3, 137.1, 129.0, 128.3 (2C), 128.2 (2C), 127.8 (2C), 127.6, 126.0 (2C), 101.5, 99.1 (Cl and CH—Ph), 81.7, 80.5, 77.4, 74.3 (CH$_2$), 68.5 (CH$_2$), 68.2, 66.8 (CH$_2$), 66.4.

Anal. Calc. for C$_{22}$H$_{24}$O$_6$: C, 68.73; H, 6.29. Found: C, 68.58; H, 6.33.

2-Bromoethyl 2,3,6-tri-O-benzyl-β-D-glucopyranoside (54)

A mixture of 52 (29.5 g, 53 mmol), sodium cyanoborohydride (9 g, 143 mmol), molecular sieves (3 Å, 30 g) and tetrahydrofuran (175 ml) was stirred while hydrogen chloride-saturated ether (225 ml) was added dropwise[47]. Additional amounts of cyanoborohydride (1 g) and ether solution (25 ml) were added. TLC (SiO$_2$, toluene:ethyl acetate 19:1) showed that 52 had been consumed. Toluene (500 ml) was added and the mixture was washed with ice-water (250 ml) and cold aqueous sodium hydrogen carbonate (250 ml), dried (Na$_2$SO$_4$) and concentrated to give a semi-crystalline residue (32 g). Column (10×18 cm) chromatography (SiO$_2$, ethyl acetate:isooctane 1:2) gave 54 (17.5 g, 59%). Recrystallization from toluene-isooctane gave an analytical sample with mp 63°–64°, $[\alpha]_D^{21}$ −18° (c, 1.0, chloroform). $^1$H-NMR (CDCl$_3$, Me$_4$Si) δ 7.45–7.27 (15H), 5.03, 4.72 (ABq, 2H, $J_{AB}$=10.5 Hz, CH$_2$—Ph), 4.95, 4.72 (ABq, 2H, $J_{AB}$=11.5 Hz, CH$_2$—Ph), 4.60, 4.57 (ABq, 2H, $J_{AB}$=12.0 Hz, CH$_2$—Ph), 4.47 (d, with virtual coupling[58], 1H, $J_{1,2}$=7.5 Hz, H1), 4.23 (dt, 1H, J=11 and 5.5 Hz, CH$_2$—CH$_2$—Br), 3.95–3.39 (10H). $^{13}$C-NMR (CDCl, Me$_4$Si) δ 138.5, 138.3, 137.8, 128.6 (2C), 128.4 (2C), 128.36 (2C), 128.3 (2C), 128.0 (2C), 127.9, 127.7 (2C), 127.68 (2C), 103.8 (C-1), 83.8, 81.5, 75.3 (CH$_2$), 74.8 (CH$_2$), 74.2, 73.6 (CH$_2$), 71.2, 70.0 (CH$_2$), 69.7 (CH$_2$), 30.3 (CH$_2$Br). C$_{29}$H$_{33}$O$_6$Br:

Anal. Calc. for C, 62.48; H, 5.97. Found: C, 62.64; H, 5.97.

2-Bromoethyl 2,3-di-O-benzoyl-4,6-O-benzylidene-β-D-glucopyranoside (55)

Benzoyl chloride (20 ml, 240 mmol) was added (7 min) dropwise with stirring to a cooled (0°) solution of 51 (17 g, 45.3 mmol) in pyridine (85 ml). Ice-water (125 ml) was added after 1 h and the mixture was extracted with ether-dichloromethane (2:1, 750 ml). The organic phase was washed with aqueous sodium hydrogen carbonate (100 ml), and brine (100 ml), dried (Na$_2$SO$_4$) and concentrated to give 55 (27.7 g, 82%). Recrystallization from toluene-ethanol gave an analytical sample with mp 176°–178°, $[\alpha]_D^{21}$ −0.1° (c, 1.1, chloroform). $^1$H-NMR (CDCl$_3$, Me$_4$Si) δ 8.06–7.94 (4H), 7.60–7.20 (11H), 5.80 (t, 1H, J=9 Hz, H3), 5.55 (s, 1H, CH—Ph), 5.50 (dd, 1H, J=9 and 8 Hz, H2), 4.88 (d, 1H, J=8 Hz, H1), 4.44 (dd, 1H, J=10 and 5 Hz, H5), 4.16 (dt, 1H, J=11 and 6 Hz, CH$_2$CH$_2$Br), 4.04–3.65 (4H), 3.39 (t, 2H, J=6 Hz, CH$_2$Br). $^{13}$C-NMR (CDCl$_3$, Me$_4$Si) δ 165.6, 165.2, 136.7, 133.2, 133.1, 129.8 (4C), 129.4, 129.3, 129.1, 128.3 (4C), 128.2 (2C), 126.1 (2C), 101.8, 101.5 (C-1 and CH—Ph), 78.7, 72.2, 72.0, 69.8 (CH$_2$), 68.6 (CH$_2$), 66.7, 29.5 (CH$_2$Br).

Anal. Calc. for C$_{29}$H$_{27}$O$_8$Br: C, 59.70; H, 4.66. Found: C, 60.08; H, 4.80.

2-Bromoethyl 2,3-di-O-benzoyl-6-O-benzyl-β-D-glucopyranoside (56)

A mixture of 55 (26.1 g, 45 mmol), sodium cyanoborohydride (7 g, 110 mmol), molecular sieves (4 Å, 20 g) and tetrahydrofuran (150 ml) was treated essentially as in the preparation of 54 to give 56 (17.1 g, 65%). Recrystallization from isooctane-toluene gave an analytical sample with mp 78°–80°, $[\alpha]_D^{21}$ +53° (c 1.0, chloroform). $^1$H-NMR (CDCl$_3$, Me$_4$Si) δ 8.04–7.92 (4H), 7.57–7.27 (11H), 5.52–5.37 (2H), 4.76 (d with virtual coupling[58], 1H, $J_{1,2}$=8 Hz, H1), 4.65, 4.61 (ABq, 2H, $J_{AB}$=12 Hz, CH$_2$—Ph), 4.14 (dt, 1H, J=11 and 6 Hz, CH$_2$—CH$_2$—Br), 4.02–3.62 (5H), 3.40 (bt, 2H, J~7 Hz, CH$_2$Br). $^{13}$C-NMR (CDCl$_3$, Me$_4$Si) δ 167.1, 165.3, 137.6, 133.4, 133.1, 129.9 (2C), 129.7 (2C), 129.4, 128.9, 128.5 (2C), 128.4 (2C), 128.3 (2C), 127.9, 127.7 (2C), 101.1 (C-1), 76.5, 74.9, 73.7 (CH$_2$), 71.3, 70.6, 69.7 (CH$_2$), 69.5 (CH$_2$), 29.65 (CH$_2$Br).

Anal. Calc. for C$_{29}$H$_{29}$O$_8$Br: C, 59.49; H, 4.99. Found: C, 59.19; H, 5.11.

2-Bromoethyl 2,3,6-tri-O-benzyl-4-O-[2,3,6-tri-O-acetyl-4-O-(2,3,4,6-tetra-O-acetyl-α-D-galactopyranosyl)-β-D-galactopyransyl]-β-D-glucopyranoside (57).

A solution of 49[21g] (21 g, 30 mmol) in dichloromethane (70 ml) was added (45 min) dropwise with stirring to a solution (−78°, N$_2$) of 54 (14 g, 25 mmol), silver trifluoromethanesulfonate (9 g, 35 mmol) and tetramethylurea (4.6 g, 39.6 mmol) in dichloromethane (130 ml). After 5 h the mixture, now at room temperature, was filtered through Celite, diluted with dichloromethane and washed with M hydrochloric acid, aqueous sodium hydrogen carbonate and finally dried (Na$_2$SO$_4$) and concentrated. The residue (35 g) was chromatographed (SiO$_2$, ethyl acetate:isooctane gradient 1:1–3:2) to give 49 (2 g) and 57 (16.5 g), Rechromatography of a fraction containing impure 57 gave additional material (1.3 g). Total yield of 57 was 17.8 g (70% based on reacted 54). Recrystallization from abs. ethanol gave an analytical sample with mp 155°–158°, $[\alpha]_D^{21}$ +58° (c 1.2, chloroform). $^1$H-NMR (CDCl$_3$, Me$_4$Si) δ 7.42–7.20 (15H), 5.58 (dd, 1H, J=3 and <1 Hz, H4″), 5.30 (dd, 1H, J=11 and 3 Hz, H3″), 5.17 (dd, 1H, J=11 and 3.5 Hz, H2″), 5.11 (dd, 1H, J=11 and 8 Hz, H2′), 5.03 (d, 1H, J=11.5 Hz, CH$_2$Ph), 4.94 (d, 1H, J=3.5 Hz, H1″), 4.94 (d, 1H, J=11 Hz, CH$_2$Ph), 4.83 (d, 1H, J=11.5 Hz, CH$_2$Ph), 4.74 (d, 1H, J=12 Hz, CH$_2$Ph), 4.69 (d, 1H, J=11 Hz, CH$_2$Ph), 4.67 (d, 1H, J=8 Hz, H1′), 4.58 (dd, 1H, J=11 and 2.5 Hz, H3′), 4.50 (d, 1H, J=12 Hz, CH$_2$Ph), 4.43 (d, 1H, J=8 Hz, H1), 4.59–4.41 (3H, inter alia H1 and PhCH$_2$), 4.30–4.04 (4H), 3.98–3.36 (12H), 2.12, 2.07, 2.05, 1.98, 1.95, 1.93 (7s, each 3H, MeCO). $^{13}$C-NMR (CDCl$_3$, Me$_4$Si) δ 170.7, 170.6, 170.4, 170.13, 170.1, 169.5, 168.9, 139.3, 138.31, 137.9, 128.5, 128.4, 128.24, 128.16, 127.93, 127.86, 127.64, 127.58, 127.0, 126.9, 103.6 (d, J=158 Hz, C-1), 100.6 (d, J=156 Hz, C-1′), 99.8 (d, J=172 Hz, C-1″), 82.6, 81.5, 77.5 (2C), 75.0 (CH$_2$), 74.9 (CH$_2$), 74.6, 73.6 (CH$_2$) 73.0, 71.7, 69.7, (CH$_2$), 69.3, 68.5, 67.8, 67.7 (CH$_2$), 67.3, 67.0, 61.3 (CH$_2$), 60.2 (CH$_2$), 30.2 (CH$_2$Br), 21.0, 20.73, 20.66, 20.5 (MeCO).

Anal. Calc. for C$_{55}$H$_{67}$O$_{23}$ Br: C, 56.16; H, 5.74. Found: C, 55.90; H, 5.72.

2-Bromoethyl 4-O-[2,3,6-tri-O-acetyl-4-O-(2,3,4,6-tetra-O-acetyl-α-D-galactopyranosyl)-β-D-galactopyranosyl]-β-D-glucopyranoside (58)

Catalytic hydrogenation (atm. pressure, 10% Pd/C, 0.2 g) of 57 (1.05 g, 0.89 mmol) in acetic acid (50 ml) for 2 h, filtration and solvent removal gave 58 (0.81 g, 100%). Recrystallization for methanol gave an analytical sample with mp 178°–180°$[\alpha]_D^{21}$ +77° (c 1.0 chloroform). $^1$-NMR (CDCl$_3$, Me$_4$Si) δ 5.59 (bd, 1H, J~3 Hz, H4″), 5.38 (dd, 1H, J=11 and 3 Hz, H3″), 5.24 (dd, 1H, J=11 and 8 Hz, H2″), 5.22 (dd, 1H, J=11 and ~3 Hz, H2″), 4.97 (d, 1H, J=3.5 Hz, H1″), 4.81 (dd, 1H, J=11 and 3.5 Hz, H3′), 4.67 (d, J=8 Hz, H1′), 4.44 (d, 1H, J=8 Hz, H1), 4.57–4.34 (3H, inter alia H1), 4.30–3.37 (15H), 2.15, 2.11 (2s, each 6H, MeCO), 2.08, 2.05, 2.00 (3s, each 3H, MeCO). $^{13}$C-NMR (CDCl$_3$, Me$_4$Si) δ 170.6, 170.5 (2C), 170.4, 170.1, 169.9, 169.1, 102.6, 101.8 (C1 and C1′), 99.6 (C1″), 80.8, 77.1, 74.5, 74.2, 73.2, 72.6

(2C), 69.8, 68.5, 68.3, 67.7, 67.3, 67.2, 62.4, 60.7, 60.4, 30.0 (CH$_2$Br), 20.8, 20.6 ppm.

Anal. Calc. for C$_{34}$H$_{49}$O$_{23}$Br: C, 45.09; H, 5.45. Found: C, 45.22; H, 5.22.

2-Bromoethyl 2,3,6-tri-O-acetyl-4-O-[-2,3,6-tri-O-acetyl-4-O-(2,3,4,6-tetra-O-acetyl-α-D-galactopyranosyl)-β-D-galactopyranosyl]-β-D-glucopyranoside (59)

(a) A solution of 58 (6.65 g, 7.3 mmol) in acetic anhydride pyridine (1:1, 132 ml) was left at room temperature for 15 h and then co-concentrated with toluene. Crystallization of the residue from abs. ethanol gave 59 (5.22 g, 69%) which had mp 179°–181°, [α]$_D^{21}$ +45° (c 1.6, chloroform). $^1$H-NMR (CDCl$_3$, Me$_4$Si) δ 5.59 (bdd, 1H, J 3 and <1 Hz, H4″), 5.40 (dd, 1H, J=11 and 3 Hz, H3″), 5.22 (t, 1H, J~9 Hz, H3), 5.18 (dd, 1H, J=11 and 3.5 Hz, H2″), 5.11 (dd, 1H, J=11 and 8 Hz, H2′), 4.99 (d, 1H, J=3.5 Hz, H1″), 4.92 (dd, 1H, J=9.5 and 8 Hz, H2), 4.74 (dd, 1H, J=11 and 2.5 Hz, H3′), 4.56 (d, 1H, J=8 Hz, H1), 4.53 (d, 1H, J=8 Hz, H1′), 4.59–4.39 (5H), 4.23–4.05 (5H), 4.02 (bd, 1H, J~2.5 Hz, H4′), 3.90–3.73 (3H), 3.65 (q, 1H, J=9.5 and 2 Hz, H5), 3.46 (bt, 2H, J~6 Hz, CH$_2$Br), 2.14, 2.13, 2.09, 2.07, 2.07, 2.06, 2.05, 1.99 (8s, each 3H, MeCO). $^{13}$C-NMR (CDCl$_3$, Me$_4$Si) δ 170.7, 170.44 (3C), 70,39, 170.1, 169.8, 169.6, 169.5, 168.8, 101.1 (d, J=165 Hz, Cl′), 100.7 (d, J=165 Hz, Cl), 99.6 (d, J=172 Hz, Cl″), 76.9 (C4′), 76.4 (C4′), 72.9 (C3), 72.8 (C3′), 72.7 (C5), 71.8 (C5′), 71.5 (C2), 69.8 (O—CH$_2$—CH$_2$), 69.0 (C2′), 68.8 (C2″), 67.9 C4″), 67.14 (C3″), 67.07 (C5″), 62.1 (C6) 61.3 (C6′), 60.3 (C6″), 20.9, 20.86, 20.8, 20.7, 20.6, 20.5.

Anal. Calc. for C$_{40}$H$_{55}$O$_{26}$Br: C, 46.56; H, 5.37. Found: C, 46.79; H, 5.39.

(b) Catalytic hydrogenation (atm. pressure, 10% Pd/C, 53 mg) of 60 (218 mg, 0.18 mmol) in acetic acid (12 ml) for 1.5 h, filtration and solvent removal gave a quantitative yield of 2-bromoethyl 2,3-di-O-benzoyl-4-O-[2,3,6-tri-O-acetyl-4-O-(2,3,4,6-tetra-O-acetyl-α-D-galactopyranosyl)-β-D-galactopyranosyl]-β-D-glucopyranoside (61). Recrystallization from methanol gave an analytical sample with mp 218°–220°, [α]$_D^{21}$ +69° (c 0.7, chloroform). $^1$H-NMR (CDCl$_3$, Me$_4$Si) δ 8.10–7.92 (4H), 7.60–7.28 (6H), 5.72 (t, 1H, J=9.5 Hz, H3), 5.59 (bd, 1H, J~3 Hz, H4″), 5.35 (dd, 1H, J=9.5 and 8 Hz, H2), 5.29 (dd, 1H, J=11 and 3 Hz, H3″), 5.12 (dd, 1H, J=11 and 8 Hz, H2′), 4.98 (dd, 1H, J=11 and 3.5 Hz, H2″), 4.87 (d, 1H, J=3.5 Hz, H1″), 4.80 (d, 1H, J=8 Hz, H1), 4.66 (dd, 1H, J=11 and 3 Hz, H3′), 4.66 (d, 1H, J=8 Hz, H1′), 4.45 (bt, J~6.5 Hz, H5″), 4.28–3.79 (8H), 3.75–3.49 (3H), 3.48–3.31 (3H), 3.39 (t, 2H, J=6.5 Hz, CH$_2$Br), 2.12, 2.07, 2.044, 2.04, 2.01, 1.93, 1.91 (7s, each 3H, MeCO).

Anal. Calc. for C$_{48}$H$_{57}$O$_{25}$Br: C, 51.76; H, 5.16. Found: C, 51.93; H, 5.14.

Deacetylation with methanolic sodium methoxide (0.02M, 20 ml) for 24 h, neutralization with Duolite C26 (H+) resin, and concentration gave a residue that was acetylated (acetic anhydride:pyridine, 1:1, 50 ml) at room temperature for 22 h. Co-concentration with toluene gave a residue that was subjected to column (1×14 cm) chromatography (SiO$_2$, ethyl acetate:isooctane 2:1) to give 59 (80 mg, 43% from 60). Recrystallization from abs. ethanol gave pure 59, as characterized by melting point, optical rotation and $^1$H-NMR data.

2-Bromoethyl 2,3-di-benzoyl-6-O-benzyl-4-O-[2,3,6-tri-O-acetyl-4-O-(2,3,4,6-tetra-O-acetyl-α-D-galactopyranosyl)-α- and β-D-galactopyranosyl]-β-D-glucopyranoside (62 and 60)

A solution of 49$^{21g}$ (2.7 g, 4 mmol) in dichloromethane (10 ml) was added at −78° to a solution of 56 (5.85 g, 10 nmol), silver trifluoromethanesulfonate (3.08 g, 12 mmol), and tetramethylurea (14 g, 12 mmol) in dichloromethane (15 ml). The mixture was treated as for the preparation of 57. Chromatography (SiO$_2$, ethyl acetate:isooctane 2:1) gave 62 (1.59 g, 34%) and a later fraction containing 60 (0.52 g, 11%). Recrystallization of 60 from abs. ethanol gave an analytical sample.

Compound 62 was amorphous with [α]$_D^{21}$ +122° (c 1.3, chloroform). $^1$H-NMR (CDCl$_3$, Me$_4$Si) δ 7.98–7.84 (4H), 7.58–7.30 (10H), 5.73 (t, 1H, J=9 Hz, H3), 5.51 (bd, 1H, J~2.5 Hz, H4″), 5.40–5.25 (3H), 5.19 (dd, 1H, J=11 and 3.5 Hz, H2″), 5.16 (dd, 1H, J=11 and 3.5 Hz, H2′), 5.02 (dd, 1H, J=11 and 2.5 Hz, H3′), 4.90 (d, 1H, J=3.5 Hz, H1″), 4.79 (d, 1H, J=8 Hz, H1), 4.74, 4.62 (ABq, 2H, J$_{AB}$=12.5 Hz, CH$_2$—Ph), 4.50–3.72 (13H), 3.42 (bt, 2H, J=7 Hz, CH$_2$Br), 2.12, 2.11, 2.04, 2.02, 1.97, 1.96, 1.75 (7s, each 3H, MeCO). $^{13}$C-NMR (CDCl$_3$, Me$_4$Si) δ 170.5, 170.4, 170.2, 170.15, 170.1, 169.9, 169.5, 165.6, 165.2, 137.8, 133.4, 133.1, 129.7 (2C), 129.6 (2C), 129.2, 129.0, 128.5 (4C), 128.2 (2C), 127.8, 127.6 (2C), 100,8 (d, J=164 Hz, Cl), 99.5 (d, J=172 Hz, Cl″), 97.0 (d, J=175 Hz, Cl′), 78.1, 74.9, 74.8, 74.1, 73.3 (CH$_2$), 71.8, 69.5 (CH$_2$), 69.2, 68.8, 68.7 (CH$_2$), 68.3, 67.7, 67.3, 66.8, 66.3, 62.3 (CH$_2$), 60.3 (CH$_2$), 29.6 (CH$_2$Br), 20.9, 20.7, 20.67, 20.6 (3C), 20.2.

Compound 60 had mp 189°–192°, [α]$_D^{21}$ +65° (c 0.5, chloroform). $^1$H-NMR (CDCl$_3$, Me$_4$Si) δ 8.07–7.91 (4H), 7.58–7.25 (11H), 5.65 (t, 1H, J=9.5 Hz, H3), 5.58 (bd, 1H, J=3 Hz, H4″), 5.41 (dd, 1H, J=9.5 and 8 Hz, H2), 5.24 (dd, 1H, J=11 and 3 Hz, H3″), 5.06 (dd, 1H, J=11 and 3.5 Hz, H2″), 5.04 (dd, 1H, J=11 and 8 Hz, H2′), 4.85 (d, J=3.5 Hz, H1″), 4.78, 4.56 (ABq, 2H, J$_{AB}$=12 Hz, CH$_2$—Ph), 4.73 (d, 1H, J=8 Hz, H1), 4.52 (dd, 1H, J=11 and 2.5 Hz, H3′), 4.49 (d, 1H, J=8 Hz, H1′), 4.41 (bt, 1H, J=7 Hz, H5″), 4.30–4.00 (5H), 3.96–3.54 (6H), 3.50–3.30 (3H), 3.41 (bt, 2H, J=7 Hz, CH$_2$Br), 2.11, 2.07, 2.04, 2.02, 1.97, 1.93, 1.88 (7s, each 3H, MeCO). $^{13}$C-NMR (CDCl$_3$, Me$_4$Si) δ 170.7, 170.6, 170.5, 170.1, 170.0, 169.4, 168.6, 165.3, 164.9, 137.8, 133.1, 132.7, 129.8–127.9, 101.2, 100.7 (2d, J=161 and 160 Hz, Cl and Cl′), 99.4 (d, J=172 Hz, Cl″), 77.2, 77.17, 76.0, 75.0, 73.8, 73.1, 72.9, 71.7, 71.6, 69.5, 68.8, 68.7, 67.8, 67.3, 66.9, 60.8, 60.3, 29.6 (CH$_2$Br), 21.0–20.5.

Anal. Calc. for C$_{55}$H$_{63}$O$_{25}$Br: C, 54.86; H, 5.27. Found C, 54.84; H, 5.28.

2-(2-Methoxycarbonylethylthio)ethyl 2,3,6-tri-O-acetyl-4-O-[2,3,6-tri-O-acetyl-4-O-(2,3,4,6-tetra-O-acetyl-α-D-galactopyranosyl)-β-D-galactopyranosyl]-β-D-glucopyranoside (63)

A mixture of 59 (3.09 g, 3 mmol), methyl 3-mercaptopropionate$^{48}$ (0.72 g, 6 mmol), cesium carbonate (1,2 g, 3.7 mmol), and N,N-dimethylformamide (15 ml) was stirred at room temperature for 1.5 h and then partitioned between dichloromethane (100 ml) and water (25 ml). The organic phase was washed with water (20 ml), dried (Na$_2$SO$_4$) and concentrated. Chromatography (SiO$_2$, ethyl acetate:isooctane 2:1) gave 63 (2.81 g, 87%) as an amorphous solid with [α]$_D^{21}$ +36° (c 1.1 chloroform). $^1$H-NMR (CDCl$_3$, Me$_4$Si) δ 5.59 (dd, 1H, J=3 and 1 Hz, H4″), 5.40 (dd, 1H, J=11 and 3 Hz, H3″), 5.21 (t, 1H, J=9 Hz, H3), 5.18 (dd, 1H, J=11 and 3.5 Hz, H2″),5.11 (dd, 1H, J=11 and 8 Hz, H2′), 4.99 (d, 1H, J=3.5 Hz, H1″), 4.90 (dd, 1H, J=9.5 and 8 Hz, H2), 4.73 (dd, 1H, J=11 and 2.5 Hz, H3′), 4.53 (d, 2H, J=8 Hz, H1 and H1′), 3.71 (s, 3H, MeO), 2.81 and 2.62 (2bt, each 2H, J~7 Hz, S—CH$_2$—CH$_2$CO), 2.71 (t, 2H, J=7 Hz, CH$_2$—S), 2.14, 2.13, 2.09, 2.08 (4s, each 3H). 2.07 (s, 6H), 2.06, 2.06, 2.05, 1.99 (4s, each 3H). $^{13}$C-NMR (CDCl$_3$, Me$_4$Si) δ 172.1, 170.5, 170.3 (3C), 170.2, 169.9 169.5, 169.4, 169.3, 168.7, 100.9, 100.4 (2d, J=164 Hz, Cl and Cl′), 99.4 (d, J=174 Hz, Cl″), 76.8, 76.2, 72.8, 72.6, 72.4, 71.6, 71.4, 69.5 (CH$_2$), 68.8, 68.6, 67.7, 66.9, 66.88, 62.0 (CH$_2$), 61.2 (CH$_2$), 60.1 (CH$_2$), 51.6 (MeO), 34.5 (CH$_2$), 31.2 (CH$_2$), 27.1 (CH$_2$), 20.8, 20.7, 20.6, 20.54 (2C), 20.5 (2C), 20.47, 20.4, 20.3.

2-(2-Methoxycarbonylethylthio)ethyl 4-O-[4-O-[(α-D-galactopyranosyl)-β-D-galactopyranosyl]-β-D-glucopyranoside (64)

A solution of 63 (1.07 g, 1.0 mmol) in methanolic sodium methoxide (0.003M, 40 ml) was left at room temperature for 42 h. The reaction was monitored by TLC (SiO$_2$, chloroform:methanol:water 65:35:10, lower phase). Crystalline 64 was filtered off, washed with methanol and dried to give pure 64 (412 mg). The filtrate was neutralized with Duolite C26 (H+) resin solvent was removed. The residue was crystallized from methanol to give a second crop of 64 (182 mg) as needles (total yield of 64: 594 mg, 97%) with mp 115°-118°, $[α]_D^{21}$+54°, (c 0.8, water). $^1$H-NMR (DMSO-d$_6$, 50°, D$_2$O added Me$_4$Si), δ 4.82, 4.29, 4.26 (3d, each 1H, J=3.5, 7 and 8 Hz, H1″, H1, H1′), 3.62 (s, 3H, MeO). $^{13}$C-NMR (D$_2$O, TSP) δ 178.0, 106.0. 104.8 (2d, J=163 and 160 Hz, Cl, Cl′), 103.0 (d, J=170 Hz, Cl″), 81.3, 80.1, 78.2, 77.6, 77.1, 75.6, 74.9, 73 6, 73.5, 71.8, 71.7 (CH$_2$), 71.66, 71.3, 63.2 (CH$_2$), 63.1 (CH$_2$), 62.8 (CH$_2$), 55.0 (MeO), 36.9 (CH$_2$), 33.5 (CH$_2$), 29.2 (CH$_2$).

Anal. Calc. for C$_{24}$H$_{42}$O$_{18}$S: C, 44.30; H, 6.50. Found: C, 43.41; H, 6.71.

2-( Octadecylthio)ethyl 2,3,6-tri-O-acetyl-4-O-[2,3,6-tri-O-acetyl-4-O-(2,3,4,6-tetra-O-acetyl-α-D-galactopyranosyl)-β-D-galactopyranosyl]-β-D-glucopyranoside (65)

A mixture of 59 (650 mg, 0.63 mmol), octadecylthiol ( 360 mg, 1.26 mmol), cesium carbonate (250 mg, 0.77 mmol) and N,N-dimethylformamide (3 ml) was stirred at room temperature for 78 h. The reaction was monitored by TLC (SiO$_2$, ethyl acetate:isooctane 3:1) The mixture was diluted with dichloromethane (50 ml), washed with water (2×25 ml), dried (Na$_2$SO$_4$), and concentrated. Column (5×18 cm) chromatography (SiO$_2$, toluene and toluene:ethyl acetate 1:1) gave amorphous 65 (677 mg, 87%) with $[α]_D^{21}$+33°(c 1.0, chloroform). $^1$H-NMR (CDCl$_3$, Me$_4$Si) δ 5.59 (dd, 1H, J=3 and 1 Hz, H4″), 5.40 (dd, 1H, J=11 and 3 Hz, H3″), 5.22 (t, J=9 Hz, H3), 5.18 (dd, 1H, J=11 and 3.5 Hz, H2″), 5.11 (dd, 1H, J=11 and 8 Hz, H2′), 4.99 (d, 1H, J=3.5 Hz, H1″), 4.90 (dd, 1H, J=9.5 and 8 Hz, H2), 4.73 (dd, 1H, J=11 and 2.5 Hz, H3′), 4.52 (d, 2H, J=8 Hz, H1 and H1′), 4.58-4.39 (5H, inter alia H1 and H1′), 4.25-3.48 (1OH), 2.68, 2.51 (2t, each 2H, J=7 Hz, CH$_2$—S—CH$_2$), 2.13, 2.12, 2.08, 2.08, 2.07, 2.07, 2.06, 2.054, 2.049, 1.99 (10s, each 3H, MeCO), 1.65-1.02 (32H), 0.88 (t, 3H, J=6.5 Hz, CH—CH ). $^{13}$C-NMR (CDCl$_3$, Me$_4$Si) δ 170.7, 170.5 (3C), 170.1, 169.7, 169.6, 169.5, 168.9, 101.1, 100.6 (2d, J=164 and 162 Hz, Cl, Cl′), 99.6 (d, J=175 Hz, Cl″), 76.9, 76.5, 73.1, 72.8, 72.6, 71.8, 71.6, 69.8 (CH$_2$), 68.9, 68.8, 67.9, 67.1, 67.0, 62.2 (CH$_2$), 61.3 (CH$_2$), 60.3 (CH$_2$), 32.6-22.7 (CH$_2$), 21.0-20.5 (CH$_3$CO), 14.1 (CH$_3$).

2-(Octadecylthio)ethyl 4-O-[4-O-(α-D-galactopyranosyl)-β-D-galactopyranosyl]-β-D-glucopyranoside (66)

A solution of 65 (1.0 g, 0.81 mmol) in methanolic sodium methoxide (0.003M, 100 ml) was left at room temperature for 24 h and neutralized with Duolite C26 (H+) resin. The solvent was removed and the residue was dissolved in water (300 ml) and lyophilized to give 66 (580 mg, 88%) with $[α]_D^{21}$+42° (c 0.7, dimethylsulfoxide). $^1$H-NMR (DMSO-d$_6$, 50°, D$_2$O added, Me$_4$Si) δ 4.81 (d, 1H, J=3.5 Hz, H1″), 4.27, 4.24 (2d, each 1H, J=7 and 8 Hz, H1 and H1′), 2.67, 2.52 (2t, each 2H, J=7.5 Hz, CH$_2$—S—CH$_2$), 0.86 (t, 3H, J=6.5 Hz, Me). $^{13}$C-NMR (CDCl$_3$—CD$_3$OD 1:5) δ 105.2, 104.1 (2d, J=162 Hz, Cl, Cl′), 102.6 (d, J=172 Hz, Cl″), 81.1, 80.0, 76.3 (3C), 74.6, (2C), 72.9, 72.5, 71.1, 70.9, 70.4, 70.3 (CH$_2$), 62.7 (CH$_2$), 62.0 (CH$_2$), 61.3 (CH$_2$), 33.2-29.7 (CH$_2$), 23.5 (CH$_2$), 14.4 (CH$_3$).

Ethyl 2,3,6-tri-O-acetyl-4-O-[2,3,6-tri-O-acetyl-4-O-(2,3,4,6-tetra-O-acetyl-α-D-galactopyranosyl)-β-D-galactopyranosyl]-β-D-glucopyranoside (67)

A solution of 59 (0.52 g, 0.5 mmol) in methanolic sodium methoxide (0.007M, 40 ml) was left at room temperature for 2 h and sodium hydroxide (95 mg) in water (2 ml) was added. The mixture was hydrogenated (atm. pressure, Pd/C, 10%, 100 mg) for 100 min, filtered, neutralized with M hydrochloric acid and the solvent was removed. The residue was acetylated (acetic anhydride-pyridine 1:1, 100 ml) for 17 h at room temperature and then co-concentrated with toluene. The residue wa partitioned between dichloromethane (100 ml) and water (25 ml) and the organic phase was dried (Na$_2$SO$_4$) and concentrated. Column (5×18 cm) chromatography (SiO$_2$, ethyl acetate:isooctane 2:1) gave amorphous 67 (300 mg, 62%) with $[α]_D^{21}$+41° (c 1.0 chloroform). $^1$H-NMR (CDCl$_3$, Me$_4$Si) δ 5.91 (d, 1H, J=3 Hz, H4″), 5.40 (dd, 1H, J=11 and 3 Hz, H3″), 5.21 (t, 1H, J=9 Hz, H3), 5.18 (dd, 1H, J=11 and 3.5 Hz, H2″), 5.11 (dd, 1H, J=11 and 8 Hz, H2′), 4.99 (d, 1H, J=3.5 Hz, H1″), 4.88 (dd, 1H, J=9 and 8 Hz, H2), 4.73 (dd, 1H, J=11 and 2.5 Hz, H3′), 4.56-4.38 (5H, inter alia H1 and H1′), 4.23-4.03 (4H), 4.02 (d, 1H, J=2.5 Hz, H4′), 3.98-3.70 (3H), 3.69-3.46 (2H), 2.14-1.98 (MeCO), 1.19 (t, 3H, J=7 Hz, CH$_3$—CH$_2$). $^{13}$C-NMR (CDCl$_3$, Me$_4$Si) δ 170.4, 170.3 (4C), 169.9, 169.6, 169.5, 169.4, 168.7, 100.9, 100.1 (2d, J=160 and 164 Hz, Cl, Cl′), 99.4 (d, J=172 Hz, Cl″), 76.8, 76.3, 73.0, 72.6, 72.3, 71.6, (2C), 68.8, 68.6, 67.7, 66.9, 66.9, 65.4 (CH$_2$), 62.1 (CH$_2$), 61.2 (CH$_2$), 60.1 (CH$_2$), 20.8, 20.7, 20.54 (3C), 20.5 (2C), 20.46, 20.4, 20.3, 14.9.

Ethyl 4-O-[4-O-(α-D-galactopyranosyl)-β-D-galactopyranosyl]-β-D-glucopyranoside (68)

A solution of 67 (440 mg, 0.46 mmol) in methanolic sodium methoxide (0.005M, 40 ml) was left at room temperature for 18 h, then neutralized with Duolite C26 (H+) resin and the solvent was removed. The residue was dissolved in water and lyophilized to give 68 (245 mg, 100%) with $[α]_D^{21}$+71° (c 0.5, water) $^1$H-NMR (DMSO-d6, 50°, D2O added, Me4Si) δ 4.81 (d, 1H, J=3.5 Hz, H1''), 4.28, 4.20 (d, each 1H, J=7 and 8 Hz, H1 and H1'), 1.14 (t, 3H, J=7 Hz, CH3—CH2). $^{13}$C-NMR (D2O, TSP) δ 106.1, 104.5, 103.2 (C1, 1', 1''), 81.5, 80.2, 78.3, 77.7, 77.3, 75.8, 75.0, 73.7, 73.6, 72.0, 71.8, 71.4, 69.1 (CH2), 63.3 (CH2), 63.2 (CH2), 62.9 (CH2), 17.1. Sugar[49] and methylation[50] analysis was in agreement with the proposed structure.

Neo-glycoprotein (69)

A solution of 64 (44 mg, 0.07 mmol) and hydrazine hydrate (85%, 0.25 ml) in ethanol (2 ml) was left overnight, concentrated, dissolved in water and lyophilized. The resulting hydrazide was dissolved in dimethylsulfoxide (1 ml), then hydrogen chloride in dioxane (4M, 105 μl) and t-butylnitrite (18 μl, 0.15 mmol) in dimethylsulfoxide (0.1 ml) were added. The mixture was stirred at room temperature for 30 min and sulfamic acid (10 mg, 0.11 mmol) in dimethylsulfoxide (0.1 ml) was added. After 15 min, the reaction mixture was added dropwise and with stirring to a solution of bovine serum albumin (BSA, 65 mg, 1 μmol) in sodium tetraborate-potassium hydrogen carbonate buffer (2.5 ml, 0.08M Na2B4O7 and 0.35M KHCO3). The pH was maintained at 9.0–9.3 by additions of sodium hydroxide solution (1M). The mixture was stirred for 16 h at room temperature, dialysed (H2O, 72 h) and lyophilized to give 69. The degree of binding (number of hapten molecules per molecule of protein) was 14 as determined by the phenol-sulfuric acid method[42]. With 0.35 mmol of 64 and 1 μmol of BSA, the degree of binding was 43.

Neo-glycoprotein (70)

The above procedure was followed, using 64 (114 mg, 0.18 mmol) and the protein key-hole limpet haemocyanin (KLH, 30 mg, 0.034 μmol). This gave 70 with a degree of binding of 480, determined as above.

2,3,6-Tri-O-acetyl-6,6-di-deuterio-4-O-(2,3,4,6-tetra-O-acetyl-6,6-di-deuterio-α-D-galactopyranosyl)-α-D-galactopyranosyl-1-bromide (71) was prepared from 1,2,3,6-tetra-O-acetyl-6,6-di-deuterio-4-O-(2,3,4,6-tetra-O-acetyl-6,6-di-deuterio-α-D-galactopyranosyl)-α-D-galactopyranose [prepared from "digalacturonic acid" as described[21g] for the protio compound except for the use of sodium borodeuteride in the reduction step. Mp 153°–155°, $[\alpha]_D^{21}$ +138° (c 0.9, chloroform); NMR data were as expected] by the same method as for 49 and used directly in the next step.

2-Bromoethyl 2,3,6-tri-O-benzyl-4-O-[2,3,6-tri-O-acetyl-6,6-di-deuterio-4-O-(2,3,4,6-tetra-O-acetyl-6,6-di-deuterio-α-D-galactopyranosyl)-β-D-galactopyranosyl]-β-D-glucopyranoside (72), was prepared from 71 and 54 as described for 57. 72 had mp 155°–157°, $[\alpha]_D^{21}$ +58° (c 0.7, chloroform) and NMR data as expected.

2-Bromoethyl 4-O-[2,3,6-tri-O-acetyl-6,6-di-deuterio-4-O-(2,3,4,6-tetra-O-acetyl-6,6-di-deuterio-α-D-galactopyranosyl)-β-D-galactopyranosyl]-β-D-glucopyranoside (73) was prepared from 72 as described for 58. 73 had mp 177°–179°, $[\alpha]_D^{21}$ +78° (c 0.5, chlororform) and NMR data as expected.

2-Bromoethyl 2,3,6-tri-O-acetyl-4-O-[2,3,6-tri-O-acetyl-6,6-di-deuterio-4-O-(2,3,4,6-tetra-O-acetyl-6,6-di-deuterio-α-D-galactopyranosyl)-β-D-galactopyranosyl]-β-D-glucopyranoside (74) was prepared from 73 as described for 59. 74 had mp 181°–183°, $[\alpha]_D^{21}$ +44° (c 0.9, chloroform) and NMR data as expected.

EXAMPLES 75–90 (see FIG. 8)

2-Bromoethyl 3,6-di-O-benzyl-2-deoxy-2-phthalimido-4-O[2,3,6-tri-O-acetyl-4-O-(2,3,4,6-tetra-O-acetyl-α-D-galactopyranosyl)-β-D-galactopyranosyl]-β-D-glucopyranoside (76)

Compound 75 (4.56 g, 7.65 mmol), tetramethylurea (1.74 g, 15 mmol) and silver trifluoromethanesulfonate (3.5 g, 13.62 mmol) were dissolved in dichloromethane (30 ml) and cooled (0°). 49 (8.25 g, 11.8 mmol) in dichloromethane (13 ml) was added with stirring. The mixture was protected from light, stirred at 0° for 2 h and at room temperature for 22 h. Solids were removed by filtration through Celite and the filtrate was diluted with dichloromethane, washed with M hydrochloric acid and aqueous sodium hydrogencarbonate, dried (Na2SO4) and concentrated. The residue (12 g) was chromatographed (SiO2-column, 5×18 cm, toluene-ether 1:2) to give 76 (3.8 g, 41%). crystallization from methanol gave material (2.81 g) with mp 98°–101°, $[\alpha]_D^{21}$ +65° (c 0.7, chloroform). $^1$H-NMR (CDCl3, Me4Si) δ inter alia 7.85–7.60 (bs, 4H), 7.50–7.30 (5H), 6.94–6.79 (3H), 5.54 (bd, 1H, J=3 Hz, H4''), 5.26 (d, 1H, J=11 and 3 Hz, H3''), 5.17–5.15 (3H, H1, H2' and H2''), 4.94 (d, 1H, J=3 Hz, H1''), 4.90 (d, 1H, J=12.5 Hz, PhCH2), 4.80 (d, 1H, J=12 Hz, PhCH2), 4.67 (dd, 1H, J=10.5 and 3 Hz, H3''), 4.64 (d, 1H, J=8 Hz, H1'), 4.052 (d, 1H, J=12 Hz, PhCH2), 4.44 (d, 1H, J=12.5 Hz, PhCH2), 3.29 (bt, 2H, J~6 Hz, CH2Br), 2.10, 2.09, 2.05, 2.02, 2.01, 1.91, 1.82 (6s, each 3H, MeCO). $^{13}$C-NMR (CDCl3, Me4Si) δ 170.5, 170.4, 170.3, 170.2, 170.0, 169.3, 168.8, 168.0, 128.5–123.1, 100.5 (d, J=164 Hz), 99.3 (d, J=172 Hz, C1''), 98.4 (d, J=163 Hz), 78.3, 77.1, 76.9, 74.7, 74.5 (CH2), 73.5 (CH2), 72.7, 71.6, 69.2 (2C, CH2), 68.2, 67.7, 67.4 (CH2), 67.1, 66.9, 61.2 (CH2), 60.2 (CH2), 55.4 (C2), 29.9 (CH2Br), 20.9, 20.6 (3C), 20.5 (2C), 20.3.

Anal. Calc. for C56H65BrNO24: C, 55.31; H, 5.39. Found: C, 55.22; H, 5.41.

2-Bromoethyl-2-deoxy-2-phthalimido-4-O-[2,3,6-tri-O-acetyl-4-O-(2,3,4,6-tetra-O-acetyl-α-D-galactopyranosyl)-β-D-galactopyranosyl]-β-D-glucopyranoside (77)

Compound 76 (5.0 g, 4.1 mmol) was hydrogenated (10% Pd/C, 1.0 g, 2 atm.) in acetic acid (50 ml) for 17 h and the mixture was filtered, concentrated and dried (oilpump) to give 77 (3.9 g, 92%) as a colorless, amorphous solid with $[\alpha]_D^{21}$ +49° (c 1.5, chloroform). $^1$H-NMR (CDCl3, Me4Si) δ inter alia 7.96–7.81 (2H), 7.80–7.68 (2H), 5.58 (dd, 1H, J=3 and 1 Hz, H4''), 5.39 (d, 1H, J=8.5 Hz, H1), 5.34 (dd, 1H, J=11 and 3 Hz, H3''), 5.25 (dd, 1H, J=11 and 8 Hz, H2'), 5.19 (dd, 1H, J=11 and 3.5 Hz, H2''), 4.93 (d, 1H, J=3.5 Hz, H1''), 4.79 (dd, 1H, J=11 and 2.5 Hz, H3'), 4.68 (d, 1H, J=8 Hz, H1'), 3.34 (t, 2H, J=6 Hz, CH2Br), 2.13 (6H), 2.10, 2.08, 2.05, 1.97, 1.86. $^{13}$C-NMR (CDCl3, Me4Si) δ 170.6, 170.5 (2C), 170.4, 170.1, 169.8, 169.1, 168.0 (broad, 2C), 134.0 (2C) 131.7 (2C), 123.3 (2C), 101.9 (d, J~167 Hz, C1 or C1'), 99.8 (d, J=174 Hz, C1''), 98.4 (d, J~163 Hz, C1 or C1'), 82.2, 77.3, 74.2, 72.7, 72.5, 69.7, 69.6, 68.43, 68.38, 67.7, 67.4, 67.2, 62.5 (CH2), 60.8 (CH2), 60.4 (CH2), 55.6 (C2), 29.9 (CH2Br), 20.9 (2C), 20.8, 20.6 (3C), 20.2.

2-Bromoethyl 3,6-di-O-acetyl-2-deoxy-2-phthalimido-4-O-[2,3,6-tri-O-acetyl-4-O-(2,3,4,6-tetra-O-acetyl-α-D-galactopyranosyl)-β-D-galactopyranosyl]-β-D-glucopyranoside (78)

Compound 77 (3.76 g, 3.6 mmol) was acetylated (acetic anhydride-pyridine 1:1, 50 ml) at room temperature for 18 h and then co-evaporated with toluene. Crystallization from ethanol gave 78 (3.64 g, 90%) with mp 227°–229°, $[\alpha]_D^{21}$ +50° (c 0.8, chloroform). $^1$H-NMR (CDCl$_3$, Me$_4$Si) δ 7.92–7.81 (2H), 7.80–7.64 (2H), 5.76 (dd, 1H, J=10.5 and 8 Hz, H3), 5.59 (bdd, 1H, J=3 and 1 Hz, H4″), 5.44 (d, 1H, J=8.5 Hz, H1), 5.38 (dd, 1H, J=11 and 3 Hz, H3″), 5.17 (dd, 1H, J=11 and 3.5 Hz, H2″), 5.13 (dd, 1H, J=11 and 8 Hz, H2′), 4.98 (d, 1H, J=3.5 Hz, H1″), 4.74 (dd, 1H, J=11 and 2.5 Hz, H3′), 4.58 (d, 1H, J=8 Hz, H1′), 4.64–3.70 (15H, inter alia H1′), 3.34 (bt, 2H, J~6 Hz, CH$_2$Br), 2.15, 2.12, 2.07 (9H), 2.06 (6H), 2.04, 1.96. $^{13}$C-NMR (CDCl$_3$, Me$_4$Si) δ 170.7, 170.52, 170.48 (2C), 170.4, 170.1, 169.7, 169.5, 168.9, 167.9 (broad, 2C), 134.2 (2C), 131.6, 131.5, 123.5 (2C), 101.0 (d, J=160 Hz, Cl′), 99.6 (d, J=171 Hz, Cl″), 98.1 (d, J=166 Hz, Cl), 76.9, 76.8, 72.7, 72.6, 71.6, 71.4, 69.8 (CH$_2$CH$_2$Br), 69.0, 68.8, 67.9, 67.1 (2C), 62.2 (CH$_2$), 61.1 (CH$_2$), 60.2 (CH$_2$), 54.7 (C-2), 29.8 (CH$_2$Br), 21.0, 20.9, 20.8, 20.7 (3C), 20.6, 20.5, 20.4.

Anal. Calc. for C$_{46}$H$_{56}$BrNO$_{26}$: C, 49.38; H, 5.05. Found: C, 49.50; H, 5.08.

2-(2-Methoxycarbonylethylthio)ethyl 3,6-di-O-acetyl-2-deoxy-2-phthalimido-4-O-[2,3,6-tri-O-acetyl-4-O-(2,3,4,6-tetra-O-acetyl-α-D-galactopyranosyl)-β-D-galactopyranosyl]-β-D-glucopylanoside (79)

Compound 78 (3.91 g, 3.5 mmol), methyl 3-mercaptopropionate[55] (0.84 g, 7.0 mmol), cesium carbonate (1.30 g, 4.0 mmol) and N,N-dimethylformamide (15 ml) were stirred at room temperature for 2.5 h. The reaction was monitored by TLC (SiO$_2$, ethyl acetate:isooctane, 3:1). Dichloromethane (100 ml) was added and the mixture was washed with water (50 ml). The aqueous phase was extracted with dichloromethane (25 ml) and the combined organic phases were washed with water (20 ml), dried (Na$_2$SO$_4$) and concentrated. The residue was crystallized from methanol to give 79 (3.80 g, 94%) with mp 151°–153° (phase transition starting at 118°), $[\alpha]_D^{21}$ +52° (c 0.7, chloroform). $^1$H-NMR (CDCl$_3$, Me$_4$Si) δ inter alia 7.96–7.74 (4H), 5.74 (m, 1H, H3), 5.58 (dd, 1H, J=3 and 1 Hz, H4″), 5.42 (d, 1H, J=8.5 Hz, H1), 5.38 (dd, 1H, J=11 and 3.5 Hz, H3″), 5.17 (dd, 1H, J=11 and 3.5 Hz, H2″), 5.13 (dd, 1H, J=11 and 8 Hz, H2′), 4.98 (d, 1H, J=3.5 Hz, H1″), 4.74 (dd, 1H, J=11 and 2.5 Hz, H3′), 4.59 (d, 1H, J=8 Hz, H1′), 3.67 (s, 3H, CH$_3$O), 2.70–2.56 (4H, CH$_2$S), 2.42 (bt, 2H, J 7 Hz, CH$_2$S), 2.15, 2.12, 2.07 (6H), 2.064, 2.059, 2.04, 1.96, 1.95. $^{13}$C-NMR (CDCl$_3$, Me$_4$Si) δ 172.1, 170.7, 170.5 (2C), 170.4, 170.0, 169.7, 169.5, 168.9, 167.8 (2C), 134.2 (2C), 134.15 (2C), 123.5 (2C), 101.0 (Cl′ or Cl), 99.6 (Cl″), 98.0 (Cl or Cl′), 77.0, 76.8, 72.7, 72.6, 71.6, 71.5, 69.5 (OCH$_2$CH$_2$), 69.0, 68.8, 67.9, 67.0, 62.3 (CH$_2$), 61.1 (CH$_2$), 60.2 (CH$_2$), 54.8 (C2), 51.8 (OCH$_3$), 34.5 (CH$_2$), 31.3 (CH$_2$), 27.1 (CH$_2$), 21.0, 20.9, 20.74, 20.69, 20.66, 20.64, 20.6, 20.5, 20.4.

Anal. Calc. for C$_{50}$H$_{63}$NO$_{28}$S: C, 51.05; H, 5.48. Found: C, 51.70; H, 5.41.

2-(Octadecylthio)ethyl 3,6-di-O-acetyl-2-deoxy-2-phthalimido-4-O-[2,3,6-tri-O-acetyl-4-O-(2,3,4,6-tetra-O-acetyl-α-D-galactopyranosyl)-β-D-galactopyranosyl]-β-D-glucopyranoside (80)

Compound 78 (1.68 g, 1.5 mmol), octadecanethiol (0.81 g, 2.8 mmol), cesium carbonate (0.50 g, 1.53 mmol) and N,N-dimethylformamide (11 ml) were stirred at room temperature for 7.5 h and worked up as above for 79. The resulting residue was chromatographed (SiO$_2$-column, 5×18 cm; ethyl acetate:isooctane 2:1 followed by 4:1 and finally ethyl acetate) to give 80 (1.80 g, 91%). Crystallization from methanol gave an analytical sample with mp 150°–152°, $[\alpha]_D^{21}$ +47° (c 0.6, chloroform). $^1$H-NMR (CDCl$_3$, Me$_4$Si) δ 7.93–7.72 (4H), 5.75 (m, 1H, H3), 5.58 (bd, 1H, J~3 Hz, H4″), 5.42 (d, 1H, J=8 Hz, H1), 5.38 (dd, 1H, J=11 and 3.5 Hz, H2″), 5.16 (dd, 1H, J=11 and 3.5 Hz, H3″), 5.13 (dd, 1H, J=11 and 8 Hz, H2′), 4.98 (d, 1H, J=3.5 Hz, H1″), 4.74 (dd, 1H, J=11 and 2.5 Hz, H3′), 4.63–4.34 (4H, inter alia H1′), 4.58 (d, 1H, J=8 Hz, H1′), 4.29–3.57 (11H), 2.55 (t, 2H, J=7 Hz, CH$_2$S), 2.31 (t, 2H, J=7 Hz, CH$_2$S), 2.15, 2.12, 2.07 (6H), 2.064, 2.058, 2.04, 1.96, 1.95, 1.40–1.15 (bs), 0.88 (t, 3H, J=6.5 Hz, CH$_3$). $^{13}$C (CDCl$_3$, Me$_4$Si) δ 170.7, 170.5 (3C), 170.4 170.0, 169.7, 169.5, 168.9, 168.2 (broad, 2C), 134.2 (2C), 134.0 (2C), 123.5 (2C), 101.0 (d, J=160 Hz, Cl′ or Cl), 99.6 (d, J=173 Hz, Cl″), 98.1 (d, J=160 Hz, Cl or Cl′), 77.8, 72.7, 72.6, 71.62, 71.56, 69.7 (OCH$_2$CH$_2$), 69.0, 68.8, 67.9, 67.1 (2C), 62.4 (CH$_2$), 61.1 (CH$_2$), 60.2 (CH$_2$), 54.2 (C2), 32.4–22.7 (CH$_2$), 21.0, 20.9, 20.74, 20.68 (2C), 20.64, 20.57, 20.51, 20.45, 14.14.

Anal. Calc. for C$_{64}$H$_{93}$O$_{26}$S: C, 58.03; H, 7.08. Found: C, 57.91; H, 7.02.

2-(2-Methoxycarbonylethylthio)ethyl 2-acetamido-2-deoxy-3,6-di-O-acetyl4-O-[2,3,6-tri-O-acetyl-4-O-(2,3,4,6-tetra-O-acetyl-α-D-galactopyranosyl)-β-D-galactopyranosyl]-β-D-glucopyranoside (81)

Compound 79 was treated as 80 in the preparation of 83. The crude 81 formed was chromatographed (SiO-column, ethyl acetate:isooctane 4:1 and ethyl acetate) to give pure 81 with $[\alpha]_D^{21}$ +33°. $^1$H-NMR (CDCl$_3$, Me$_4$Si) δ inter alia 5.86 (d, 1H, J=9 Hz, NH), 5.58 (dd, 1H, J=3 and <1 Hz, H4″), 5.39 (dd, 1H, J=11 and 3 Hz, H3″), 5.19 (dd, 1H, J=11 and 3.5 Hz, H2″), 5.12 (dd, 1H, J=11 and 8 Hz, H2′), 5.11 (t, 1H, J=8.5 Hz, H3), 5.00 (d, 1H, J=3.5 Hz, H1″), 4.76 (dd, 1H, J=11 and 2.5 Hz, H3′), 4.60–4.38 (5H, inter alia H1and H1′), 3.71 (s, CH$_3$O), 2.82 (bt, 2H, J=7 Hz, SCH$_2$CH$_2$CO), 2.72 (t, 2H, J=6.5 Hz, OCH$_2$CH$_2$), 2.62 (bt, 2H, J=7 Hz, SCH$_2$CH$_2$CO), 2.13 2.12, 2.11, 2.084, 2.075 (6H), 2.06, 2.05, 1.99, 1.96 (CH$_3$CO). $^{13}$C-NMR (CDCl$_3$, Me$_4$Si) δ 172.5–169.1, 101.0 (2C, Cl and Cl′), 99.6 (Cl″), 77.0, 76.1, 72.9, 72.6, 71.9, 69.2 (OCH$_2$CH$_2$), 69.0, 68.7, 67.9, 67.1 (2C), 62.4 (CH$_2$), 61.4 (CH$_2$), 60.4 (CH$_2$), 53.4 (C2), 51.9 (CH$_3$O), 34.6 CH$_2$), 31.5 (CH$_2$), 27.3 (CH$_2$), 23.2–20.5.

2-(2-Methoxycarbonylethylthio)ethyl 2-acetamido-2-deoxy-4-O-[4-O-(α-D-galactopyranosyl)-β-D-galactopyranosyl]-β-D-glucopyranoside (82)

Compound 81 (350 mg, 0.3 mmol) was dissolved in methanol (10 ml) by warming and then rapidly cooled. Methanolic sodium methoxide (0.2M, 0.2 ml) was added and the mixture was stirred at room temperature for 18 h, neutralized (Duolite C-26 (H+) resin), filtered and concentrated. The residue was dissolved in methanol (7 ml) and methanolic hydrazine hydrate (0.1M, 3 ml) was added. The mixture was refluxed for 33 h while two additional portions (2×3 ml) were added (after 24 and 30 h). The reaction was monitored by TLC (SiO$_2$,-chloroform methanol:water 65:35:10, lower phase). The solvent was removed and the residue was treated with a mixture of acetic anhydride (2.5 ml), ethanol (12 ml), and water (4 ml) at room temperature for 1 h. The ethanol was removed and the residue was partitioned between water (20 ml) and dichloromethane (5 ml). The aqueous phase was washed with dichloromethane (3×5 ml) and concentrated. The residue was chromatographed {Sephadex G-10 column. 3×57 cm, water) to give 82 (157 mg, 75%) with $[\alpha]_D^{22}+34°$ (c 0.7, water). $^1$H-NMR [(CD$_3$)$_2$SO+D$_2$O, 50°, Me$_4$Si]$\delta$ inter alia 4.80 (d, 1H, J=3.5 Hz, H1″), 4.40 (d, 1H, J=8 Hz, H1 or H1′), 4.28 (d, 1H, J=7 Hz, H1or H1′), 4.08 (dt, 1H, J=6 and 1 Hz), 3.61 (s, CH$_3$O), 2.75–2.70 and 2.61–2.54 (m, each 2H, SCH$_2$CH$_2$CO), 2.64 (t, 2H, J=7 Hz, OCH$_2$CH$_2$S), 1.80 (s, 3H, MeCON). $^{13}$C-NMR (D$_2$O, TSP) $\delta$ 178.0, 177.3, 106.1, 103.8, 103.1, 81.6, 80.1, 78.2, 77.7, 75.3, 75.0, 73.7, 73.6, 72.1 (CH$_2$), 72.0, 71.8, 71.4, 63.3 (CH$_2$), 63.2 (CH$_2$), 62.9 (CH$_2$), 58.0 (C2), 55.2 (CH$_3$O), 37.1 (CH$_2$), 33.8 (CH$_2$), 29.4 (CH$_2$), 23.2.

2-(Octadecylthio)ethyl 2-acetamido-2-deoxy-3,6-di-O-acetyl-4-O-[2,3,6-tri-O-acetyl-4-O-(2,3,4,6-tetra-O-acetyl-α-D-galactopyranosyl)-β-D-galactopyranosyl]-β-D-glucopyranoside (83)

Compound 80 (1.46 g, 1.1 mmol) was dissolved in a mixure of methanol (75 ml) and tetrahydrofuran (10 ml) by warming. The clear solution was rapidly cooled to ~40° C. and methanolic sodium methoxide (0.2 M, 5 ml) was added. The mixture was stirred at room temperature for 5 h, after which time the deacetylation was complete. (TLC; SiO$_2$,chloroform:methanol:water 65:35:10, lower phase), neutralized by addition of acidic ion-exchange resin (Duolite C-26), filtered and evaporated. The residue was re-dissolved in refluxing methanol (50 ml) and hydrazine hydrate (0.5 g, 10 mmol) was added. The reflux was continued for 17.5 h, whereafter the solvent was evaporated. The residue was acetylated by stirring for 22 h at room temperature in a mixture of pyridine and acetic anhydride (1:1, 50 ml). After evaporation, the residue was subjected to chromatography (SiO$_2$-column, 5×18 cm, ethyl acetate: isooctane gradient: 2:1–4:1-ethyl acetate) which gave amorphous 83 (0.72 g, 52%) with $[\alpha]_D^{21}+32°$ (c 1.1, chloroform). $^1$H-NMR (CDCl$_3$, Me$_4$Si) $\delta$ 5.67 (d, 1H, J=9.5 Hz, NH), 5.58 (bd, 1H, J=3 Hz, H4″), 5.39 (dd, 1H, J=1 and 3 Hz, H3″), 5.23–5.01 (3H, H2′, H2″ and H3), 4.99 (d, 1H, J=3.5, H1″), 4.75 (dd, 1H, J=11 and 2.5 Hz, H3′) 4.58–4.37 (5H, inter alia H1and H1′), 4.54 and 4.49 (2d, each 1H, J=8 Hz each, H1 and H1′), 4.23–3.90 (7H), 3.85-3.55 (4H), 2.69 (t, 2H, J=7 Hz, OCH$_2$CH$_2$S), 2.51 (t, 2H, J=7 Hz, SCH$_2$), 2.13, 2.12, 2.11, 2.08 (4s, each 3H, MeCO), 2.075, 2.05 (2s, each 6H, MeCO), 1.99, 1.97 (2s, each 3H, MeCO), 1.66–1.20, 0.88 (t, 3H, J=6.5 Hz, CH$_3$CH$_2$). $^{13}$C-NMR (CDCl$_3$, Me$_4$Si) $\delta$ 170.6 (2C), 170.4 (3C), 170.2, 170.1, 169.6, 169.0, 101.1, 101.0 (d, J each 160 Hz, C1 and C1′), 99.6 (d, J=172 Hz, C1″), 76.9, 75.9, 72.7, 72.6 (2C), 71.8, 69.1 (OCH$_2$CH$_2$), 68.9, 68.7, 67.8, 67.1, 67.0, 62.4 (CH$_2$), 61.3 (CH$_2$), 60.2 (CH$_2$), 53.3 (C2), 32.5–28.8, 23.3 (CH$_3$CONH), 22.7 (CH$_2$), 20.9-20.5, 14.1.

2-(Octadecylthio)ethyl 2-acetamido-2-deoxy-4-O-[4-O-(α-D-galactopyranosyl)-β-D-galactopyranosyl-β-D-glucopyranoside (84)

Compound 83 (560 mg, 0.45 mmol) was dissolved in methanol (25 ml) and methanolic sodium methoxide (0.2 M, 1 ml) was added. The mixture was stirred at room temperature for 14.5 h, which gave an amorphous precipitate. This was dissolved by adding methanol (50 ml) and warming the mixture to ~40°. The solution was cooled to room temperature, neutralized with Dualite C-26 (H+) resin, filtered and concentrated. The residue was suspended in water (100 ml) and lyophilized to give amorphous 84 (340 mg, 87%) with $[\alpha]_{hd} D^{21}+35°$ (c 0.6, dimethyl sulfoxide). $^1$H-NMR [(CD$_3$)$_2$SO+D$_2$O, 50°, Me$_4$Si)]$\delta$ inter alia 4.81 (d, 1H, J=3.5 Hz, H1″), 4.40 and 4.29 (2d, each 1H, J=7.5 Hz, H1 and H1′), 2.60 (t, 2H, J=7 Hz, CH$_2$S), 2.50 (t, 2H, J=7 Hz, SCH$_2$), 1.81 (s, 3H, CH$_3$CON), 0.86 (t, 3H, J=6.5 Hz, CH$_3$CH$_2$). $^{13}$C-NMR [(CD$_3$)$_2$SO, Me$_4$Si]$\delta$ 168.7, 103.8 (d, J=162 Hz, C1 or C1′), 100.7, 100.5 (2d, J~162 and 172 Hz, C1″ and C1 or C1′), 81.2, 77.1, 75.0 (2C), 72.8, 72.1, 71.0, 70.8, 69.1, 68.7, 68.5, 68.5 (OCH$_2$CH$_2$), 60.3 (2 CH$_2$), 59.3 (CH$_2$), 54.5, 31.4-28.1 (CH$_2$),22.9, 22.1 (CH$_2$), 13.9 (CH$_3$CH$_2$).

Ethyl 2-acetamido-2-deoxy-3,6-di-O-benzyl-4-O-[2,3,6-tri-O-acetyl-4-O-(2,3,4,6-tetra-O-acetyl-α-D-galactopyranosyl)-β-D-galactopyranosyl-β-D-glucopyranoside (85)

Compound 76 (310 mg, 0.26 mmol) was hydrogenated (10% Pd/C, 0.3 g, 39 psi) in methanolic sodium methoxide (0.02M, 33 ml) at room temperature for 22 h, filtered and neutralized with Duolite C-26 (H$^{30}$) resin. The pH of the solution was adjusted to 7.5 by addition of solid sodium hydrogen carbonate and the mixture was filtered and concentrated (<1 Torr). Methanol (25 ml) and hydrazine hydrate (0.8 g, 16 mmol) were added and the mixture was refluxed for 3 h. TLC (SiO$_2$, chloroform:methanol:water 65:35:10, lower phase) showed complete conversion. The solvent was removed and the residue was acetylated (acetic anhydride:pyridine 1:1, 50 ml) at room temperature for 17 h. Co-evaporation with toluene gave a residue that was chromatographed (SiO$_2$-column 1.5×38 cm, ethyl acetate:isooctane 3:1 and finally ethyl acetate) to give crystalline 85 (151 mg, 55%). Recrystallization from isopropanol:isooctane gave an analytical sample with mp 97°–100°, $[\alpha]_D^{22}+40°$ (c 0.6, chloroform). $^1$H-NMR (CDCl$_3$, Me$_4$Si) $\delta$ 7.42–7.20 (10H), 5.93 (d, 1H, J=8 Hz, NH), 5.55 (dd, 1H, J=3 and 1 Hz, H4″), 5.32 (dd, 1H, J=11 and 3 Hz, H3″), 5.19 (dd, 1H, J=11 and 3.5 Hz, H2″), 5.14 (dd, 1H, J=11 and 8 Hz, H2′), 4.99 (d, 1H, J=3.5 Hz, H1″), 4.88–4.63 (5H), 4.58–4.44 (3H, inter alia H1 or H1′ and PhCH), 4.54 (d, 1H, J=8 Hz, H1 or H1′), 4.47 (d, 1H, J=12 Hz, PhCH), 4.31 (dd, 1H, J=11 and 6.5 Hz), 4.23–3.44, 2.13–1.92 (24H, MeCO), 1.18 (t, 3H, J=7 Hz, CH$_3$CH$_2$). $^{13}$C-NMR (CDCl$_3$, Me$_4$Si) $\delta$ 170.5 (2C), 170.4, 170.3, 170.2, 170.1, 169.6, 169.5, 138.8, 138.0, 128.4–127.3, 100.0 (d, J=165 Hz, C1 or C1′), 99.7 (d, J=163 Hz, C1 or C1′), 99.3 (d, J=172 Hz, C1″), 77.2 76.8, 75.9, 74.3, 73.5 (CH$_2$), 73.1 (CH$_2$), 72.4, 71.9, 69.0, 68.8 (CH$_2$), 68.4, 67.7, 67.2, 67.0, 64.2 (CH$_2$), 61.4 (CH$_2$), 60.4 (CH$_2$), 53.1 (C2), 23.3 (CH$_3$CONH), 20.9, 20.72, 20.69, 20.65 (2C), 20.6, 20.5, 15.0 (CH$_3$CH$_2$).

Anal Calc. for $C_{50}H_{65}NO_{23}$: C, 57.30; H, 6.25. Found C, 57.12; H, 6.27.

Ethyl 2-acetamido-2-deoxy-4-O-[2,3,6-tri-O-acetyl-4-O-(2,3,4,6-tetra-O-acetyl-α-D-galactopyranosyl)-β-D-galactopyranosyl]-β-D-glucopyranoside (86)

Compound 85 (475 mg, 0.45 mmol) was hydrogenated (10% Pd/C, 200 mg, 1 atm.) in acetic acid (10 ml) for 5.5 h at room temperature. The mixture was filtered and the solvent was removed, which gave a crystalline residue. Recrystallization from ethanol gave 86 (291 mg, 74%) with mp 260°–262°, $[α]_D^{22} + 67°$ (c 0.9, chloroform) $^1$H-NMR (CDCl$_3$+D$_2$O, Me$_4$Si) δ 5.59 (dd, 1H, J=3 and 1 Hz, H4''), 5.37 (dd, 1H, J=11 and 3 Hz, H3''), 5.23 (dd, 1H, J=11 and 8 Hz, H2''), 5.21 (dd, 1H, J=11 and 3.5 Hz, H2''), 4.96 (d, 1H, J=3.5 Hz, H1''), 4.80 (dd, 1H, J=11 and 3 Hz, H3'), 4.75 (d, 1H, J=8.5 Hz, H1), 4.68 (d, 1H, J=8 Hz, H1'), 4.51 (bt, 1H, J=7 Hz, H5''), 4.44 (dd, 1H, J=11 and 8.5 Hz), 4.28–3.40 (13H), 2.142, 2.139, 2.10, 2.084, 2.080, 2.05, 2.01, 2.00 (8s, each 3H), 1.21 (t, 3H, J=7 Hz, CH$_3$CH$_2$). $^{13}$C-NMR (CDCl$_3$, Me$_4$Si) δ 170.6, 170.5 (2C), 170.4, 170.3, 170.1, 169.9, 169.1, 101.8 (C1 or C1'), 100.2 (C1 or C1'), 99.8 (C1''), 81.8, 77.3, 73.9, 72.7, 72.6, 71.9, 68.5, 68.4, 67.8, 67.4, 67.3, 65.3, 62.5, 61.0, 60.4, 56.6 (C2), 23.6–20.5, 15.1.

Anal. Calc. for $C_{36}H_{53}NO_{23}$: C, 49.82; H, 6.16. Found: C, 50.0; H, 6.20.

Ethyl 2-acetamido-2-deoxy-3,6-di-O-acetyl-4-O-[2,3,6-tri-O-acetyl-4-O-(2,3,4,6-tetra-O-acetyl-α-D-galactopyranosyl)-β-D-galactopyranosyl]-β-glucopyranoside (87)

Compound 78 (0.65 g, 0.58 mmol) was hydrogenated (10% Pd/C, 0.31 g, 40 psi) in methanolic sodium methoxide (0.02M, 56 ml) at room temperature for 20 h, filtered and neutralized with Duolite C-26 (H$^+$) resin. The mixture was filtered and concentrated and the residue was dissolved in methanol (20 ml) and hydrazine hydrate (1.7 g, 34 mmol), refluxed for 23 h and concentrated. The residue was acetylated (acetic anhydride:pyridine 1:1 50 ml) at room temperature for 18 h. Co-concentration with toluene gave a residue that was dissolved in dichloromethane (75 ml) and washed with water (50 ml). The water phase was extracted with dichloromethane (25 ml) and the combined organic extracts were washed with water (10 ml), dried (Na$_2$SO$_4$), and concentrated. The residue was chromatographed (SiO$_2$-column, 1.5×46 cm, ethyl acetate) to give crystalline 87 (158 mg, 28%) with mp 130°–133°, $[α]_D^{22}+41°$ (c 0.7, chloroform). $^1$H-NMR (CDCl$_3$, Me$_4$Si) δ 5.73 (d, 1H, J=9.5 Hz, NH), 5.58 (bd, 1H, J~3 Hz, H4''), 5.39 (dd, 1H, J=11 and 3 Hz, H3''), 5.19 (dd, 1H, J=11 and 3.5 Hz, H2''), 5.12 (dd, 1H, J=11 and 8 Hz, H2'), 5.10 (dd, 1H, J=9.5 and 8 Hz, H3), 5.00 (d, 1H, J=3.5 Hz, H1''), 4.76 (dd, 1H, J=11 and 2.5 Hz, H3'), 4.58–4.37 (5H, inter alia H1, H1'), 4.55 (d, 1H, J=8 Hz, H1 or H1'), 4.46 (d, 1H, J=7.5 Hz, H1 or H1'), 4.23–3.96 (6H), 3.95–3.73 (3H), 3.71–3.45 (2H), 2.14, 2.11, 2.106, 2.084, 2.079, 2.076, 2.06, 2.05, 1.99, 1.97, 1.19 (t, 3H, J=7 Hz, CH$_3$CH$_2$). $^{13}$C-NMR (CDCl$_3$, Me$_4$Si) δ 170.6 (2C), 170.51, 170.46 (2C), 170.4, 170.3, 170.1, 169.7, 169.1, 101.1 (d, J=164 Hz, C1 or C1'), 100.7 (d, J=160 Hz, C1 or C1'), 99.6 (d, J=174 Hz, C1''), 77.0, 76.1, 72.8, 72.7, 72.5, 71.9, 69.0, 68.7, 67.9, 67.1 (2C), 65.0 (CH$_2$), 62.5 (CH$_2$), 61.4 (CH$_2$), 60.3 (CH$_2$), 53.4 (C2), 23.2–20.5, 15.1 (CH$_3$CH$_2$).

Anal. Calc. for $C_{40}H_{57}NO_{25}$: C, 50.47; H, 6.04. Found: C, 50.31; H, 6.02.

Ethyl 2-acetamido-2-deoxy-4-O-[4-O-(α-D-galactopyranosyl)-β-D-galactopyranosyl]-β-D-glucopyranoside (88)

a: Compound 87 (58 mg, 0.06 mmol) was O-deacetylated in methanolic sodium methoxide (0.036M, 5.5 ml) at room temperature for 21 h. The mixture was neutralized with Duolite C-26 (H) resin, filtered and concentrated. The residue was dissolved in water and lyophilized to give 88 (21 mg, 60%) with $[α]_D^{22}+25°$ (c 0.7, water). $^1$H-NMR [(CD$_3$)$_2$SO+D$_2$O, 50°, Me$_4$Si] δ inter alia 4.80 (d, 1H, J=3.5 Hz, H1''), 4.37 (d, 1H, J=8 Hz, H1 or H1'), 4.29 (d, 1H, J=7.5 Hz, H1 or H1'), 4.07 (bt, 1H, J~6.5 Hz), 1.81 (s, 3H, MeCON), 1.08 (t, 3H, J=7 Hz, CH$_3$CH$_2$). $^{13}$C-NMR (D$_2$O, TSP) δ 177.4, 106.1, 103.4, 103.1, 81.6, 80.1, 78.2, 77.7, 75.4, 75.0, 73.7, 73.6, 72.0, 71.7, 71.4, 69.1 (CH$_2$), 63.3 (CH$_2$), 63.2 (CH$_2$), 62.9 (CH$_2$), 58.1, 25.0, 17.1. b: Compound 86 (15 mg, 0.017 mmol) was O-deacetylated and worked-up as above to give 88 (8.0 mg, 81%).

Neoglycoproteins 89 and 90

Compound 82 (40 mg) was treated as 64 in the preparation of 69 and coupled to bovine serum albumin (BSA, 60 mg) to give 89. The degree of binding was 17. Another portion of 82 (120 mg) was treated as 64 in the preparation of 70 and coupled to key-hole limpet haemocyanin (KLH, 35 mg) to give 90. The degree of binding was 420.

EXAMPLES 91–102

Pullulan was prepared as described[52] and purified by two precipitations from water by addition of isopropanol (200 g pullulan, 4 l water and 13 l isopropanol). Pullulanase and β-amylase are commercially available (Sigma Chemical Company). Optical rotations were obtained using a Perkin-Elmer 241 polarimeter. NMR spectra were recorded on a Varian XL-200 spectrometer with tetramethylsilane (TMS) or sodium 3-(trimethylsilyl)-propionate-d$_4$ (TSP) as reference. NMR assignments are based double resonance and INEPT[37] experiments.

4-O-{4-O-[6-O-(α-D-glucopyranosyl)-α-D-glucopyranosyl]-α-D-glucopyranosyl}-D-glucose (91)

Pullulane[52] (100 g) was dissolved in water (1 l) by heating and added to a solution of acetic acid (ca 15 ml) and sodium acetate (41 g) in water (5 l). The solution was adjusted to pH 5 and pullulanase and β-amylase (200 and 200000 units respectively) were added. The reaction mixture was stirred at 37° for 24 h (TLC: SiO$_2$, acetone:isopropanol:0.1M lactic acid; 2:2:1) and then heated at 120° for 20 min (autoclave). The solution was concentrated (final volume: 1.5 l) and treated with ion-exchange resin (Duolite C-26 (H$^+$); 0.5 l). The resin was washed with water and the combined water solutions (ca 4 l) were ultrafiltered (Millipore PSAC 14205 NMWL 1000) which gave a colorless solution. Freeze-drying gave 91 (72 g) contaminated with glucose, maltose and maltotriose. Pure 91 was obtained by treating 92 (1.0 g) with methanolic sodium methoxide (50 ml; from ~1 mg of sodium) at room temperature while monitoring the reaction by TLC (SiO$_2$, chloroform:methanol:water 65:35:10, lower phase). After 24 h, the reaction mixture was neutralized with dry Duolite (H+) resin, filtered, concentrated and chromatographed (Waters Preppak-500/C:water) to give 91 (337 mg, 63%, >99.5% pure by HPLC). $[\alpha]_D^{25}+165°$ (c 0.8, water). Lit.[25] $[\alpha]_D^{20}+179°$ (c 1.14, water). $^1$H-NMR (D$_2$O, TSP) δ 5.40, 5.38 (2d, each 1H, J=3.8 and 3.5 Hz, H1' and H1''), 5.26 (d, ~0.3H, J=3.7 Hz, H1), 4.99 (d, 1H, J=3.7 Hz, H1'''), 4.68 (d, ~0.7H, J=7.9 Hz, H1). $^{13}$C-NMR (D$_2$O, TSP) δ 102.6, 102.2, 100.8 (C1', C1Δ, C1'''), 98.5, 94.7 (C1), 79.9, 79.8, 79.6, 78.9, 77.3, 76.7, 76.0, 75.97, 75.8, 74.7, 74.6, 74.4, 74.3, 74.2, 74.1, 73.9, 72.7, 72.3, 72.1, 68.6, 63.4, 63.3, 63.2. The structure of 91 was confirmed by methylation analysis[26].

1,2,3,6-tetra-O-acetyl-4-O-{2,3,6-tri-O-acetyl-4-O-[2,3,4-tri-O-acetyl-6-O-(2,3,4,6-tetra-O-acetyl-α-D-glucopyranosyl)-α-D-glucopyranosyl]-β-D-glucopyranosyl}-β-D -glucopyranose (92)

Compound 91 (63.7 g, vide supra) was dissolved in acetic anhydride-pyridine (1:2; 450 ml) and left at room temperature for 15 h. The mixture was co-concentrated with toluene and the acetylation procedure was repeated twice. The residue was dissolved in dichloromethane and washed with hydrochloric acid (1M) and saturated, aqueous sodium hydrogen carbonate drying (Na$_2$SO$_4$) and evaporation gave a residue (112.5 g) which was chromatographed on silica gel (ethyl acetate:isooctane, 3:2) to give 92 (αβ-mixture 20.0 g, 12% from pullulan). [β-92 (>98% purity) had $[\alpha]_D+114°$ (c 0.2, chloroform)]. $^1$H-NMR (CDCl$_3$, Me$_4$Si) δ 6.25, 5.75 (2d, each 0.5H, J=3.6 and 8.0 Hz, H1). $^{13}$C-NMR (CDCl$_3$, Me$_4$Si) δ 95.8, 95.8, 95.2 (C1', C1'', C1'''), 91.2 (C1β), 88.8 (C1α), 75.0, 73.5, 73.4, 73.0, 72.8, 72.6, 72.0, 71.7, 71.6, 70.9, 70.7, 70.4, 70.1, 69.9, 69.7, 69.4, 69.3, 69.0, 68.4, 67.4, 65.3, 62.8, 62.7, 62.7, 61.8, 20.9–20.3.

2-Bromoethyl 2,3,6-tri-O-acetyl-4-O-{2,3,6-tri-O-acetyl-4-O-[2,3,4-tri-O-acetyl-6-O-(2,3,4,6-tetra-O-acetyl-α-D-glucopyranosyl)-α-D-glucopyranosyl]-α-D-glucopyranosyl}-β-D-glucopyranoside (93)

Compound 92 (12.54 g, 9.85 mmol) and 2-bromoethanol (2.5 g, 1.4 ml, 20 mmol) were dissolved in dichloromethane (50 ml). Borontrifluoride etherate (7.1 g, 6.3 ml, 50 mmol) was added dropwise at room temperature and the mixture was stirred until the reaction was finished (48 h, TLC: SiO$_2$, ethyl acetate:isooctane 3:1). The mixture was washed (water, saturated sodium hydrogen carbonate), dried (Na$_2$SO$_4$) and evaporated. The residue (12.3 g) was chromatographed (SiO$_2$, ethyl acetate:isooctane 3:2) to give 93 (4.95 g, 63% based on transformed 92 and unreacted 92 (5.05 g). Compound 93 had $[\alpha]_D^{25}$ +109° (c 1.3, chloroform). $^1$H-NMR (CDCl$_3$, Me$_4$Si) δ 5.35, 5.28, 5.18 (3d, each 1H, J=3.8, 2.8 and 3.6 Hz, H1', H1'', H1'''), 4.60 (d, 1H, J=7.9 Hz, H1), 3.42–3.49 (m, 2H, CH$_2$-Br). $^{13}$C-NMR (CDCl$_3$, TMS) δ 170.6–169.3 (CO), 100.4 (C1), 95.9, 95.7, 95.3 (C1', C1'', C1'''), 77.3, 75.0, 73.7, 72.7, 72.2, 71.9, 71.8, 70.7, 70.4, 70.1, 69.9, 69.8, 69.7, 69.4, 69.3, 68.9, 68.5, 68.4, 67.4, 63.0, 61.8, 29.9, 21.1–20.6.

2-(2-Methoxycarbonylethylthio)ethyl 2,3,6-tri-O-acetyl-4-O-{2,3,6-tri-O-acetyl-4-O-[2,3,4-tri-O-acetyl-6-O-(2,3,4,6-tetra-O-acetyl-α-D-glucopyranosyl)-α-D-glucopyranosyl]-α-D-glucopyranosyl}-β-D-glucopyranoside (94)

Compound 93 (4.00 g, 3.0 mmol), methyl 3-mercaptopropionate (0.546 g, 0.49 ml, 4.5 mmol) cesium carbonate (1.17 g, 3.6 mmol) and N,N-dimethylformamide (25 ml), were stirred at room temperature until 93 had been consumed (7 h; TLC; SiO$_2$, ethyl acetate:isooctane 4:1). The solvent was removed and the residue was chromatographed (SiO$_2$, ethyl acetate:isooctane 3:1) to give 94 (3.22 g, 78%). $[\alpha]_D^{25}+102°$ (c 1.0, chloroform). $^1$H-NMR (CDCl$_3$, Me$_4$Si) δ 5.36, 5.28, 5.19 (3d, each 1H, J=3.8, 4.1 and 3.7 Hz, H1', H1'', H1'''), 4.57 (d, 1H, J=7.9 Hz, H1), 3.71 (s, 3H, MeO), 2.81, 2.71, 2.61 (3t, each 2H, J=6.7 Hz, CH$_2$—S—CH$_2$ and CH$_2$—CO). $^{13}$C-NMR (CDCl$_3$, Me$_4$Si) δ 100.2 (C1), 95.8, 95.6, 95.2 (C1', C1'', C1'''), 75.1, 73.7, 72.6, 72.0 71.9, 71.7, 70.7, 70.3, 70.0, 69.8, 69.6, 69.3, 69.2, 68.8, 68.4, 67.3, 65.2, 63.0, 62.9, 61.7, 60.3, 51.7, 34.6, 31.3, 27.2, 20.8–20.5.

2-(10-Methoxycarbonyldecylthio)ethyl 2,3,6-tri-O-acetyl-4-O-{2,3,6-tri-O-acetyl-4-O-[2,3,4-tri-O-acetyl-6-O-(2,3,4,6-tetra-O-acetyl-α-D-glucopyranosyl)-α-D-glucopyranosyl]-α-D-glucopyranosyl}-β-D-glucopyranoside (95)

Compound 93 (431 mg, 0.33 mmol), methyl 11-mercaptoundecanoate (105, 114 mg, 0.49 mmol), cesium carbonate (128 mg, 0.39 mmol) and N,N-dimethylformamide (3 ml) were stirred at room temperature for 15 h. The mixture was diluted with dichloromethane, washed with water (neutralization with Duolite H+ resin facilitated the phase separation), and dried (Na$_2$SO$_4$). The solvent was removed and the residue was chromatographed (SiO$_2$, ethyl acetate:isooctane 2:1) to give 95 (243 mg, 50%). $[\alpha]_D^{24}+91°$ (c 4.4, chloroform). $^1$H-NMR (CDCl$_3$, Me$_4$Si) δ 5.36, 5.28, 5.19 (3d, each 1H, J=3.8, 4.1 and 3.6 Hz, H1', H1'', H1'''), 4.57 (d, 1H, J=7.9 Hz, H1), 3.67 (s, 3H, MeO), 2.68, 2.52, 2.31 (3t, each 2H, J=7 Hz, CH$_2$—S—CH$_2$ and CH$_2$CO). $^{13}$C-NMR (CDCl$_3$, Me$_4$Si) δ 174.1, 170.4–169.1, 100.1 (C1), 95.6, 95.5, 95.1 (C1', C1'', C1'''), 75.0, 73.6, 72.5, 71.9, 71.5, 70.5, 70.2, 69.9, 69.7, 69.6, 69.2, 69.1, 69.1, 69.1, 68.7, 68.3, 67.2, 65.1, 62.9, 62.8, 61.6, 51.2, 33.9, 32.3, 31.1, 29.5, 29.2, 29.1, 29.0, 29.0, 28.9, 28.6, 24.7, 20.7–20.4.

2-(Octadecylthio)ethyl 2,3,6-tri-O-acetyl-4-O-{2,3,6-tri-O-acetyl-4-O-[2,3,4-tri-O-acetyl-6-O-(2,3,4,6-tetra-O-acetyl-α-D-glucopyranosyl)-α-D-glucopyranosyl]-α-D-glucopyranosyl}-β-D-glucopyranoside (96)

Compound 93 (265 mg, 0.2 mmol), octadecanethiol (86 mg, 0.3 mmol), cesium carbonate (79 mg, 0.24 mmol) and N,N-dimethylformamide (10 ml) were stirred at room temperature until 93 had been consumed (48 h; TLC, SiO$_2$, ethyl acetate:isooctane 4:1). The solvent was removed and the residue was chromatographed (SiO$_2$, ethyl acetate:isooctane 1:1) to give 96 (142 mg, 44%). $[\alpha]_D^{25}+93°$ (c 0.5, chloroform). $^1$H-NMR (CDCl$_3$, Me$_4$Si) δ 5.30, 5.22, 5.12 (3d, each 1H, J=4.0, 4.2 and 3.7 Hz, H1', H1'', H1'''), 4.51 (d, 1H, J=7.9 Hz, H1), 2.62, 2.46 (2t, each 2H, J=7.0 Hz, CH$_2$—S—CH$_2$). $^{13}$C-NMR (CDCl$_3$, Me$_4$Si) δ 170.5–169.1 (CO), 100.2 (C1), 95.7, 95.6, 95.2 (C1', C1'', C1'''), 75.1, 73.7, 72.6, 72.0, 71.6, 70.6, 70.3, 70.0, 69.8, 69.7, 69.6, 69.3, 69.2, 68.8, 68.4, 68.3, 67.3, 65.2, 63.0, 62.9, 61.7, 32.4, 31.8, 31.2, 29.6, 29.5, 29.5, 29.4, 29.2, 29.1, 28.7, 22.6, 20.8–20.5, 14.0.

Ethyl{4-O-[4-O-6-O-($\alpha$-D-glucopyranosyl)-$\alpha$-D-glucopyranosyl]-$\alpha$-D-glucopyranosyl}-$\beta$-D-glucopyranoside (97)

Compound 93 (122 mg) was dissolved in methanol (10 ml) and methanolic sodium methoxide (5 ml; from 1 mg of sodium) was added. Sodium hydroxide solution (0.1M, 5 ml) was added and the reaction mixture was hydrogenated (72 mg Pd/C; 4 atm.) over night and then neutralized with Duolite H+ resin and filtered. One drop of conc. ammonium hydroxide in water was added and the solvent was removed. The residue (106 mg) was chromatographed (SiO$_2$, chloroform:methanol:water, 65:35:10, lower phase) to give 97 (24 mg, 40%). [$\alpha$]$_D^{24}$+108° (c, 1.0, water). $^1$H-NMR (D$_2$O, TSP) $\delta$ 5.40 (d, 2H, J=3.8 Hz, H1' and H1''), 4.96 (d, 1H, J=3.7 Hz, H1'''), 4.49 (d, 1H, J=8.0 Hz, H1), 1.23 (t, 3H, J=7.1 Hz, CH$_2$CH$_3$). $^{13}$C-NMR (D$_2$O, TSP) $\delta$ 104.5 (C1), 102.7, 102.2, 100.8 (C1', C1'', C1'''), 79.8, 79.7, 79.0, 77.3, 76.0, 75.8, 75.8, 74.6, 74.5, 74.4, 74.2, 74.1, 73.9, 72.3, 72.2, 69.0, 68.6, 63.5, 63.2, 17.0.

2-(2-Methoxycarbonylethylthio)ethyl 4-O-{4-O-[6-O-($\alpha$-D-glucopyranosyl)-$\alpha$-D-glucopyranosyl]-$\alpha$-D-glucopyranosyl}-$\beta$-D-glucopyranoside (98)

Compound 94 (3.0 g, 2.2 mmol) was dissolved in methanol (25 ml) and added to a solution of sodium (1 mg) in methanol (75 ml). The reaction mixture was monitored by TLC (chloroform:methanol:water 65:35:10, lower phase). After 9 h at room temperature and 30 min at 40°, the solvent was removed and the residue was chromatographed (SiO$_2$, chloroform:methanol:water, 65:35:10, lower phase) to give 98 (1.50 g, 84%). [$\alpha$]$_D^{25}$+113° (c 0.7, water). $^1$H-NMR (D$_2$O, TSP) $\delta$ 5.41 (d, 2H, J=3.5 Hz, H1' and H1''), 4.98 (d, 1H, J=3.6 Hz, H1'''), 4.53 (d, 1H, J=7.9 Hz, H1), 3.75 (s, 3H, MeO). $^{13}$C-NMR (D$_2$O, TSP) $\delta$ 177.4 (CO), 104.3 (C1), 102.0, 101.6, 100.2 (C1', C1'', C1'''), 79.3, 79.1, 78.3, 76.7, 75.4, 75.2, 75.1, 73.9, 73.8, 73.6, 73.5, 73.3, 71.6, 71.5, 71.1, 68.0, 62.8, 62.7, 62.6, 62.6, 54.5, 36.3, 32.9, 28.6.

2-(10-Methoxycarbonyldecylthio)ethyl 4-O-{4-O-[6-O-($\alpha$-D-glucopyranosyl)-$\alpha$-D-glucopyranosyl]-$\alpha$-D-glucopyranosyl}-$\beta$-D-glucopyranoside (99)

Compound 95 (218 mg, 0.148 mmol) was deacetylated and purified essentially as above and freeze-dried to give 99 (100 mg, 73%). [$\alpha$]$_D^{24}$+94° (c 0.8, water). $^1$H-NMR (D$_2$O, TSP, 70°) $\delta$ 5.31 (m, 2H, H1' and H1'''), 4.93 (d, 1H, J=3.6 Hz, H1'''), 4.41 (d, 1H, J=7.9 Hz, H1), 3.64 (s, 3H, MeO), 2.76, 2.56 (2t, 2H each, J=7.0 Hz, CH$_2$—S—CH$_2$), 2.28 (t, 2H, J=7.3 Hz, CH$_2$—CO). $^{13}$C-NMR (D$_2$O, TSP, 65°) $\delta$ 178.0 (CO), 105.9, 103.6, 103.4, 101.6 (C1, C1', C1'', C1'''), 81.5, 81.4, 79.5, 78.2, 76.6, 76.4, 75.3, 75.0, 74.9, 74.8, 73.2, 72.9, 72.4, 69.5, 64.2, 54.8, 37.2, 35.4, 34.6, 32.9, 32.6, 32.5, 32.34, 32.3, 32.2, 31.9, 28.0.

2-(Octadecylthio)ethyl 4-O-{4-O-[6-O-($\alpha$-D-glucopyranosyl)-$\alpha$-D-glucopyranosyl]-$\alpha$-D-glucopyranosyl}-$\beta$-D-glucopyranoside (100)

Compound 96 (120 mg, 0.079 mmol) was deacetylated essentially as above and freeze-dried to give 100 (73 mg, 95%). The reaction was monitored by TLC (SiO$_2$, acetic acid:methanol:water 2:1:1). [$\alpha$]$_D^{24}$+77° (c 0.6, chloroform:methanol 1:1). $^1$H-NMR (D$_2$O, TSP) $\delta$ 5.35, 5.33 (2d, each 1H, J=3.9 Hz, H1' and H1''), 4.96 (d, 1H, J=3.5 Hz, H1'''), 4.44 (d, 1H, J=7.9 Hz, H1), 2.80, 2.58 (2t, each 2H, J=7.0 Hz, CH$_2$—S—CH$_2$). $^{13}$C-NMR (CDCl$_3$, (CD$_3$)$_2$SO, Me$_4$Si) $\delta$ 102.8, 101.7, 100.8, 98.8 (C1, C1', C1'', C1'''), 81.5, 81.4, 80.1, 76.1, 73.3, 73.1, 72.8, 72.3, 72.2, 72.1, 72.0, 71.7, 70.2, 70.1, 68.7, 60.8, 31.7, 31.4, 30.8, 29.3, 29.1, 28.8, 28.3, 22.2, 14.0.

Neoglycoprotein 101 was prepared as described for 69 and 89, using 98 (56 mg, 0.07 mmol) and bovine serum albumin (BSA, 65 mg, 1 $\mu$mol). The degree of binding was 8. With 0.07 mmol of 98 and 0.5 $\mu$mol of BSA, the degree of binding was 20.

Neoglycoprotein 102 was prepared as described for 70 and 90, using 98 (112 mg, 0.14 mmol) and key-hole limpet haemocyanin (KLH, 30 mg, 0.034 $\mu$mol; assumed molecular weight, 870 000; supplier, Schwartz/Mann, Spring Valley, N.Y.). The degree of binding was 65. With 0.7 mmol of 98 and 0.034 mol of KLH, the degree of binding was 245.

Methyl 11-bromoundecanoate 103

11-Bromoundecanoic acid (commercial material, 25.0 g, 94 mmol), Duolite H+ resin (10 g), calcium chloride (26.2 g, 94 mmol) and methanol (700 ml) were stirred for 15 h. The methanol was removed and dichloromethane was added. The mixture was washed with water, dried (Na$_2$SO$_4$) and concentrated. Distillation gave pure 103 (22.0 g, 84%) with b.p. 103°–104° (2×10$^{-2}$ torr). $^1$H-NMR (CDCl$_3$, Me$_4$Si) $\delta$ 3.67 (s, 3H, MeO), 3.41 (t, 2H, J=6.8 Hz, Br—CH$_2$), 2.31 (t, 2H, J=7.3 Hz, CH$_2$CO).

Methyl 11-thioacetylundecanoate 104

Compound 103 (17.8 g, 64 mmol), thioacetic acid (9.7 g, 9.0 ml, 128 mmol), methyltrioctylammonium chloride (0.5 g), cesium carbonate (25 g, 77 mmol), dichloromethane (95 ml) and water (95 ml) were stirred at room temperature for 15 h. The reaction was monitored by TLC (SiO$_2$, ethyl acetate:isooctane, 1:5). The mixture was extracted with dichloromethane and the combined extracts were dried (Na$_2$SO$_4$) and concentrated. Distillation gave pure 104 (15.6 g, 89%) with b.p. 137°–139° (0.1 torr) and m.p. <25° (from isooctane). $^1$H-NMR (CDCl$_3$, Me$_4$Si) $\delta$ 3.67 (s, 3H, MeO), 2.86 (t, 2H, J=7.1 Hz, S—CH$_2$), 2.32 (s, 3H, MeCO), 2.30 (t, 2H, J=7.7 Hz, CH$_2$CO). $^{13}$C-NMR (CDCl$_3$, Me$_4$Si) $\delta$ 195.9, 174.1 (CO), 51.3, 34.0, 30.5, 29.4, 29.3, 29.2, 29.1, 29.0, 28.9, 28.7, 24.8.

Anal. Calc. for C$_{14}$H$_{26}$O$_3$S: C, 61.27; H, 9.50. Found: C, 60.80; H, 9.79.

Methyl 11-mercaptoundecanoate 105

Compound 104 (15.6 g, 56.9 mmol) in methanol (50 ml) was added to a solution of hydrogen chloride in methanol (HCl was bubbled into 600 ml of MeOH for 10 min). The reaction was monitored by TLC (SiO$_2$, ethyl acetate:isooctane 1:5). After 48 h, an excess of sodium hydrogen carbonate was added and the mixture was diluted with dichloromethane (150 ml), filtered and concentrated. Distillation gave pure 105 (9.0 g, 68%) with b.p. 93°–94° ($7\times10^{-2}$ torr). $^1$H-NMR (CDCl$_3$, Me$_4$Si) δ 3.68 (s, 3H, MeO), 2.53 (q, 2H, J~7 Hz, H—S—CH$_2$), 2.31 (t, 2H, J=7.5 Hz, CH$_2$CO). $^{13}$C-NMR (CDCl$_3$, Me$_4$Si) δ 174.2 (CO), 51.3, 34.0, 33.9, 29.3, 29.2, 29.1, 29.0, 28.9, 28.3, 24.8, 24.5.

REFERENCES

1a R. C. Hughes and S. D. J. Pena in "Carbohydrate Metabolism and its Disorders", P. J. Randle, D. F. Steiner, and W. J. Whelan, Eds. Academic Press, London, 1981.
b S. Hakomori, *Ann. Rev. Biochem.*, 50, 733 (1981).
c J. Montreuil, *Adv. Carbohydr. Chem. Biochem.*, 37, 157 (1980).
d "Symposia of the Society of Experimental Biology; Symposium XXXII Cell-Cell Recognition" Cambridge University Press, 1978.
e W. J. Lennartz, "The Biochemistry of Glycoproteins and Proteoglycans", Plenum Press, New York, 1980.
f N. Sharon and H. Lis, *Chem. Eng. News*, March 30, 21, (1981).
g D. M. Weir, *Immunology Today*, August, 45 (1980).
h T. Feizi, *TIBS*, December, 333 (1981).
2 R. U. Lemieux, *Chem. Soc. Rev.* 423 (1978).
3 N. Sharon and H. Lis, *Science*, 177, 949 (1972).
4 E. A. Kabat, *Methods Enz.*, 70, 3 (1980).
5a E. H. Beachey, *J. Infect. Diseases*, 143, 325 (1981).
b R. J. Gibbons, *Microbiology*, 395 (1977).
c T. Wadström and T. J. Trust, "Bacterial Surface Lectins", to be published.
d J. W. Costerton, G. G. Geesey, and K-J. Cheng, *Scientific American*, 238, 86 (1978).
e "Bacterial Adherence", E. H. Beachey Ed., Chapman and Hall, London, New York, 1980.
6a C. W. Ward, P. A. Gleeson, and T. A. Dopheide, *Biochem. J.*, 189, 649 (1980).
b M. A. K. Markwell, L. Svennerholm, and J. C. Paulson, *Proc. Natl. Acad. Sci.*, 78, 5406 (1981).
7 J. Holmgren, *Nature*, 292, 413 (1981).
8 L. D. Kohn in "Receptors and Recognition" P. Cuatrecasas and M. F. Greaves Eds., Vol. 5, p. 134–212. Chapman and Hall, London 1978.
9 D. I. Meyer and M. M. Burger in "Cancer-The Outlaw Cell", R. E. LaFond, Ed., Am. Chem. Soc., Washington DC, 1978.
10a J. M. Bedford, *Nature*, 291, 286 (1981).
b F. Rosati and R. De Santis, *Nature*, 283, 762 (1980).
11a Recent Advances in Phytochemistry, Vol. 15: "Phytochemistry of Cell Recognition and Cell Surface Interactions", F. A. Loewus and C. A. Ryan, Eds., Plenum Publishing Corp., New York, 1981.
b G. R. Noggle, *What's New in Plant Physiology*, 10(2), 5 (1979).
12 M. M. Ponpipom, R. L. Bugianesi, and T. Y. Shen, *Can. J. Chem.*, 58, 214 (1980).
13a J. C. Chabala and T. Y. Shen, *Carbohydr. Res.*, 67, 55 (1978).
b J. S. Slama and R. R. Rando, *Biochemistry*, 19, 4595 (1980).
14 J. H. Pazur, *Adv. Carbohydr. Chem. Biochem.*, 39, 404 (1981).
15 A. F. Bochkov and G. E. Zaikov, "Chemistry of the O-Glycosidic Bond: Formation and Cleavage", Pergamon Press, 1979.
16a Review: C. P. Stowell and Y. C. Lee, *Adv. Carbohydr. Chem. Biochem.*, 37, 225 (1980).
b Review: J. D. Aplin and J. C. Wriston, Jr., *CRC Critical Rev. Biochem.*, May 1981, p. 259–306.
17a R. T. Lee and Y. C. Lee, *Carbohydr. Res.* 37, 193 (1974).
b J. C. Jacquinet and H. Paulsen, *Tetrahedron Lett.* 22, 1387 (1981).
c M. A. Bernstein and L. D. Hall, *Carbohydr. Res.*, 78, Cl (1980).
18 F. Marquez and A. Mesquida, *Anales de Quimica*, 70, 833 (1974).
19 R. R. Race and R. Sanger, *Blood Groups in Man*, 6th edn., Blackwell, Oxford, 1975; M. Naiki and M. Kato, *Vox Sang.*, 37 30–38, (1979).
20 G. Källenius, R. Möllby, S. B. Svenson, J. Winberg, A. Lundblad, S. Svensson, and B. Cedergren, *FEMS Lett.*, 7 297–302 (1980); H. Leffler and C. Svanborg-Eden, ibid. 8 127–134 (1980).
21a G. O. Aspinall and R. S. Fanshawe, *J. Chem. Soc.* 4215–4225 (1961).
b M. E. Chacon-Fuertes, and M. Martin-Lomas, *Carbohydr. Res.* 43 51–56 (1975).
c P. A. Gent, R. Gigg, and A. A. E. Penglis, *J. Chem. Soc., Perkin Trans.* 1, 1395–1404 (1976).
d D. D. Cox, E. K. Metzner, and E. J. Reist, *Carbohydr. Res.*, 62 245–252 (1978).
e P. J. Garegg and H. Hultberg, ibid. 110 261–266 (1982).
f M-L. Milat, P. A. Zollo, and P. Sinay, ibid 100 263–271 (1982).
g J. Dahmen, T. Frejd, T. Lave, F. Lindh, G. Magnusson, G. Noori, and K. Pålsson, ibid. 113 219–224 (1983).
22a D. D. Cox, E. K. Metzner, and E. J. Reist, *Carbohydr. Res.*, 63 139–147 (1978).
b P. J. Garegg and H. Hultberg, ibid. 110 261–266 (1982).
23 M. A. Nashed and L. Anderson, *Carbohydr. Res.*, 114 43–52 (1983).
24 H. Paulsen and A. Bunsch, *Carbohydr. Res.*, 101 21–30 (1982).
25 P. Hallgren, G. Hansson, K. G. Henriksson, A. Häger, A. Lundblad, and S. Svensson, *Europ. J. Clin. Invest.*, 4 429–433 (1974).
26 G. Lennartson, A. Lundblad, J. Lundsten, S. Svensson, and A. Häger, *Eur. J. Biochem.*, 83 325–334 (1978).
27 A. Lundblad, S. Svensson, I. Yamashina, and M. Ohta, *FEBS Lett.*, 97 249–252 (1979).
28 P. Hallgren, B. S. Lindberg, and A. Lundblad, *J. Biol. Chem.*, 252 1034–1040 (1977).
29 D. A. Zopf, R. E. Levinson, and A. Lundblad, *J. Immun. Methods*, 48 109–119 (1982).
30 G. Magnusson, G. Noori, J. Dahmen, T. Frejd, and T. Lave, *Acta Chem. Scand.*, B35, 213 (1981).
31 B. Lindberg, *Acta Chem. Scand.*, 2, 426–429 (1948).
32 R. J. Ferrier and R. H. Furneaux, *Methods Carbohydr. Chem.*, 8, 251 (1980).
33 See ref. 15, p. 20.
34 N. Morishima, S. Koto, C. Kusuhara, and S. Zen, *Chem. Lett.*, 427 (1981).
35 R. U. Lemieux, K. B. Hendriks, R. V. Stick, and K. James, *J. Am. Chem. Soc.*, 97, 4056 (1975).
36 See ref. 15, p. 48.
37 Varian XL-200. See G. A. Morris and R. Freeman, *J. Am. Chem. Soc.*, 101, 760 (1979).
38 a R. P. Volante, *Tetr. Lett.*, 3119 (1981).
b J. H. Chapman and L. N. Owen, *J. Chem. Soc.* 579 (1950).

39 P. A. S. Smith in "Molecular Rearrangements" part 1, p. 577, P. de Mayo, Ed., Interscience, New York, 1963.
40 R. U. Lemieux, D. R. Bundle, and D. A. Baker, *J. Am. Chem. Soc.*, 97, 4076 (1975).
41 J. K. Inman, B. Merchant, L. Claflin, and S. E. Tacey, *Immunochemistry*, 10, 165 (1973).
42 M. Dubois, K. A. Gilles, J. K. Hamilton, P. A. Rebers. and F. Smith, *Analyt. Chem.*, 28 350 (1956).
43a C. R. McBroom, C. H. Samanen, and I. J. Goldstein, *Methods Enzymol.*, 28, 212 (1972).
b D. F. Smith, D. A. Zopf, and V. Ginsburg, ibid., 50, 169 (1978).
44 J. E. Hodge and B. T. Hofreiter, *Methods Carbohydr. Chem.*, I, 389 (1962).
45 A. Shöberl and A. Wagner in Houben-Weyl "Methoden der Organischen Chemie", Georg Thieme Verlag, Stuttgart 1955, Vol. 9, p. 55.
46 D. M. Hall, *Carbohydr. Res.*, 86 158-160 (1980).
47 Garegg and H. Hultberg, *Carbohydr. Res.*, 93 C10-C11 (1981).
48 B. R. Baker, M. V. Querry, S Bernstein, S. R. Safir, and Y. Subbarow, *J. Org. Chem.*, 12 167-173 (1947).
49 J. S. Sawardeker, J. H. Sloneker, and A. Jeanes, *Anal. Chem.*, 37 1602-1604 (1965).
50 H. Björndal, C. G. Hellerqvist, B. Lindberg, and S. Svensson, *Angew. Chem. Int. Ed. Engl.*, 9 610-619 (1970).
51 B. V. McCleary, *Carbohydr. Res.*, 85 160-163 (1980).
52 B. J. Catley, *J. General Microbiol.*, 78 33-38 (1973).
53 C. Auge and A. Veyriers, *Carbohydr. Res.*, 46, 293 (1976).
54 R. U. Lemieux and R. M. Ratcliffe, *Can. J. Chem.*, 57, 1244 (1979).
55 See ref. 48
56 E. Fisher and F. Armstrong, *Ber.*, 35, 3155 (1902).
57 A. R. Pray, *Inorg. Synth.*, 5, 154 (1957).
58 R. U. Lemieux and J. D. Stevens, *Can. J. Chem.*, 43 2059-2070 (1965).
59 "Protective Groups in Organic Chemistry", J. F. W. McOmie, Ed. Plenum Press, London, 1973.
60 A. H. Haines, *Adv. Carbohydr. Biochem.*, 39, 13 (1981).

TABLE 1.

| | Product data and yields for the preparation of 2-bromoethyl glycosides | | | | |
|---|---|---|---|---|---|
| Product | | Method[a] | Yield (%)[b] | M.p. (°C.) | $[\alpha]_D^{24}$ (°) |
| 1 | (structure) | A | 46 | 114-116 | −5.2 (c 1.4, CDCl$_3$) |
| 2 | (structure) | D | 18[c] (2α)<br>30[c] (2α + 2β) | sirup | +30.5 (c 1.4, CHCl$_3$) |
| 3 | (structure) | A | 42 | 119-120 | −10.9 (c 1.2, CDCl$_3$) |
| 4 | (structure) | A | 58 | 118-119 | +44.7 (c 0.6, CDCl$_3$) |
| 5 | (structure) | A | 36 | 142-143 | −21.4 (c 0.8, CDCl$_3$) |
| 6 | (structure) | A | 85 | 144-145 | −47.9 (c 1.7, CDCl$_3$) |
| 7 | (structure) | A | 53[c] (7β)<br>16[c] (7α) | sirup<br>sirup | −24.7 (c 2.2, CDCl$_3$)<br>−22.4 (c 0.8, CDCl$_3$) |

TABLE 1.-continued

Product data and yields for the preparation of 2-bromoethyl glycosides

| Product | Method[a] | Yield (%)[b] | M.p. (°C.) | $[\alpha]_D^{24}$ (°) |
|---|---|---|---|---|
| 8 | C | 39 | 174–175 | −6.6 (c 1.1, CDCl$_3$) |
| 9 | A | 50[c] | 111–114 | +21.4 (c 1.0, CHCl$_3$) |
| 10 | A | 55[c] | 224–225 | +9.3 (c 1.0, CHCl$_3$) |
| 11 | A | 80[c] | sirup | −11.0 (c 0.7, CHCl$_3$) |
| 12 | E | 8[c] | sirup | +127 (c 1.0, CHCl$_3$) |
| 13 | A | 55[c] | amorph. | −10.9 (c 1.3, CHCl$_3$) |
| 14 | A | 67[c] | amorph. | +5.8 (c 2.4, CDCl$_3$) |

TABLE 1.-continued

Product data and yields for the preparation of 2-bromoethyl glycosides

| Product | Method[a] | Yield (%)[b] | M.p. (°C.) | $[\alpha]_D^{24}$ (°) |
|---|---|---|---|---|
| 15 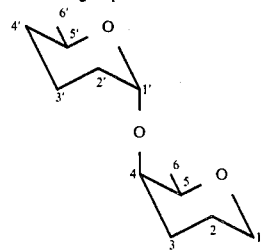 | B | 77[c] | 174–177 | +75.2 (c 2.0, CHCl₃) |

[a]See EXAMPLES.
[b]Isolated by spontaneous crystallisation of the crude reaction mixture.
[c]Isolated by chromatography on silica gel.

TABLE 2.

$^{13}$C—NMR chemical shifts for per-O—acetylated 2-bromoethyl glycosides.

Chemical shift[a]

| Nr | C1 | C2 | C3 | C4 | C5 | C6 | C7[c] | C8[c] | C1' | C2' | C3' | C4' | C5' | C6' | CH₃ | | CO (acetyl) | |
|---|---|---|---|---|---|---|---|---|---|---|---|---|---|---|---|---|---|---|
| 1 | 102.0 | 71.3[b] | 71.2 | 70.2 | 67.4 | 61.7 | 69.0 | 30.4 | | | | | | | 21.3 | 21.1 | 170.8 | 170.7 |
|   |       |          |      |      |      |      |      |      | | | | | | | 21.1 | 21.0 | 170.6 | 170.0 |
| 3 | 101.5 | 73.1 | 72.4 | 71.5 | 70.2 | 62.3 | 68.8 | 30.3 | | | | | | | 21.1 | 21.2 | 171.1 | 170.7 |
|   |       |      |      |      |      |      |      |      | | | | | | | 21.0 | 21.0 | 169.8 | 169.8 |
| 4 | 98.2 | 69.9 | 69.5 | 69.4 | 66.5 | 62.9 | 69.0 | 30.1 | | | | | | | 21.3 | 21.2 | 171.1 | 170.5 |
|   |      |      |      |      |      |      |      |      | | | | | | | 21.2 | 21.1 | 170.3 | 170.2 |
| 5 | 101.4 | 73.1 | 72.4 | 71.5 | 70.4 | 167.6 | 69.9 | 30.3 | | | | | | | 21.2 | 21.1 | 170.6 | 169.9 |
|   |       |      |      |      |      |       |      |      | | | | | | | 21.0 | 53.5 | 169.8 |       |
| 6 | 100.7 | 71.0 | 70.4 | 68.7 | 62.0 |       | 69.2 | 30.0 | | | | | | | 20.8 | 20.8 | 170.0 | 169.8 |
|   |       |      |      |      |      |       |      |      | | | | | | | 20.8 |      | 169.5 |       |
| 7α | 96.4 | 71.1 | 68.1 | 67.9 | 64.8 | 15.9 | 68.4 | 30.2 | | | | | | | 20.9 | 20.7 | 170.6 | 170.6 |
|    |      |      |      |      |      |      |      |      | | | | | | | 20.7 |      | 170.0 |       |
| 7β | 101.3 | 71.2 | 70.1 | 69.3 | 68.7 | 16.1 | 69.5 | 30.1 | | | | | | | 20.7 | 20.7 | 170.6 | 170.2 |
|    |       |      |      |      |      |      |      |      | | | | | | | 20.6 |      | 169.6 |       |
| 8 | 100.7 | 54.5 | 72.2 | 71.7 | 69.0 | 62.2 | 69.5 | 30.4 | | | | | | | 23.3 | 20.7 | 170.9 | 170.7 |
|   |       |      |      |      |      |      |      |      | | | | | | | 20.7 | 20.6 | 170.6 | 169.4 |
| 9 | 98.3 | 54.4 | 72.0 | 70.6 | 68.9 | 61.9 | 69.8 | 29.8 | | | | | | | 20.8 | 20.6 | 170.7 | 170.1 |
|   |      |      |      |      |      |      |      |      | | | | | | | 20.5 |      | 169.4 |       |
| 10 | 98.0 | 54.7 | 72.7 | 75.4 | 66.5 | 62.0 | 69.7 | 29.8 | 101.0 | 71.0 | 70.9 | 70.6 | 69.0 | 60.6 | 20.8 | 20.6 | 170.4 | 170.3 |
|    |      |      |      |      |      |      |      |      |       |      |      |      |      |      | 20.5 | 20.5 | 170.1 | 170.0 |
|    |      |      |      |      |      |      |      |      |       |      |      |      |      |      |      |      | 169.7 | 169.0 |
| 11 | 98.7 | 51.2 | 71.0 | 66.7 | 67.9 | 61.4 | 69.8 | 29.9 | | | | | | | 20.7 | 20.7 | 170.4 | 170.3 |
|    |      |      |      |      |      |      |      |      | | | | | | | 20.5 |      | 169.8 |       |
| 12 | 98.4 | 57.3 | 67.2 | 67.6 | 68.1 | 61.7 | 68.9 | 29.5 | | | | | | | 20.71 | 20.67 | 170.4 | 170.0 |
|    |      |      |      |      |      |      |      |      | | | | | | | 20.63 |       | 169.8 |       |
| 13 | 101.1 | 72.8 | 71.4 | 76.2 | 70.7 | 61.9 | 69.8 | 29.8 | 100.8 | 72.6 | 71.0 | 69.1 | 66.6 | 60.8 | 20.8 | 20.8 | 170.4 | 170.4 |
|    |       |      |      |      |      |      |      |      |       |      |      |      |      |      | 20.8 | 20.8 | 170.3 | 170.1 |
|    |       |      |      |      |      |      |      |      |       |      |      |      |      |      | 20.6 | 20.6 | 170.0 | 169.7 |
|    |       |      |      |      |      |      |      |      |       |      |      |      |      |      | 20.6 |      | 169.0 |       |
| 14 | 101.9 | 73.1 | 70.1 | 74.2 | 68.7 | 63.3 | 69.0 | 30.2 | 100.9 | 72.0 | 70.1 | 68.5 | 66.9 | 61.3 | 20.9 | 20.8 | 170.6 | 170.4 |
|    |       |      |      |      |      |      |      |      |       |      |      |      |      |      | 20.8 | 20.8 | 170.2 | 170.2 |
|    |       |      |      |      |      |      |      |      |       |      |      |      |      |      | 20.6 | 20.6 | 170.2 | 169.5 |
|    |       |      |      |      |      |      |      |      |       |      |      |      |      |      | 20.6 |      | 169.4 |       |
| 15 | 101.3 | 72.5 | 68.5 | 76.9 | 67.8 | 60.5 | 69.5 | 30.0 | 99.3 | 72.0 | 68.4 | 67.3 | 67.1 | 61.9 | 20.9 | 20.7 | 170.6 | 170.5 |
|    |       |      |      |      |      |      |      |      |      |      |      |      |      |      | 20.7 | 20.7 | 170.4 | 170.4 |
|    |       |      |      |      |      |      |      |      |      |      |      |      |      |      | 20.6 | 20.6 | 170.1 | 169.8 |
|    |       |      |      |      |      |      |      |      |      |      |      |      |      |      | 20.6 |      | 169.2 |       |

[a]ppm, CDCl₃ internal TMS.
[b]underlined values can be interchanged.
[c]identified by the INEPT[37] technique.
Numbering of positions:

TABLE 3.

$^1$H—NMR chemical shifts[a] and coupling constants[b] for per-O—acetylated 2-bromoethyl glycopyranosides[c]

| Nr | H1 | H2 | H3 | H4 | H5ax | H5eq | H6 | H6' | O—CH$_2$—CH$_2$ | CH$_2$—CH$_2$Br | CH$_3$—CO | |
|---|---|---|---|---|---|---|---|---|---|---|---|---|
| 1 | 4.55[a] | 5.24 | 5.03 | 5.41 | 3.75–3.87 | | 4.10–4.25 | | 3.87–4.20 | 3.43–3.53 | 2.16 | 2.09 |
|  | (J$_{1,2}$7.8)[b] | (J$_{2,3}$10.5) | (J$_{3,4}$3.5) | (J$_{4,5}$1.0) | (m[d]) | | (m) | | (m) | (m) | 2.06 | 1.99 |
| 3 | 4.58 | 5.03 | 5.23 | 5.09 | 3.66–3.78 | | 4.10–4.34 | | 3.78–4.20 | 3.42–3.51 | 2.10 | 2.08 |
|  | (J$_{1,2}$7.8) | (J$_{2,3}$9.5) | (J$_{3,4}$9.5) | (J$_{4,5}$9.5) | (m) | | (m) | | (m) | (m) | 2.03 | 2.02 |
| 4 | 4.88 | | 5.20–5.40 | | 4.09–4.19 | | 4.10–4.34 | | 3.83–4.50 | 3.53 | 2.16 | 2.11 |
|  | (J$_{1,2}$1.5) | | (m) | | (m) | | (m) | | (m) | (t, J 5.8) | 2.06 | 2.00 |
| 5 | 4.63 | 5.04 | 5.29 | 5.22 | 4.06 | 3.77(COOCH$_3$) | | | 3.75–4.27 | 3.43–3.50 | 2.06 | 2.02 |
|  | (J$_{1,2}$7.6) | (J$_{2,3}$9.5) | (J$_{3,4}$9.5) | (J$_{4,5}$9.4) | | | | | (m) | (m) | 2.02 | |
| 6 | 4.56 | 5.03–4.90 | 5.17 | 5.03–4.90 | 4.15 | 3.39 | | | 3.75–4.15 | 3.47 | 2.08 | 2.06 |
|  | (J$_{1,2}$6.7) | (J$_{2,3}$8.3) | (J$_{3,4}$8.3) | (J$_{4,5ax}$5.0;J$_{4,5eq}$8.5;J$_{5ax,5eq}$12.0) | | | | | (m) | (t, J 6.0) | 2.05 | |
| 7α | 5.14 | | 5.05–5.43 | | 4.26 | | 1.12 | | 3.81   3.84 | 3.50 | 2.17 | 2.10 |
|  | (J$_{1,2}$0) | | (m) | | (J$_{5,6}$6.4) | | | | (J$_{AB}$-12.0) | (t, J 5.8) | 2.00 | |
|  | | | | | | | | | c.f. FIG. 3 | | | |
| 7β | 4.49 | 5.17–5.26 | 5.02 | 5.17–5.26 | 3.73–3.88 | | 1.20 | | 3.73–4.32 | 3.43–3.50 | 2.17 | 2.07 |
|  | (J$_{1,2}$7.9) | (J$_{2,3}$10.5) | (J$_{3,4}$3.5) | (m) | (J$_{5,6}$6.4) | | | | (m) | (m) | 1.98 | |
| 8 | 4.77 | 3.78–3.93 | 5.32 | 5.07 | 3.66–3.78 | | 4.08–4.31 | | 3.78–4.19 | 3.48 | 2.08 | 2.02 |
|  | (J$_{1,2}$8.0) | (J$_{2,3}$10.0) | (J$_{3,4}$10.0) | (J$_{4,5}$10.0) | (m) | | (m) | | (m) | (t, J 6.0) | 2.01 | 1.96 |
| 9 | 5.43 | 4.35 | 5.82 | 5.19 | | 3.80–4.40 | | | 3.70–4.20 | 3.30–3.40 | 2.13 | 2.04 |
|  | (J$_{1,2}$8.4) | (J$_{2,3}$10.7) | (J$_{3,4}$9.6) | (J$_{4,5}$9.6) | | (m) | | | (m) | (m) | 1.88[e] | |
| 11 | 5.37 | 4.57 | 5.83 | 5.50 | | 4.10–4.25 | | | 3.76 | 3.34 | 2.21 | 2.02 |
|  | (J$_{1,2}$8.5) | (J$_{2,3}$11.5) | (J$_{3,4}$3.4) | | | (m) | | | (m) | (m) | 1.87 | |
| 12 | 5.07 | 3.68 | 5.39 | 5.48 | 4.37 | | 4.12   4.09 | | 3.88–4.05 | 3.55 | 2.15 | 2.06 |
|  | (J$_{1,2}$3.7) | (J$_{2,3}$11.2) | (J$_{3,4}$3.4) | (J$_{4,5}$<1) | (J$_{5,6}$—6) | | (m) | | (m) | (t, J 6.0) | 2.06 | |

| Nr | H1 | H2 | H3 | H4 | H1' | H2' | H3' | H4' | CH$_2$Br | CH$_3$CO | |
|---|---|---|---|---|---|---|---|---|---|---|---|
| 13 | 4.54 | 5.21 | 4.92 | 4.49 | 5.12 | 4.96 | 5.35 | | 3.44 | 2.15 | 2.13 |
|  | (J$_{1,2}$8.0) | (J$_{2,3}$9.5) | (J$_{3,4}$8.0) | (J$_{1',2'}$8.0) | (J$_{2',3'}$10.5) | (J$_{3',4'}$3.5) | (J$_{4',5'}$1.0) | | (t, J 6.0) | 2.06 | 2.05 |
|  | | | | | | | | | | 2.04 | 1.97 |
| 14 | 4.49 | 5.10 | 4.89 | 4.42 | 5.25 | 5.01 | 5.36 | | 3.47 | 2.17 | 2.15 |
|  | (J$_{1,2}$7.8) | (J$_{2,3}$10.0) | (J$_{3,4}$3.0) | (J$_{1',2'}$7.9) | (J$_{2',3'}$10.5) | (J$_{3',4'}$3.5) | (J$_{4',5'}$1.0) | | (t, J 6.0) | 2.11 | 2.08 |
|  | | | | | | | | | | 2.06 | 2.04 |
|  | | | | | | | | | | 1.99 | |
| 15 | 4.54 | 5.22 | 4.83 | 5.01 | 5.39 | 5.21 | 5.57 | | 3.49 | 2.15 | 2.12 |
|  | (J$_{1,2}$8.0) | (J$_{2,3}$11.0) | (J$_{3,4}$3.0) | (J$_{1',2'}$3.0) | (J$_{2',3'}$11.0) | (J$_{3',4'}$3.0) | (J$_{4',5'}$1.0) | | (t, J 5.0) | 2.11 | 2.09 |
|  | | | | | | | | | | 2.06 | 2.00 |
| 10 | 5.42 | | 5.77 | 4.55 | 5.13 | 4.97 | 5.34 | | | | |
|  | (J$_{1,2}$8.5) | | (J$_{3,4}$7.9) | (J$_{1',2'}$7.9) | (J$_{2',3'}$7.7) | (J$_{3',4'}$3.3) | (J$_{4',5'}$<1.0) | | | | |

[a] ppm, CDCl$_3$, internal TMS.
[b] observed spacing.
[c] For numbering, see Table 2.
[d] complex pattern, "multiplet".

TABLE 4.

Product data and yields for the preparation of ω-bromoalkyl glycosides (c.f. Method A in Figure 2)

| Product | Starting alcohol | Yield (%)[a] | M.p. (°C.) | [α]$_D$ (°) |
|---|---|---|---|---|
| 16; D-Gal | 3-bromopropanol | 53 | 68–70 | +7.7 (c 1.0, CHCl$_3$) |
| 17; D-Glc | 3-bromopropanol | 90 | 67–68 | +0.4 (c 1.1; CHCl$_3$) |
| 18; D-GlcNPhth | 11-bromoundecanol | 35 | sirup | +15.6 (c 1.0; CHCl$_3$) |

[a] Isolated by chromatography on silica gel.

TABLE 5.
Product yields in the reaction:
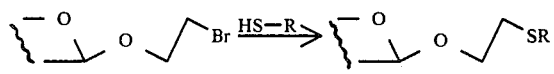
| Product | | Method[a] | Yield (%)[b] |
|---|---|---|---|
| 19 | Tetra-OAc-sugar-O-CH₂CH₂-S-CH₂CH₂-COOMe | F | 73 |
| 20 | Tetra-OAc-sugar-O-CH₂CH₂-S-C₆H₄-NH₂ | F | 71 |
| 21 | Tetra-OAc-sugar-O-CH₂CH₂-S-(alkyl chain) | F | 70 |
| 22 | Di(tetra-OAc-sugar)-O-CH₂CH₂-S-CH₂CH₂-COOMe | F | 80 |
| 23 | Di(tetra-OAc-sugar)-O-CH₂CH₂-S-(alkyl chain) | F | 71 |
| 24 | Di(tetra-OAc-sugar)-O-CH₂CH₂-S-(long alkyl chain) | G | 69 |
| 25 | Tetra-OAc-sugar-O-CH₂CH₂-S-C₆H₄-NO₂ | G | 62 |

TABLE 5.-continued
Product yields in the reaction:

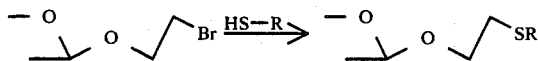

| Product | | Method[a] | Yield (%)[b] |
|---|---|---|---|
| 26 | 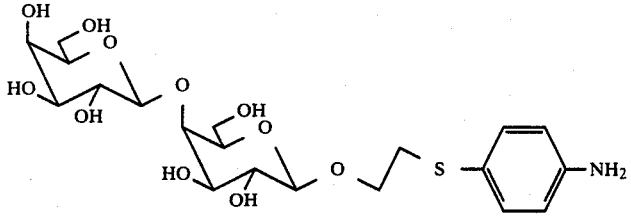 | G | 99 |
| 27 | 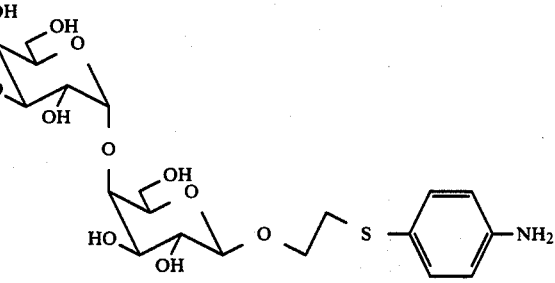 | G | 97 |

[a]Method F: Phase transfer catalysis; benzene/$H_2O$/$Cs_2CO_3$ or NaOH/$(C_8H_{17})_3NCH_3Br$.
Method G: DMF/NaH or $Cs_2CO_3$. For details, see EXAMPLES.
[b]Pure compound by chromatographic isolation.

What is claimed is:

1. An O-glycoside having the general formula:

(sugar)$_n$—O—(CH$_2$)$_m$—S—R—R' wherein n is an integer of from 1–10, inclusive, m is 2, R is selected from the group consisting of alkyl having 1–25 carbon atoms and aryl and R' is selected from the group consisting of H, CHO, CH(OR")$_2$, NO$_2$, NH$_2$, OH, SH, COOH, COOCH$_3$, COOCH$_2$CH$_3$, CONHNH$_2$ and CON$_3$, wherein R" is C$_{1-4}$-alkyl, and wherein the sugar is an aldose selected from the group consisting of D-glucose, D-galactose, D-mannose, D-xylose, L-fucose, 2-acetamido-2-deoxy-D-glucose, 2-deoxy-2-phthalimido-glucose, 2-acetamido-2-deoxy-D-galactose, 2-azido-2-deoxy-D-glucose, 2-azido-2-deoxy-D-galactose, D-glucuronic acid and D-galacturonic acid, 2-deoxy-2-phthalimido glucose and 2-deoxy-2-phthalimido galactose.

* * * * *